United States Patent [19]

Mason et al.

[11] Patent Number: 5,525,488
[45] Date of Patent: Jun. 11, 1996

[54] NUCLEIC ACID ENCODING THE MATURE α CHAIN OF INHIBIN AND METHOD FOR SYNTHESIZING POLYPEPTIDES USING SUCH NUCLEIC ACID

[75] Inventors: Anthony J. Mason; Peter H. Seeburg, both of San Francisco, Calif.

[73] Assignee: Genentech, Inc., S. San Francisco, Calif.

[21] Appl. No.: 197,792

[22] Filed: Feb. 17, 1994

Related U.S. Application Data

[62] Division of Ser. No. 958,414, Oct. 8, 1992, Pat. No. 5,310,661, which is a division of Ser. No. 744,207, Aug. 12, 1991, Pat. No. 5,215,893, which is a division of Ser. No. 215,466, Jul. 5, 1988, Pat. No. 5,089,396, which is a division of Ser. No. 906,729, Dec. 31, 1986, Pat. No. 4,798,885, which is a continuation-in-part of Ser. No. 827,710, Feb. 7, 1986, abandoned, which is a continuation-in-part of Ser. No. 783,910, Oct. 3, 1985, abandoned.

[51] Int. Cl.$^6$ .......................... C12N 15/16; C12N 15/63; C12N 5/10; C12N 1/21
[52] U.S. Cl. .................. 435/69.4; 435/320.1; 435/240.2; 435/252.3; 435/254.11; 536/23.5
[58] Field of Search ........................ 536/23.5; 435/240.2, 435/320.1, 69.4, 69.5, 254.11, 252.3

[56] References Cited

U.S. PATENT DOCUMENTS

| | | |
|---|---|---|
| 4,409,139 | 10/1983 | Ling et al. |
| 4,624,994 | 11/1986 | Ansel. |
| 4,703,008 | 10/1987 | Lin .......................... 435/240.2 |
| 4,737,578 | 4/1988 | Evans et al. |
| 4,740,587 | 4/1988 | Ling et al. .............. 530/313 |
| 5,004,690 | 4/1991 | Light et al. |
| 5,102,907 | 4/1993 | Dekretser et al. |
| 5,364,837 | 11/1994 | Burger et al. .............. 514/8 |

FOREIGN PATENT DOCUMENTS

| | | |
|---|---|---|
| 0210461 | 2/1987 | European Pat. Off. |
| 61-229826 | 10/1986 | Japan. |
| 62-501680 | 7/1987 | Japan. |
| 63-500309 | 2/1988 | Japan. |
| WO86/0078 | 1/1986 | WIPO. |
| WO86/06076 | 10/1986 | WIPO. |
| WO87/00528 | 1/1987 | WIPO. |

OTHER PUBLICATIONS

Sambrook, J., et al. (1989) Molecular Cloning, 2d ed.; New York: Cold Spring Harbor, Chapter 11.
Maniatis, T., et al. (1982), Molecular Cloning, 1st ed., New York: Cold Spring Harbor; Chapter 12#.
Chem. Abstr., vol. 95 (1981) 21821.
Chem. Abstr., vol. 97 (1982) 66653.
Chem. Abstr., vol. 98 (1983) 28090.
Chem. Abstr., vol. 98 (1983) 28054.
Chem. Abstr., vol. 100 (1984) 80010.
Chem. Abstr., vol. 100 (1984) 132713.
Chem. Abstr., vol. 100 (1984) 151164.
Chem. Abstr., vol. 102 (1985) 56346.
Chem. Abstr., vol. 102 (1985) 56271.
Chem. Abstr., vol. 102 (1985) 198182.
Chem. Abstr., vol. 102 (1985) 40114.
Chem. Abstr., vol. 103 (1985) 98880.
Chem. Abstr., vol. 103 (1985) 65743.
Chem. Abstr., vol. 106 (1987) 79384.
Chem. Abstr., vol. 103 (1985) 2346.
Chem. Abstr., vol. 103 (1985) 116999.
Chem. Abstr., vol. 105 (1986) 863.
Chem. Abstr., vol. 105 (1985) 35841.
Chem. Abstr., vol. 106 (1987) 96422.
Chem. Abstr., vol. 103 (1985) 98855.
Arbatti et al., "Complete amino acid sequence of human seminal plasma β–inhibin", *FEBS Ltrs.* 181(1):57–63 (1985).
Beksac et al., "Evidence for the prostatic origin of immunoreactive inhibin–like material in human seminal plasma", *Int. J. Andrology*, 7:389–397 (1984).
Chu et al., *Nature*, 3:337–340 (1984).
Johansson et al., "Analysis of an inhibin preparation reveals apparent identity between a peptide with inhibin–like activity and a sperm–coating anitgen", *FEBS Ltrs.*, 176(1):21–26 (1984).
Kohan et al., "Peptides of postulated inhibin activity", *FEBS Ltrs.*, 199(2):242–248 (1986).
Krishnan et al., "Comparative Study of Inhibin from Human Testis Prostate and Seminal Plasma", *Andrologia*, 14:409–415 (1982).
Li et al., "Human seminal α inhibins: Isolation, characterization, and structure", *Proc. Natl. Acad. Sci.*, 82:4041–4044 (1985).
Lilja et al., "Amino acid sequence of the predominant basic protein in human seminal plasma", *FEBS Ltrs.*, 182(1):181–184, (1985).
Ling et al., "Pituitary FSH is released by a heterodimer of the β–subunits from the two forms of inhibin", *Nature*, 321:779–782 (1986).
Lugaro et al., "Bovin Seminal Plasma Contains A Low-Molecular-Weight Factor That Inhibits RNA Synthesis", *Arc. Andrology*, 13:261–267 (1984).
Lugaro et al., "Effect of a Seminal Inhibin–Like Factor on In Vivo FSH and LH Uptake by Rat Testis", *Cell Biol. Int. Reports*, 8(10):811 (1984).
Lautenberger et al., *Gene*, 23:75–84 (1983).

(List continued on next page.)

*Primary Examiner*—Stephen G. Walsh
*Assistant Examiner*—David L. Fitzgerald
*Attorney, Agent, or Firm*—Janet E. Hasak

[57] ABSTRACT

DNA encoding the prepro inhibin α and β chains has been isolated. This DNA is ligated into expression vectors and used to transform host cells for the preparation of inhibin or activin. Also provided are prohormone domains and other inhibin α or β chain derivatives having therapeutic or diagnostic interest. The compositions provided herein are useful in the manipulation of fertility in animals.

17 Claims, 24 Drawing Sheets

OTHER PUBLICATIONS

Manjunath et al., "Purification and biochemical characterization of three major acidic proteins ($BSP-A_1$, $BSP-A_2$, and $BSP-A_3$) from bovine seminal plasma", *Biochem. J.*, 241:685–692 (1987).

Mason et al., "Complementary DNA sequences of ovarian follicular fluid inhibin show precursor structure and homology with transforming growth factor–$\beta$", *Nature.* 318:659–663 (1985).

Mayo et al., "Inhibin A–subunit cDNAs from procine ovary and human placenta", *Proc. Natl. Acad. Sci.*, 83:5849–5853 (1986).

Miyamoto et al., "Isolation of Procine Follicular Fluid Inhibin of 32K Daltons", *Biochem. & Biophys. Res. Comm.*, 129(2):396–403 (1985).

Mohapatra et al. "On the identity of bovine seminal plasma inhibin", *Mol. Cell. End.*, 41:187–196, (1985).

Okayama et al., *Molecular and Cellular Biology*, 3:280–289 (1993).

Ramasharma et al., "Isolation, Structure, and Synthesis of a Human Seminal Plasma Peptide with Inhibin–Like Activity", *Science,* 223:1199–1202 (1984).

Ramasharma et al., "Isolation and characterization of Inhibin from Human Seminal Plasma", *Ann. N.Y. Acad. Sci.*, pp. 307–328 (1982).

Ramasharma et al., "Human seminal $\alpha$–inhibins: Detection in human pituitary, hypothalamus, and serum by immunoreactivity", *Proc. Natl. Acad. Sci.*, 83:3484–3486, (1986).

Robertson et al., "Isolation Of Inhibin From Bovine Follicular Fluid", *Biochem. & Biophys. Res. Comm.,* 126(1):220–226 (1985).

Sairam et al., "Isolation and Characterization of a Bovine Seminal Plasma Protein Inhibiting pituitary FSH Secretion", *Mol. Cell. End.,* 22:231–250 (1981).

Seidah et al., "Partial amino acid sequence of a human seminal plasma peptide with inhibin–like activity", *FEBS Ltrs.,* 167(1):98–102 (1984).

Seidah et al., "Complete amino acid sequence of human seminal plsama $\beta$–inhibin", *FEBS Ltrs.,* 175(2):349–355, (1984).

Sheth et al., "Characterization of a polypeptide from human seminal plasma with inhibin (inhibition of FSH secretion) –like activity", *FEBS Ltrs.,* 165(1):11–15 (1984).

Statement of Donald Chism before the Subcommitte e on Intellectual Property and Judicial Administration Comittee on the Judiciary, U.S. House of Representative, Nov. 21, 1991 on H.R. 1417.

Vale et al., "Purification and characterization of FSH releasing protein from porcine ovarian follicular fluid", *Nature,* 321:776–778 (1986).

Ying et al., "Purification of Gonadostatin from Bovine", *Adv. Exp. Med. Biol.,* 147:117–134 (1982).

Fig. 1B-1

```
                                                                                                                            1
                                                                                                                            met trp pro gln leu leu leu leu ala pro
    1    TGTGGGCAGACCCTGACAGAAGGGGCACAGGGCTGGGTGTGGGTTCACCGTTGGCAGGGCCAGGTGAGCT                                               ATG TGG CCT CAG CTG CTC CTG TTG GCC CCA 20                              30                                                 40
         arg ser gly his gly cys gln gly pro glu leu asp arg glu leu val leu ala lys val arg ala                            leu gly pro
  108    CGG AGT GGC CAT GGC TGC CAG GGC CCG GAG CTG GAC CGG GAG CTT GTC CTG GCC AAG GTG AGG GCT                            CTG GGA CCC pro ala val thr gly glu gly gly asp pro gly val arg arg leu pro arg arg                  arg gly                   gly ser glu
                                50                              60                   70
  198    CCG GCA GTG ACT GGG GAA GGT GGG GAT CCT GGA GTC CGT AGG CTG CCC CGA AGA                  AGG GGC                   TCT GAG pro glu glu asp val ser gln his thr his ala ile leu phe pro ala thr gly ala arg           cys gly asp glu pro ala ala gln leu ala arg
                    80                              90                              100
  288    CCC GAG GAG GAT GTC TCC CAG CAC ACA CAC GCC ATC CTT TTC CCG GCT ACA GGT GCC CGC           TGT GGG GAC GAG CCA GCT GCT CAG CTG GCC CGG glu ala gly glu gly leu phe thr tyr val phe ala ala ala asn ser ser arg gln val thr      ser ala leu ser ser arg gly trp phe his
                        110                              120                             130
  378    GAG GCT GAG GGG CTC TTC ACA TAT GTA TTC GCC GCA GCC AAT AGC TCT CGC CAG GTG ACT          TCA GCT CAG CTG TCA TCC AGG TGG TTC CAC thr gly leu asp arg gln met gly gln gln asn ser ser gly pro leu leu leu ala ser ala     leu pro val ala
                            140                             150                              160
  468    ACG GGA CTG GAC AGA CAG ATG GGG CAG CAG AAT AGC AGC GGG CCC CTG CTG CTA TCA GCA          CTG CCT GTG GCT val pro met ser leu gly gln ala pro pro arg trp ala val leu his leu ala ala leu pro     leu thr his pro val leu
                                170                             180                             190
  558    GTG CCC ATG TCA CTG GGC CAG GCG CCC CCT CGC TGG GCT GTG CTG CAC CTG GCC GCC CTC CCT      TTG ACC CAC CCA GTC CTG
```

Fig. 1B-2

```
            200              cys      210                    220
     val leu leu arg pro leu cys ser ala arg pro glu ala thr pro phe leu val ala his thr arg ala arg pro pro
648  GTG CTG CTG CGC CCT CTC TGT TCA GCC CGG CCC GAG GCC ACC CCC TTC CTG GTG GCC CAC ACT CGG GCC AGG CCA CCC α subunit
                              240                             250
     ser gly gly glu arg ala arg ser thr ala pro leu pro trp pro ser pro ala ala leu arg leu leu gln arg pro pro glu
738  AGC GGA GGG GAG AGG GCC CGA AGG TCC ACC GCC CCT CTG CCC TGG CCT TCC CCC GCC GCG CTG CGC CTG CTG CAG AGG CCC CCG GAG 260                          270                                   280
     glu pro ala val his ala asp his arg ala ser leu asn ile ser phe gln glu leu gly trp asp arg trp ile val his pro pro
828  GAA CCC GCT GTG CAC GCC GAC CAC AGA GCT TCC CTC AAC ATC TCC TTC CAG GAG CTG GGC TGG GAC CGG TGG ATC GTG CAC CCT CCC cys       290                         300                                  310
     ser phe ile phe his tyr cys his gly gly cys gly leu pro thr leu pro asn leu pro leu ser val pro gly ala pro thr pro
918  AGT TTC ATC TTC CAC TAC TGT CAC GGC GGG TGC GGG CTG CCC ACC CTG CCC AAC CTG CCC CTG TCT GTC CCT GGG GCC CCC ACC CCT cys cys               320                              330                  340
     val gln pro leu leu val pro gly ala gln pro cys cys ala ala leu pro gly thr met arg ser leu arg val arg thr thr ser
1008 GTC CAG CCC CTG TTG GTG CCA CAG GCT TGC TGC GCT GCT CTC CCG GGG ACC ATG AGG TCC CTA AGG GTT CGC GTT CGC ACC ACC TCG cys      360         cys     ile OC
     asp gly tyr ser phe lys gln thr val pro asn leu leu thr gln his cys ala 364
1098 GAT GGA GGT TAC TCT TTC AAG ACG GTG CCC AAC CTT CTC ACC CAG CAC TGT GCC ATC TAA GGGTGTCCCGCTGGTGCCGAGCTCCC 1194 ACAGGCACCAGCCTGGAGGAAGGCAGAGTTCCCACTCCCCCTTCTTCCGCCTCCTCCGCCTGGAGGCTCCCCCCTGTCCGCCCTGTCCCATGGTAATGTGACAATAAACAGCAT

1312 AGTGCAGATGACTCGGTGCGCAAAAAAAA
```

Fig.2B-1

```
1   AAAAGGGCCGTCACCACAACTTTGGCTGCCAGG 1                                              10                                                  20
                                                                 met pro leu leu trp leu arg gly phe leu leu ala ser cys trp ile ile val arg ser ser
                                                                 ATG CCC TTG CTT TGG CTT AGA GGA TTT TTG CTT GCG AGT TGC TGG ATT ATA GTG AGG AGT TCC 30                                                                                          40                                                           50
     pro thr pro gly ser gly gly his ser ala ala pro asp cys pro ser  ala thr leu pro lys asp val pro asn ser gln
97   CCC ACC CCA GGA TCC GGG GGA CAC AGC GCA GCC CCG GAC TGC CCG TCC  GCG ACC CTC CCA AAG GAG GTA CCC AAC TCT CAG
                                                                      CGG CTG GCG GCG CGA CTG
                                                                      arg leu ala ala arg leu 90
     pro glu met val glu ala val lys his ile leu asn met leu his leu val gly lys val  asp pro   thr gln pro val ala
187  CCG GAG ATG GTG GAA GCC GTC CAC ATT CTC AAC ATG CTG CAT TTG GTG GGC AAA GTG  CAG CCG  ACC CAG CCG GTA GCG
     GGC GAC TTC CTG GAG GCG CAC ATC ATC TTG CAC ATG CGC CTA CTG GTG GGC AAG GTG  GAT GTC  ACC CAT CCC GTG GCG
     gly asp phe leu glu ala his ile ile leu his met arg leu leu val gly lys val  asp val  thr his pro val ala 100                                                         130
     ala leu asn ala ile arg lys lys gly met glu asn glu asp gly lys val tyr    gly      leu glu asp asp his leu asp ile gly  thr ala                                phe
277  GCG CTT AAC GCG ATC AGA AAG AAG GGC ATG GAA AAC GAA GAC GGC AAA GTG TAC    GGG      CTG GAG GAC GAC CAC CTG GAT ATC GGG  ACC GCC                                TTT
     ATG GTC ACG CTG CGC AAA AAG GGC ATG GAG GAG GAG GAG GAC AAG AAG GTG TAT    GGT      CTG GTG GAG GAC CGC CTG CTG GAT ATT  GGC GCC --- TCC                        TTC
     met val thr leu arg lys lys gly met glu glu glu glu asp lys lys val tyr    gly      leu val glu asp arg leu leu asp ile  gly ala     ser  ser   arg ala his ala phe glu met asn glu leu met gln leu thr gln glu ile ile thr ser glu glu ala    thr ala
367  GAA ATG AAT GAA CTC ATG CAA CTG ACC CAG GAG ATC ATC ACC TCG GAG GAA GCA    ACC GCC
     CCT GGC GAC GAC GGC CAA GGC GAG ACA GAT --- --- AGC CTC TCC GAG GCA GAG    CTG GCC
     pro gly ala asp gly gln gly glu thr asp             ser leu ser glu ala glu leu ala
```

```
1360  GAAGACACGTTTACGGCCTCTGACCTAGGCGACCGGCAAACATGAAATGAACACAGATGAAGGAAGACGTGGAAAAATTCCGTAGCC
      TGTGGTCTTGCCGCTGGGTGGCCGGCCCGGCCAGGTGGCCAGGTGCCAGGTGGAGGCCTGAGATACTTTCCTACTTCTTTATTGAGCAATCAGTCGAAACCAGAGGGCGGACCCTCCGTGGACACGAAAGA

1480  AGGGCTCGGCGATGACACCGTGAAGGAGACGGGACTCGGGGGGAGGGCAGAACGGGACTGGGGGCGGGGGACGAGCAGAACGGCTTCTTCCTCCAGCATCGGAGTGGGGAC
      CTTGAAAATGCACACGTAGATGCCCGAGCAGACGCCTCCTGCCACCCACAGACGCCTCCGGATACCAGCAAATGGATGCAGCTTAGCTACAAACGCTGTCAG

1600  AGCAGTTGCTCCAACGGGAATATTGTCCTCTCCTTTTCAGTTCCCTGTGTCAGTGTGAGCCTCGAAGTCAGCTTGTCTGCTCGAGCCATGTGGGCTGGCACAACCCAAATAGCGTCTAGA
      TCGGAGAGAAAGGGTGAGCAGCCACCATTCCCACACGCTGGCCCACCTGAATGCTCCTTTCGAGCACACAGAAAAGACACAGAGAGACACCGAGAGAGAGAGAGAGAGAGAGAGAGA

1720  AAGCCATGAGTTTGAAAGGGCCAGTTATAGGCACTTTCCCACCAGGTCTAACCCAGTCGTAAGGTATGTCTGTGTGACCCTCTCTCTGTATATCAGCCCATGCACACACTTACAAAGAC
      GAGACAGAGACAGAGAGAGAGACAGAGCGAGAGAGAGAGAGAGAGAGAGAG

1840  ACACACACACACACACACACACACACACACACACACACACACACACACACACACACACACACACAAACTTCCTCTGACTTTTCTGAGACAAAGAGGTGGGTATAAACTGACTCAGGAAAACTCGAG
1960  TGGAAAACGTGCCCTTTGGGTTGGGACAATTTAGATGGTGGAGCAAAGCAAACGGCAAGTGTTCGTGACTCAAGAGGAGCAACGGCAAGTAATTCAGTCGGTTAGGGAGCCTGTGCCCTGAGGGAGGGGTGAGGAAGTCCCTA
2080  AGGGTGACCTTAGCCAGAACGTGACTCTAGAAGGGGCTCGACAGGTCGACAGGGTCATGTAAAGAGAGAGAGGAGCAACGGTCAATTCAGTGGGTTAACGTCATCCGGCTGGTGCAGGTTGCAGACG
2200  TCGTGGCAGTGGTTAACGAATCGAATCGAGGTTGGACCATGAGGTTCGACTTGAGGGTCGATCCGTAACGATCCGGCGTTCCGCCCAAGAAATAGCAAAAAAGAGGCAGAGGGACGTC
2320  CGGCTCGAGATCGCTGCGTGTGCGTAGGCGGTCCCTTTAACCCAAGTAGGAGGAAGGGAATGAGAGACTAAGAAGTGAATTTCTTGACAGTGGGAGCATGGAGGCATGTATTCCACCTTTCGCTTTCAGTGTATCTTGTT
2440  AGAACCACCGTGGAGGCCCGTAGGCAAGGCGGCCCCCCTCCGTAGGCTGCACAGGAGTTCGCTGCAAGAGAGTTCGCTCAAGAATCATGAATTATCTCAGGGCCACGGTGGGACACTTAATCAACCCTACAGTTGTTTCACGTGTATCTTGTT
2560  AGTGCCTCTTCCTGGAGGCGGCCTAAGGGCTCCATTCAGTCCCGTGTATTGCTCCCGTATTGCTCCCGTATTGCTCCAAGCCAAAGCTGTGCTCCCTAAATATCTGGAAGCCATCTTTTCCCAAGCTGTCATCACCGCTTGTCCAGCTGCTCTTCCTCGCCAGGTCTC
2680  TCTGAAGTCACGGCGAGACTAAGGCTTCAGTCCGTGTATTGCTCCCGTATTGCTCCCGTATTGCTCCCTAAATATCTGGAAGCCATCTTTTCCCAAGCTGTCATCACCGCTTGTCCAGCTGCTCTTCCTCGCCAGGTCTC
2800  TGCTGGTTAAACCCTACACTATTTGAGAACCAAAGCTGTCTGTCCCCTAAATATCTGGAAGCCATCTTTTCCCAAGCTGTCATCACCGCTTGTCCAGCTGCTCTTCCTCGCCAGGTCTC
2920  ATTCCTCCTGCCCAGTCACTCTCCACACAGCCAAAGCTGTCTGTCCCCTAAATATCTGGAAGCCATCTTTTCCCAAGCTGTCATCACCGCTTGTCCAGCTGCTCTTCCTCGCCAGGTCTC
3040  CCATCCCCTTCCTCGTCCTCCACACAGCCGCGTACCATGCAGCCTGTACCAAAGCTGTACCTTTTAATCCTAAATGTTTCTTCCTCGGGAGACCTTTCTGATTTGTGATGTAGGTCAAGACTTTAGTTAGTTAAATCTCTTAGCACCA
3160  AATTCAAAGAGCTTGTAACACTCCCATTTCCACCTTTTAATCCTAAATGTTTCTTCCTCGGGAGACCTTTCTGATTTGTGATGTAGGTCAAGACTTTAGTTAGTTAAATCTCTTAGCACCA
3280  TCTCCGCTTGTAACACTCCCATTTCCACCTTTTAATCCTAAATGTTTCTTCCTCGGGAGACCTTTCTGATTTGTGATGTAGGTCAAGACTTTAGTTAGTTAAATCTCTTAGCACCA
3400  TGCCTGTTTCATGACGTGCGGGCACACAGTTGTTGCTCAATAAATTTGCTCAATAAATTTGACTTAATGAACTCAAAAAAAAAAAAAAA
3520  ATTCCCAGTGTCGGGCACACAGTTGTTGCTCAATAAATTTGCTCAATAAATTTGACTTAATGAACTCAAAAAAAAAAAAAAA
```

Fig. 4A.

```
p.βA-Inh:  GLE----CDGKVNI-CCKKQFFVSF-KDIGWNDWIIAPSGY
           *           *   **       *
h.β-TGF:   ALDTNYCFSSTEKNCCVRQLYIDFRKDLGWK-WIHEPKGY
p.βB-Inh:  GLE----CDGRINL-CCRQQFFIDFRL-IGWSDWIIAPTGY
           *           *   *         * p.βA-Inh:  HANYCEGECPSHIAGTSGSSLSFHSTVINHYRMRGHSPFA
                *   *                  *
h.β-TGF:   HANFCLGPCPYIWSLDT---QYSKVLAL-YNQ--HNPGA
p.βB-Inh:  YGNYCEGSCPAYLAGVPGSASSFHTAVVNQYRMRGLNPG-
               *   *                  * p.βA-Inh:  NLKSCCVPTKLRPMSMLYYDDGQNIIKKDIQNMIVEECGCS
               **     *       *             **
h.β-TGF:   SAAPCCVPQALEPLPIVYYV-GRKPKVEQLSNMIVRSCKCS
p.βB-Inh:  TVNSCCIPTKLSTMSMLYFDDEYNIVKRDVPNMIVEECGCA
               **     *              *      **
``` p.βA-Inh:
h.β-TGF:
p.βB-Inh:

Fig. 4B.

```
         1                                                                              39
p.βA-Inh: GLECDGK VNI - C KKQFFV SF KDI GWND WIIA PSGYHANY
p.α -Inh: RPPEEPA V HAD C HRASLNIS F QELGWDR WIVH PSFIFHY
               *           *           ***       *
          19                                                                            58

40                                                                             79
p.βA-Inh:  C EGE C PSHIAGTSGS S LSFHSTVINHYRMRGHSPFANLKS
p.α -Inh:  C HG G  GLPTLPNLPL S VPGAPPTPVQPLLLVPGAQ----P
             *                 *
          59                                                                            94

80                                                                             116
p.βA-Inh:  C  VPTKLRPM S MLYY--DDGQ-NIIKKDIQ NMIVEE GG C S
p.α -Inh:  C AALPGTMR S LRVRTTSDGGYSFKYETVPN LLTQH GA C I
             *         *                              **
          95                                                                            134
```

Fig. 6A.

```
                                                    -10                                      -1 +1
    -16 Gly Val Ser Ser Gln Gly Leu Val Leu Arg Glu Leu Ala Arg Ala Leu  Lys Val Arg Ala Leu Phe Leu Asp
  1 GT  GGG GTC AGC AGC CAG GGG CTG GTT CTT GAG CTG GCC CGG GCC CTG      AAG GTG AGG GCC CTG TTC TTG GAT
                                                                                          30
        Ala Leu Gly Pro Pro Ala Val Thr Arg Glu Gly Gly Asp Pro Gly  Val Arg Arg Leu Pro Arg Arg His Ala Leu
 75     GCC TTG GGG CCC CCC GCG GTG ACC AGG GAA GGT GAC CCT GGA GTC  AGG CGG CTG CCC CGA AGA CAT GCC CTG
                                    40                                              50
        Gly Gly Phe Thr His Arg Gly Ser Glu Pro Glu Glu Glu Asp Val  Ser Gln Ala Ile Leu Phe Pro Ala Thr
150     GGG GGC TTC ACA CAC AGG GGC TCT GAG CCC GAG GAA GAG GAT GTC  TCC CAA GCC ATC CTT TTC CCA GCC ACA
                      60                                         70                              80
        Asp Ala Ser Cys Glu Asp Lys Ser Ala Ala Arg Gly Leu Ala Gln  Glu Gly Leu Phe Arg Tyr Met
225     GAT GCC AGC TGT GAG GAC AAG TCA GCT GCC AGA GGG CTG GCC CAG  GAG GGC CTC TTC AGA TAC ATG
                                          90                                                      100
        Phe Arg Pro Ser Gln His Thr Arg Ser Asn Ser Glu Ser Arg Gln Val Thr Ser Ala Gln Leu Trp Phe His Thr Gly Leu Asp Arg
300     TTC CGG CCA TCC CAG CAT ACA CGC AGC AAT AGC TCT GAG AGC CGC CAG GTG ACT TCA GCC CAG CTG TGG TTC CAC ACC GGG CTG GAC AGG
                              110                                                      120
        Gln Gly Thr Ala Ala Ala Ser Ala Pro Pro His Trp Ala Val Leu  His Ala Leu Ser Pro Gly Pro Val Ala
375     CAG GGC ACA GCA GCC TCC GCA CCT CCT CAC TGG GCC GTG CTG       CAC GCC CTG TCA CCG GGA CCC GTG GCT
                                      130                                                  150
        Val Pro Met Ser Leu Gly His Ala Pro Leu Leu Gly Val Leu His  Ala Thr Ser Ala Leu Ser Leu Leu
450     GTG CCC ATG TCT TTG GGC CAT GCT CCT CTC CTG GGC GTG CTG CAC  GCC ACC TCT GCT CTC TCT CTG CTG
                          160                                   170                               180
        Thr His Pro Val Leu Val Leu Leu Leu Arg Cys Pro Leu Cys Thr  Ser Ala Arg Pro Glu Ala Thr Pro Phe
525     ACC CAC CCC GTC CTG GTG CTG CTG CTG CGC TGT CCC CTC TGT ACC  TCA GCC CGG CCT GAG GCC ACG CCC TTC
```

Fig. 6B.

→ α subunit

```
       Leu Val Ala His Thr Arg Pro Pro Ser Gly Glu Arg Ala Arg Ser Thr Pro Leu Met Ser Trp
                          190
600    CTG GTG GCC CAC ACT CGG AGA CCA CCC AGT GGA GAG AGA GCC CGA TCA ACT CCC CTG ATG TCC TGG
                                                                                            230
       Pro Trp Ser Pro Ser Ala Leu Arg Leu Leu Gln Arg Pro Pro Glu Glu Pro Ala Ala His Ala Asn His Arg
       210                              220
675    CCT TGG TCT CCC TCT GCT CTG CGC CTG CTG CAG AGG CCT CCG GAG GAA CCG GCT GCC CAT GCC AAC CAC AGA

Val Ala Leu Asn Ile Ser Phe Gln Glu Leu Gly Trp Glu Arg Trp Ile Val Tyr Pro Pro Ser Phe Ile Phe His
                 240                                                250
750    GTA GCA CTG AAC ATC TCC TTC CAG GAG CTG GGC TGG GAA CGG TGG ATC GTG TAC CCT CCC AGT TTC ATC TTC CAC

Tyr Cys His Gly Gly Leu His Ile Pro Gly Ala Gln Pro Cys Cys Ala Ala Leu Pro Val Pro Gly Ala Pro Thr Pro
       260            270                                 280
825    TAC TGT CAT GGT GGG CTG CAC ATC CCA GGG GCC CAG CCC TGC TGT GCT GCT CTC CCT GTC CCT GGG GCT CCC ACC CCA

Ala Gln Pro Tyr Ser Leu Pro Gly Gly Tyr Ser Phe Lys Tyr Glu Thr Val Pro Asn Leu Leu Thr Met Arg Pro Leu His
                          290                                       300
900    GCC CAG CCC TAC TCC TTG CCA GGG GGT TAC TCT TTC AAG TAT GAG ACA GTG CCC AAC CTT CTC ACG ATG AGG CCC CTA CAT

Val Arg Thr Thr Thr Ser Asp Gly Gly Tyr Ser Phe Lys Tyr Glu Thr Val Pro Asn Leu Leu Thr Arg Pro Leu His Cys Ala
       310                              320                                                                          330
975    GTC CGC ACC ACC ACC TCG GAT GGA GGT TAC TCT TTC AAG TAT GAG ACA GTG CCC AAC CTT CTC ACG CAG CAC TGT GCT

Cys Ile OC*
       335
1050   TGT ATC TAA   GGGTGGGGGGTCTTCCTTCTTAATCCCATGGCTGGTGGCCACGCCCCACCATCATCAGCTGGGAGGAAAGGCAGAGTTGGGAAATA

1146   GATGGCTCCCACTCCTCCCCTCCTTCACTTCTCTGCCTATGGGCTACCCTCCCCACCCACTTCTATCTCAATAAAGAACACAGTGCATATG polyA
```

Fig. 7A.

```
                         -30                                         +1
pin.alpha    MWPQLLLLLLLAPRSGHGCQGPELDRELVLAKVRALFLDALGPPAVTGEGG
hin.alpha                      GVSSQGLELARELVLAKVRALFLDALGPPAVTREGG
                               ***                              *

40                              60
pin.alpha    DPGVRRLPRRHAVGGFMRRGSEPEEE-DVSQAILFPATGARCGDEPAAGE
hin.alpha    DPGVRRLPRRHALGGFTHRGSEPEEEEDVSQAILFPATDASCEDKSAARG
                        *    **        *           *  *  ****  **

80                                         100
pin.alpha    LAREAEEGLFTYVFRPSQHTHSRQVTSAQLWFHTGLDRQGMAAANSSGPL
hin.alpha    LAQEAEEGLFRYMFRPSQHTRSRQVTSAQLWFHTGLDRQGTAASNSSEPL
               *       * *        *                    *  *   *

120                        140                        160
pin.alpha    LDLLALSSRGPVAVPMSLGQAPPRWAVLHLAASALPLLTHPVLVLLLRCP
hin.alpha    LGLLALSPGGPVAVPMSLGHAPPHWAVLHLATSALSLLTHPVLVLLLRCP
              *     * *         *   *       * *  *
```

Fig. 7B.

```
                    180                        200
pin.alpha  LCSCSARPEATPFLVAHTRARPPSGGERARRSTAPLP-WPWSPAALRLLQ
hin.alpha  LCTCSARPEATPFLVAHTRTRPPSGGERARRST-PLMSWPWSPSALRLLQ
           *                                *      **     *

220                        240                260
pin.alpha  RPPEEPAVHADCHRASLNISFQELGWDRWIVHPPSFIFHYCHGGCGLPTL
hin.alpha  RPPEEPAAHANCHRVALNISFQELGWERWIVYPPSFIFHYCHGGCGLHIP
                *   **             *   *                    ***

280                        300
pin.alpha  PNLPLSVPGAPPTPVQPLLLVPGAQPCCAALPGTMRSLRVRTTSDGGYSF
hin.alpha  PNLSLPVPGAPPTPAQPYSLLPGAQPCCAALPGTMRPLHVRTTSDGGYSF
              *         *   **                  *  *

320    334
pin.alpha  KYETVPNLLTQHCACI
hin.alpha  KYETVPNLLTQHCACI
```

Fig. 8A.

```
1   TGCTCCCTGACAGCCACAAACCTACAGCACTGACTGCATTCAGAGAGAACTTTTGTTCTTGTTCCAGAGAATT

101 TGCTGAAGAGGAGAAGAAATAAAAAAAATCCACACACACAAAAAACCTGCGCGTGAGGGGGAGGAAAAGCAGGGCCT

-28  Met Pro Leu Leu Trp Leu Arg Gly Phe Leu Leu Ala Ser Cys Trp
201 TTTAAAAAGGCAATCACAACTTTTGCTGCCAGG                 ATG CCC TTG CTT TGG CTG AGA GGA TTT CTG CTG GCA AGT TGC TGG
                                                                                                                    -20
                                                                                                    -10
    Ile Ile Val Arg Ser Ser Pro Thr Pro Gly Ser Glu His Ser Ala Ala Pro Asp Cys Pro Ser Ala Leu
282 ATT ATA GTG AGG AGT AGT CCC ACC CCA GGA TCC GAG CAC AGC GCG GCC CCC GAC TGT CCC TCC GCG CTG
                                                                      -1  +1
                                                                                               10
                                                                                      30
    Ala Ala Leu Pro Lys Asp Val Pro Asn Ser Gln Pro Glu Met Val Lys Lys His Ile Leu Asn Met
357 GCC GCC CTC CCA AAG GAT GTA CCC AAC TCT CAG CCA GAG ATG GTG AAG AAG CAC ATT TTA AAC ATG
                                20
                                                                                        60
    Leu His Leu Lys Lys Arg Pro Asp Val Thr Gln Pro Val Glu Ile Glu Asp Asp Ile Gly Arg Arg Ala Ile Glu Arg Lys Leu
432 CTG CAC TTG AAG AAG AGA CCC GAT GTC ACC CAG CCG GTA GAG ATA GAG GAT GAT ATT GGA AGG AGG GCA ATC AGA AAG CTT
                                40
                                                                                                            80
    His Val Gly Lys Val Gly Asn Gly Tyr Val Glu Ile Thr Phe Ala Glu Ser Gly Thr Ala Arg Lys Thr Leu His Phe Glu Ile
507 CAT GTG GGC AAA GTC GGG GAG AAC GGG TAT GTG GAG ATA ACG TTT GCC GAG TCA GGA ACA GCC AGG AAG ACG CTG CAC TTC GAG ATT
                                70
                                                                                                                110
    Leu Met Glu Gln Thr Ser Glu Ile Ile Thr Phe Ala Glu Ser Gly Thr Ala Arg Lys Thr Leu His Phe Glu Ile
582 CTT ATG GAG CAG ACC TCG GAG ATC ATC ACG TTT GCC GAG TCA GGA ACA GCC AGG AAG ACG CTG CAC TTC GAG ATT
                                90
```

Fig. 8B.

```
                    Ser Lys Glu Gly Ser Asp Leu Ser Val Val Glu Arg Ala Glu Val Trp Leu Phe Leu Lys Val Pro Lys Ala Asn
                                                120                                 130                                 
657                 TCC AAG GAA GGC AGT GAC CTG TCA GTG GTG GAG CGT GCA GAA GTC TGG CTC TTC CTA AAA GTC CCC AAG GCC AAC
        140                                                         150                                                 160
        Arg Thr Lys Val Thr Ile Arg Leu Phe Gln Gln Lys His Pro Gln Gly Ser Leu Asp Thr Gly Glu
732     AGG ACC AAA GTC ACC ATC CGC CTC TTC CAG CAG AAG CAC CCG CAG GGC AGC TTG GAC ACA GGG GAA
        Glu Ala Glu Glu Val Gly Leu Lys Gly Arg Ser Glu Leu Leu Ser Glu Lys Val Val Asp Ala Arg Lys
                                        170                                         180                                 210
807     GAG GCA GAG GAA GTG GGC TTA AAG GGG AGG AGT GAA CTG CTC TCT GAA AAA GTA GTA GAC GCT CGG AAG
        Ser Thr Trp His Val Phe Pro Val Ser Ser Ile Gln Arg Leu Leu Val Leu Leu Asp Gly Lys Ser Ser Leu Asp Val
                190                                         200                                 
882     AGC ACC TGG CAT GTC TTC CCT GTC TCC AGC ATC CAG CGG TTG CTG GTT CTC CTG GAC GGC AAG AGC TCC CTG GAC GTT
        Arg Ile Ala Cys Glu Gln Ser Gly Ala Ser Leu Gly Lys Gly Lys Lys Lys Lys Glu Glu
                            220                                 230                                 
957     CGG ATT GCC TGC GAG CAG AGT GGC GCC AGC TTG GGC AAG GGG AAG AAG AAG AAG GAG GAA
        Glu Gly Glu Gly Lys Gly Gly Lys Gly Gly Ala Gly Asp Glu Glu Lys Glu Gln Ser His Arg
                            240                                 250                                 260
1032    GAG GGG GAA GGG AAA GGG GGA GGT GGG GCA GAT GAG GAG AAG GAG CAG TCG CAC AGA
```

Fig.8C.

→ β_A subunit

```
        Pro Phe Leu Met Leu Gln Ala Arg Gln Ser Glu Asp His Pro Arg Arg Arg Arg Gly Leu Glu Cys Asp
1107    CCT TTC CTC ATG CTG CAG GCC CGG CAG TCT GAA GAC CAC CCT CGC CGG CGG CGT GGC TTG GAG TGT GAT
                                    270                                 310
        Gly Lys Val Asn Ile Cys Cys Lys Lys Gln Phe Phe Val Ser Phe Lys Asp Ile Gly Trp Asn Asp Trp Ile Ile
1182    GGC AAG GTC AAC ATC TGC TGT AAA CAG CAG TTC TTT GTC AGT TTC AAG GAC ATC GGC TGG AAT GAC TGG ATC ATT
            290                                         300
        Ala Pro Ser Gly Tyr His Ala Asn Tyr Cys Glu Gly Glu Cys Pro Ser His Ile Ala Gly Thr Ser Gly Ser Ser
1257    GCT CCC TCT GGC TAT CAT GCC AAC TAC TGC GAG GGT GAG TGC CCG AGC CAT ATA GCA GGC ACG TCC GGG TCC TCA
                                320                             330
        Leu Ser Phe His Ser Thr Val Ile Asn His Tyr Arg Met Arg Gly His Ser Pro Phe Ala Asn Leu Lys Ser Cys
1332    CTG TCC TTC CAC TCA ACA GTC ATC AAC CAC TAC CGC ATG CGG GGC CAT AGC CCC TTT GCC AAC CTC AAA TCG TGC
            340                                         350                                     360
        Cys Val Pro Thr Lys Leu Arg Pro Met Ser Met Leu Tyr Tyr Asp Asp Gly Gln Asn Ile Ile Lys Lys Asp Ile
1407    TGT GTG CCC ACC AAG CTG AGA CCC ATG TCC ATG TTG TAC TAT GAT GAT GGT CAA AAC ATC ATC AAA AAG GAC ATT
                            370                                         380
        Gln Asn Met Ile Val Glu Glu Glu Glu Gly Cys Gly Ser AM*
1482    CAG AAC ATG ATC GTG GAG GAG GAG GAG GGG TGT GGA TCA TAG AGTTGCCCAGCCCAGGGGAAAGGGAGCAAGAGTTGTCCAGAGAAGACAGTG
             390                           398

1570    GCAAAATGAAGAAATTTTAAGGTTTCTGAGTTAACCAGAAAAATAGAAATTAAAAACAAAACA polyA
```

Fig. 9A.

```
                          7                         10                                              20                                      30
     1 CC  Thr Ser Cys Gly Gly Phe Arg Arg Pro Glu Glu Leu Gly Arg Val Asp Gly Phe Leu Glu Ala Val
           ACG TCG TGC GGC GGC TTC CGG CGG CCA GAG GAG CTC GGC CGA GTG GAC GGC TTC CTG GAG GCG GTG 40                                             50
    75 Lys Arg His Ile Leu Ser Arg Leu Gln Met Arg Gly Arg Pro Asn Ile Thr His Ala Val Pro Lys Ala Ala Met
       AAG CGG CAC ATC TTG AGC CGC CTG CAG ATG CGG GGC CGG CCC AAC ATC ACG CAC GCC GTG CCT AAG GCC GCC ATG 60                                                70                                                80
   150 Val Thr Ala Leu Arg Lys Leu His Ala Gly Lys Val Arg Gly Asp Gly Ile Ile Pro His Leu Asp Gly
       GTC ACG GCC CTG CGC AAG CTG CAC GCG GGC AAG GTG CGC GGC GAC GGC ATC ATC CCG CAC CTC GAC GGC 90                                            100                                           110
   225 His Ala Ser Pro Gly Ala Asp Gly Gln Glu Arg Val Ser Phe Ile Ser Asn Gln Asn Leu Phe Val Gln Ala Ser Leu
       CAC GCC AGC CCG GGC GCC GAC GGC CAG GAG CGC GTT TCC TTC ATC AGC AAC CAG AAC CTG TTT GTG CAG GCC CTG 120                                               130
   300 Ser Ser Arg Val Arg Leu Tyr Phe Phe Ile Ser Lys Gly Ser Arg Arg Lys Val Arg Val Lys Val Tyr Phe
       TCC TCC CGG GTC CGC CTA TAC TTC TTC ATC TCC AAA GGC AGC CGG CGG AAG GTG CGG GTC AAA GTG TAC TTC 140                                              150                                               160
   375 Trp Leu Tyr Leu Lys Leu Leu Pro Tyr Val Leu Glu Lys Gly Ser Arg Arg Lys Val Arg Val Lys Val Tyr Phe
       TGG CTT TAC CTG AAA CTC CTG CCC TAC GTG CTG GAG AAG GGC AGC CGG CGG AAG GTG CGG GTC AAA GTG TAC TTC 170                                             180
   450 Gln Glu Gln Gly His Gly Asp Arg Trp Asn Met Val Glu Lys Arg Val Asp Leu Lys Arg Ser Gly Trp His Thr
       CAG GAG CAG GGC CAC GGT GAC AGG TGG AAC ATG GTG GAG AAG AGG GTG GAC CTC AAG CGC AGC GGC TGG CAT ACC
```

Fig. 9B.

```
                                                                                          190
         Phe Pro Leu Thr Glu Ala Ile Gln Ala Leu Phe Glu Arg Gly Glu Arg Arg Leu Asn Leu Asp Val Gln Cys Asp
    525  TTC CCA CTC ACG GAG GCC ATC CAG GCC TTG TTT GAG CGG GGC GAG CGG CGA CTC AAC CTA GAC GTG CAG TGT GAC
                                       210                                            220                              230
         Ser Cys Gln Glu Leu Ala Val Val Pro Val Phe Val Asp Pro Gly Glu Glu Ser His Arg Pro Phe Val Val Val
    600  AGC TGC CAG GAG CTG GCC GTG GTG CCG GTG TTC GTG GAC CCA GGC GAA GAG TCG CAC CGG CCC TTT GTG GTG GTG
                                                                            240                              β_B subunit
         Gln Ala Arg Leu Gly Asp Ser Arg His Arg Ile Phe Arg Lys Arg Gly Asp Cys Leu Glu Asp Gly Arg Thr Asn Leu Cys
    675  CAG GCT CGG CTG GGC GAC AGC AGG CAC CGC ATT CGC AAG CGA GGC GAT TGC CTG GAG GGC CGG ACC AAC CTC TGT
                                       260                                            270                              280
         Cys Arg Gln Gln Phe Phe Ile Asp Phe Arg Leu Ile Gly Trp Asn Asp Trp Ile Ile Ala Pro Thr Gly Tyr Tyr
    750  TGC AGG CAA CAG TTC TTT ATT GAC TTC CGC CTC ATC GGC TGG AAC GAC TGG ATC ATA GCA CCC ACC GGC TAC TAC
                                       290                                            300
         Gly Asn Tyr Cys Glu Gly Ser Cys Pro Ala Tyr Leu Ala Gly Val Pro Gly Ser Ala Ser Ser Phe His Thr Ala
    825  GGG AAC TAC TGT GAG GGC AGC TGC CCA GCC TAC CTG GCA GGG GTC CCC GGC TCT GCC TCC TCC TTC CAC ACG GCT
                                       310                                            320                              330
         Val Val Asn Gln Tyr Arg Met Arg Gly Leu Asn Pro Gly Thr Val Asn Ser Cys Cys Ile Pro Thr Lys Leu Ser
    900  GTG GTG AAC CAG TAC CGG ATG CGG GGT CTG AAC CCC GGC ACG GTG AAC TCC TGC TGC ATT CCC ACC AAG CTG AGC
                                       340                                            350
         Thr Met Ser Met Leu Tyr Phe Asp Asp Glu Tyr Asn Ile Val Lys Arg Asp Val Pro Asn Met Ile Val Glu Glu
    975  ACC ATG TCC ATG CTG TAC TTC GAT GAT GAG TAC AAC ATC GTC AAG CGG GAC GTG CCC AAC ATG ATT GTG GAG GAG
```

Fig. 9C.

```
           359
      Gly  Cys  Ala  OP*
1050  GGC  TGC  GCC  TGA  CAGTGCAAGGCAGGGGCAGGGGCACGGTGGTGGGGCACGGAGGGCAGTCCCCGGGTGGCTTCTTCCAGCCCCGCGGGAACGGGGT
1145  ACACGGTGGGCTGAGTACAGTCATTCTGTTGGGCTGTGTGGAGATAGTGCCAGGGTGCGGCCTGAGATATTTTCTACAGCTTCATAGAGCAACCAGTCAAA
1245  ACCAGAGCGAGAACCCTCAACTGACATGAAATACTTTAAAATGCACACGTAGCCACGCAGCCAGCAGCCTCCAGGA
1345  TACCAGCAAATGGATGCGGTGACAAATGCAGCTTAGCTACAAATGCCTGTCAGTGGAGAGAATGGGGTGAGCAGCCACCATTCCACCAGCTGGCCCGG
1445  CCACGTCTCGAAGTTGCGCAGCTCGGCGGGAGCCTGTCCTTCCCGAGCACAGAGACGCAGAGAGACGCCACGGAGAGAGCCACGGAGGAAAAGCAGATGCAGG
1545  GTGGGAGCGCAGCCTGGGAGCCTGTGGCTTCTCCCGTGCCGGCTTTTACCAGCCTGCCCGTGCCCTGTCTGCTCTGATGTCTGTTCTTCCCAGCCTGGGATCCTT
1645  CGTGCTTCAAGGCCTGGGGACCTGTGTTTGGGCTGTGTGGGAGGCGTCACAACCCGTGGGAGACCTGGGAGCAGGGCAAT
1745  GACCGTTTAACTGACTGTTCCAACAGTTGACAGGTCATCCTTGCCAGTTGTATAACTGAAAAGGACTTTTCTACCAGGTATGACCTTTAAGTGAAATCTGAA
1845  GCTTTAACTGATCTCCAACAGTTGACAGGTCATCCTTGCCAGTTGTATAACTGAAAAGGACTTTTCTACCAGGTATGACCTTTAAGTGAAATCTGAA
1945  TTGTTCTAAATGAAAAGAAAAA
```

NUCLEIC ACID ENCODING THE MATURE α CHAIN OF INHIBIN AND METHOD FOR SYNTHESIZING POLYPEPTIDES USING SUCH NUCLEIC ACID

This is a divisional application of U.S. Ser. No. 07/958,414 filed Oct. 8, 1992, now U.S. Pat. No. 5,310,661, which is a divisional application of U.S. Ser. No. 07/744,207 filed Aug. 12, 1991, now U.S. Pat. No. 5,215,893, which is a divisional application of U.S. Ser. No. 07/215,466 filed Jul. 5, 1988, now U.S. Pat. No. 5,089,396, which is a divisional application of U.S. Ser. No. 06/906,729 filed Dec. 31, 1986, now U.S. Pat. No. 4,798,885, which is a continuation-in-part application of U.S. Ser. No. 06/827,710 filed Feb. 7, 1986, now abandoned, which is a continuation-in-part application of U.S. Ser. No. 06/783,910 filed Oct. 3, 1985, now abandoned.

BACKGROUND

This invention related to methods for making proteins in recombinant cell culture which contain the α or β chains of inhibin. In particular, it relates to methods for obtaining and using DNA which encodes inhibin, and for making inhibin variants that depart from the amino acid sequence of natural animal or human inhibins and the naturally-occurring alleles thereof.

Inhibin is a protein produced in the gonad which acts specifically at the pituitary level to inhibit the secretion of follicle-stimulating hormone (FSH). The existence of inhibin was first postulated by McCullagh in 1932 ("Science" 76: 19–20). Such preferential regulation of the gonadotropin secretion has generated a great deal of interest and has prompted many laboratories in the past fifty years to attempt to isolate and characterize this substance from extracts of testis, spermatozoa, rete testis fluid, seminal plasma and ovarian follicular fluid, using various bioassays. Although many reports have appeared in the literature claiming the purification of inhibin-like material with molecular weights ranging from 5,000 to 100,000 daltons, subsequent studies have shown that these substances were not homogeneous, did not have the high specific activity expected of true inhibin and/or failed to exhibit the molecular characteristics of inhibin as described herein (de Jong, Inhibin-Factor Artifact, "Molecular & Cellular Endocrin." 13: 1–10 (1979); Sheth et al., 1984, "F.E.B.S." 165(1) 11–15; Seidah et al., 1984, "F.E.B.S." 175(2):349–355; Lilja et al., March 1985, "F.E.B.S." 182(1):181–184; Li et al., June 1985, "Proc. Nat. Acad. Sci. U.S.A." 82:4041–4044; Seidah et al., "F.E.B.S." 167(1):98–102; and Baksac et al., 1984, "Intern. J. Andrology" 7:389–397).

A polypeptide having inhibin activity was purified from bovine or ovine follicular fluid (PCT 86/00078, published Jan. 3, 1986). This protein was reported to have a molecular weight of 56,000±1,000 on SDS-PAGE and was dissociable into two subunits having apparent molecular weights of 44,000±3,000 and 14,000±2,000. Amino terminal sequences for each subunit were described.

Two proteins both having a molecular weight of about 32,000 daltons and having inhibin activity have been successfully isolated from porcine follicular fluid. Purification of porcine inhibin to substantial homogeneity, i.e., about 90% by weight of total protein in the fraction, was achieved through a combination of protein separation procedures including heparin-Sepharose affinity chromatography, gel filtration and reverse-phase, high-performance liquid chromatography (RP-HPLC).

These proteins were isolated to substantial homogeneity from material obtained from swine and are referred to as Protein A and Protein B. Each protein has a molecular weight of about 32,000 daltons (32K) and is composed of two polypeptide chains having molecular weights of 18,000 and 14,000 daltons, respective, the chains being linked together in the hormonally-active protein by disulfide bonding. The amino-terminal amino acid residue sequence of the 18,000 dalton (18K) or alpha chain of both proteins was determined to be Ser-Thr-Ala-Pro-Leu-Pro-Trp-Pro-Trp-Ser-Pro-Ala-Ala-Leu-Arg-Leu-Leu-Gln-Arg-Pro-Pro-Glu-Glu-Pro-Ala-Val (SEQ ID NO. 1). The amino-terminal amino acid residue sequence of the 14,000 dalton (14K) or beta chain of Protein A was determined to be Gly-Leu-Glu-X-Asp-Gly-Lys-Val-Asn-Ile-X-X-Lys-Lys-Gln-Phe-Phe-Val-Ser-Phe-Lys-Asp-Ile-Gly-Trp-Asn-Asp-Trp-Ile-Ile-Ala (SEQ ID NO. 2) and of Protein B was determined to be Gly-Leu-Glu-X-Asp-Gly-Arg-Thr-Asn-Leu-X-X-Arg-Gln-Gln-Phe-Phe-Ile-Asp-Phe-Arg-Leu (SEQ ID NO. 3). Proteins A and B have been completely characterized. Each 32K protein exhibits inhibin activity in that is specifically inhibits the basal secretion of FSH but does not inhibit secretion of luteinizing hormone (LH). The individual chains were not hormonally active.

After the filing of the parent application hereto, inhibin B-chain dimers were shown to exist in follicular fluid as naturally-occurring substances, termed activin, which are capable of stimulating FSH release by rat anterior pituitary cells (Vale et. at., 1986, "Nature" 321: 776–779 and Ling et al., 1986, "Nature" 321: 779–782).

The amino acid sequence of the α and β chains of inhibin from humans remained unknown until the invention herein. The large quantities of human follicular fluid required to parallel the studies conducted with animal inhibins are not readily available, not is there any assurance that human and animal inhibins would be sufficiently similar that purification using a parallel procedure would be effective. Accordingly, methods are needed for determining the characteristics and amino acid sequence for human inhibin.

Also needed are economical methods for making the α and β chains of inhibin in large quantities, preferably entirely and completely free of proteins from the species homologous to the inhibin in question, which inhibin preferably also is biologically active.

These and other objects will be apparent from consideration of the invention as a whole.

SUMMARY

Nucleic acid now has been isolated and cloned in replicable vectors which encodes the mature porcine and human α and β chains of inhibin and their precursor prepro and pro forms. Sequencing of inhibin-encoding cDNA has led to the identification of prodomain regions located N-terminal to the mature inhibin chains that represent coordinately expressed biologically active polypeptides. The prodomain regions or prodomain immunogens are useful in monitoring preproinhibin processing in transformant cell culture or in experiments directed at modulating the clinical condition or reproductive physiology of animals. Thus α and β chain nucleic acid is used to prepare prodomain sequences from the precursor forms of the inhibin chains, to transform host cells for the recombinant expression of mature inhibin α and/or β chains, and in diagnostic assays. In particular, regions from inhibin α and/or β chains are expressed in recombinant cell culture by a method comprising ligating the nucleic acid encoding the region into a replicable vector under the control of a promoter, transforming a host cell with the vector, culturing the host cell and recovering the prodomain, activin or inhibin from the cultured cell. Inhibin, activin and prodomains produced by the method of this invention are entirely free of homologous source proteins and can be produced in biologically active form.

The nucleic acids identified herein encode the α, $β_A$ and $β_B$ chains of porcine or human inhibin. Recombinant cells are transformed to express $αβ_A$ or $αβ_B$ inhibins, or to express β-chain heterodimers or homodimers (which are collectively refereed to in the literature as activin). β-chain dimers as products of recombinant cell expression are free of homologous proteins with which they ordinarily are associated in nature.

Inhibin or activin and their nontoxic salts, combined with a pharmaceutically acceptable carrier to form a pharmaceutical composition, are administered to mammals, including humans, for control of fertility. Administration of inhibin decreases fertility in female mammals and decreases spermatogenesis in male mammals, and administration of a sufficient amount induces infertility. Inhibin is also useful in tests to diagnose infertility. Activin has been shown in the literature to be capable of stimulating FSH release from pituitary cells and accordingly is useful as a fertility inducing therapeutic.

The method of this invention also facilitates the convenient preparation of inhibin, activin and prodomain variants having primary amino acid sequences and/or glycosylation differing from the native analogues, in particular fusions of immunogenic peptides with inhibin, activin or prodomain sequences.

BRIEF DESCRIPTION OF THE DRAWINGS

FIG. 1B shows the nucleotide sequence (SEQ ID NO. 30) and predicted amino acid sequence (SEQ ID NO. 29) of the porcine inhibin α-chain precursor. Nucleotides are numbered at the left and amino acids are numbered throughout. The amino acid sequence underlined was used to design a long synthetic DNA probe. The 364 amino acid precursor includes a hydrophobic signal sequence, a pro-region, and the mature α-chain (amino acids 231–364). The proteolytic processing site Arg-Arg (black bar) immediately precedes the $NH_2$-terminus of the mature alpha chain. Several other putative dibasic processing sites present in the pro-region are indicated by open bars. The single potential N-linked glycosylation site is shown by the cross-hatched bar. The AATAAA box close to the 3' end of the mRNA is underlined.

FIG. 4A is a comparison of the human β-TGF amino acid sequence (SEQ ID NO. 36) and porcine inhibin $β_A$ and $β_B$ amino acid sequences (SEQ ID NOS. 35 and 37, respectively). The sequences were aligned around the cysteine residues. Identical residues are boxed, while conservative changes are designated by an asterisk.

FIG. 4B compares the α-subunit sequence (SEQ ID NO. 38) with the $β_A$-inhibin sequence (SEQ ID NO. 55).

FIG. 6 shows the nucleotide sequence and deduced amino acid sequence of the human α-inhibin cDNA. The 335 amino acid pro- or inhibin sequence (SEQ ID NO. 40) is numbered from the hypothesized signal cleavage site. Sixteen amino acids of the signal sequence (SEQ ID NO. 39) are numbered −1 through −16. Homology with the porcine sequence predicts a further 12 amino acid residues in the signal sequence. In this and other figures, putative dibasic processing sites are shown by the open bars, glycosylation sites indicated by cross-hatched bars, and amino terminal mature chain processing sites are depicted as black bars. The poly(A) additional signal sequence is underlined. Cysteine residues are shaded.

FIG. 7 is a comparison of the human and porcine α-inhibin precursor from protein sequences. Spaces are introduced to maximize the homology; positions of non-identity are indicated by stars. Numbering is as form the porcine sequence (SEQ ID NOS. 39 and 29 respectively) which is one amino acid shorter than the human.

FIG. 8 shows the nucleotide sequence (SEQ ID NO. 42) and deduced amino acid sequence (SEQ ID NO. 41) of the human $\beta_A$ inhibin precursor. The figure shows that human $\beta_A$ inhibin signal sequence (residue −28 through −1) is 28 amino acids with the precursor being 378 amino acids in length. The basic processing site is indicated by a black bar, and a potential glycosylation site in the precursor is indicated by a cross-hatched bar above the sequence. Cysteine residues are shaded.

FIG. 9 illustrates the nucleotide sequence (SEQ ID NO. 44) and deduced amino acid sequence (SEQ ID NO. 43) of human $\beta_B$ inhibin precursor from cDNA. The sequence commences at a cysteine residue (position 7), which lines up with the cysteine present at residue 7 in the $\beta_A$ sequence (see FIG. 8). The processing site for the mature $\beta_B$ inhibin is shown as a black bar and a potential glycosylation site as a cross-hatched bar. Cysteine residues are shaded.

DETAILED DESCRIPTION

Figure 1A:
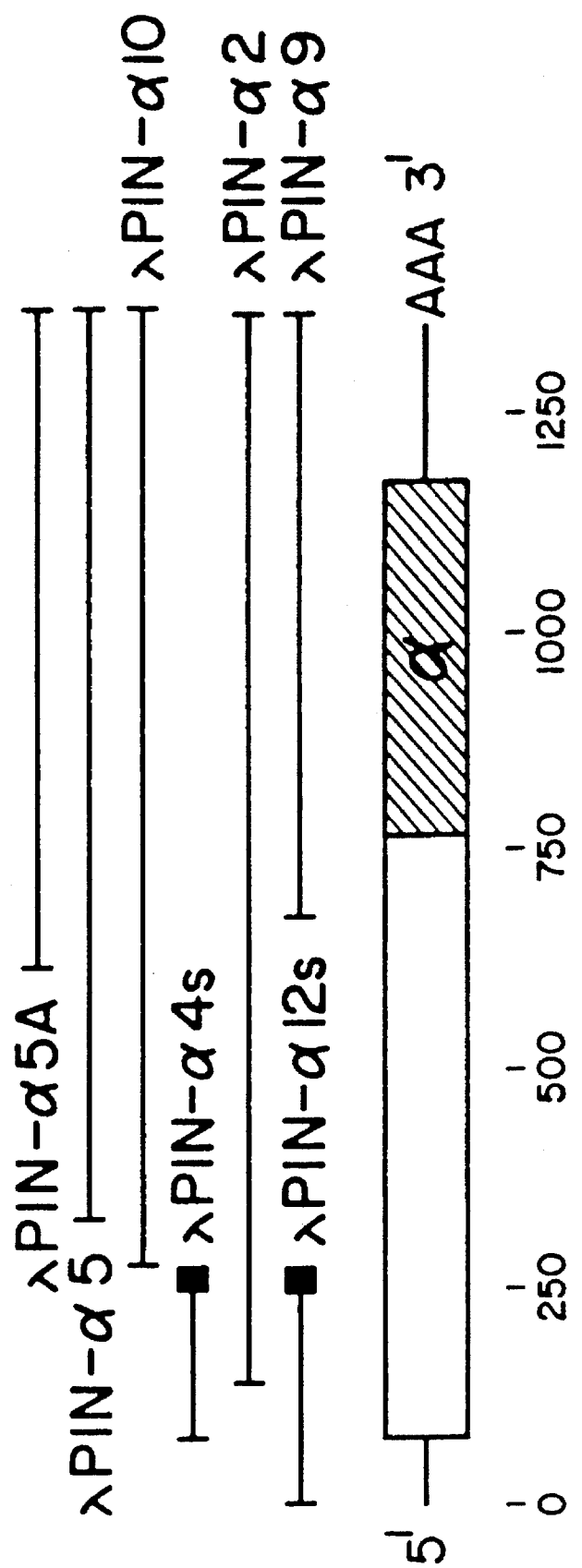
FIG. 1A is a schematic representation of the porcine α-chain mRNA. Overlapping cDNA clones used in the sequence determination are shown above the diagram of the mRNA structure. Black boxes on the 3' ends of λ clones indicate that these clones were obtained by specific priming. Untranslated sequences are represented by a line, coding sequences are boxed. The unfilled portion represents the coding region for the signal peptide and pro-sequences, and the cross-hatched area indicates the 134 amino acid α-chain. The scale is in nucleotides from the 5' end of the longest cDNA clone.

The polypeptides of this invention are the α and β chains of inhibin, as well as their multimer forms (activin and inhibin), their prepro forms and their prodomains, together with glycosylation and/or amino acid sequence variants of each chain or form thereof. Inhibin (including alleles) from human or animal sources inhibits the basal release of FSH but not of LH from anterior pituitary cells while activin does the opposite (hereinafter referred to as "hormonally active" activin or inhibin).

Generally, amino acid sequence variants will be substantially homologous with the relevant portion of the porcine or human α or β chain sequences set forth in FIGS. 1B, 2B, 6, 8 and 9. Substantially homologous means that greater than about 70% of the primary amino acid sequence of the candidate polypeptide corresponds to the sequence of the porcine or human chain when aligned in order to maximize the number of amino acid residues matches between the two proteins. Alignment to maximize matches of residues includes shifting the amino and/or carboxyl terminus, introducing gaps as required and/or deleting residues present as inserts in the candidate. For example, see FIGS. 2B and 7 where the $\beta_A$ and $\beta_B$ subunits for human and porcine α-inhibin sequences are aligned for maximum homology. Typically, amino acid sequence variants will be greater than about 90% homologous with the corresponding native sequences shown in FIGS. 1B, 2B, 6, 8 and 9.

Variants that are not hormonally-active fall within the scope of this invention, and include polypeptides that may or may not be substantially homologous with either a mature inhibin chain or prodomain sequence, but which are 1) immunologically cross-reactive with antibodies raised against the native counterpart or 2) capable of competing with such native counterpart polypeptides for cell surface receptor binding. Hormonally inactive variants are produced by the recombinant or organic synthetic preparation of fragments, in particular the isolated α or β chains of inhibin, or by introducing amino acid sequence variations so that the molecules no longer demonstrate hormonal activity as defined above.

Immunological or receptor cross-reactivity means that the candidate polypeptide is capable of competitively inhibiting the binding of the hormonally-active analogue to polyclonal antisera raised against the hormonally-active analogue. Such antisera are prepared in conventional fashion by injecting goats or rabbits S.C. with the hormonally-active analogue or derivative in complete Freunds adjuvant, followed by booster intraperitoneal or S.C. injections in incomplete Freunds.

Variants that are not hormonally active but which are capable of cross-reacting with antisera to hormonally-active inhibin, activin, or prodomains are useful (a) as reagents in diagnostic assays for the native analogues or their antibodies, (b) when insolubilized in accord with know methods, as an agent for purifying anti-native analogue antibodies from antisera, and (c) as an immunogen for raising antibodies to a hormonally-active analogues.

This invention includes the pro and/or prepro sequences of the inhibin α or β chain precursors, or their immunologically or biologically active fragments, substantially free of the corresponding mature inhibin chains. These sequences for porcine and human inhibin are shown in FIGS. 1B, 2B, 6, 8 and 9. The prepro sequence for the porcine α subunit precursor is the polypeptide comprised by residues 1 to about 230, while the $\beta_A$ subunit pro sequence is comprised by residues 1 to about 308. These sequences shall be referred to herein as encompassing prodomain sequences.

The α and β subunit prodomain sequences are comprised of several domains bounded by proteolysis sites, any one of which is synthesized herein separately or in combination with other domains. The principal porcine $\beta_A$ domains fall within residues 1 to about 70 (domain I), about 70 to about 110 (domain II), about 110 to about 180 (domain III), about 180 to about 260 (domain IV), and about 270 to about 309 (domain V). In particular, the porcine $\beta_A$ domains are GHSAAPDCPSCALATLPKDVPNSQPEMVEAV (SEQ ID NO. 5), HILNMLHLKKRPDVTQPVPKAALLNAI (SEQ ID NO. 6), LHVGKVGENGYVELEDDIG (SEQ ID NO. 7), AEMNELMEQTSEIITFAEAGRARKTLRFEISKEGSDLSVVERAEIWLFKVPKANRTRTKVSIRLFQQQ (SEQ ID NO. 8), PQGSADAGEEAEDVGFPEEKSEVLISEKVVDA (SEQ ID NO 9), STWHIFPVSSSIQRLLDQGKSALDIRTACEQCHETGASLVLLG (SEQ ID NO. 10), and GHSAAPDCPSCALATLPKDVPNSQPEMVEAVKKHILNMLHLKKRPDVTQPVPKAALLNAI (SEQ ID NO. 11), The porcine $\beta_B$ domains comprise RAAHILLHAVRVSGWLNL (SEQ ID NO. 12) as well as homologous β domains having the same sequences. The porcine α domains comprise GPELDRELVLAKVRALFLDALGPPAVTGEGGDPGV (SEQ ID NO. 13) and GSEPEEEDVSQAILFPATGARCGAEPAAGELAREAEEGLFTYVGRPSQHTHSRQVTSAQLWFHTGL DRQGMAAANSSGPLLDLLALSSRGPVAVPMSLGQAPPRWAVLHLAASALPLLTHPVLVLL LRCPLC SCSARPEATPFLVAHTRARPPSGGERA (SEQ ID NO. 14). A typical combination domain polypeptide would be $\beta_A$ domain II linked at its C-terminus to the NH$_2$-terminus of $\beta_A$ domain III. In addition, these domains are fused together by the proteolysis sites found in the sequences shown in FIGS. 1B or 2B, by 1 to 4 residue polypeptides that are resistant to hydrolysis (for example, glutaminyl or histidyl residues), or are directly fused, whereby, in all three instances, combination domain polypeptides are produced.

Principal human α chain prodomains are approximately residues 30–199, and 1 to 29, human βA prodomains are approximately residues 1–30, 32–40, 43–59, 62–80, 83–185 and 186–230 while human $\beta_B$ prodomains are approximately residues 1–13, 15–30, 32–59, 62–145, 148–195 and 198–241 (referring to the numbering system adopted in FIGS. 6, 8 and 9, respectively). Combination prodomain polypeptides are within the scope hereof, for example, the $\beta_A$ prodomain at about 43–80, and the $\beta_B$ prodomains at about 1–30 and about 32–145. The preferred human $\alpha$, $\beta_A$ and $\beta_B$ chain prodomains are about residues 1–29, about 43–80 and about 1–30, respectively.

The intact isolated prepro or prodomain $\beta_A$, $\beta_B$ or $\alpha$ sequences are best synthesized in recombinant cell culture. The individual subcomponent domains are synthesized by routine methods of organic chemistry or by recombinant cell culture. They then are labelled with a radioisotope or other detectable group such as an enzyme or fluorophore in accord with known methods and used in standard competitive immunoassays to detect the levels of prepro or pro forms of inhibin, including individual domains, in transformants with DNA encoding such forms or their precursors. This assay is useful in determining whether proteolytic hydrolysis of proinhibin is occurring in the host transformants or their culture media. The assay also is useful in determining whether a rate limiting step in recombinant synthesis is translation of mRNA into the prepro forms or processing of the prepro forms into mature inhibin. For example, high levels of prepro or pro inhibin in cell lysates, but relatively low levels of secreted mature inhibin, would suggest that the host cell is adequately transcribing and translating the inhibin DNA, but is not processing the precursors at an adequate rate. Thus, in this case one would select an alternate host cell rather than concentrating on improving the transcription or translation efficiency of the transforming plasmid, e.g., by selecting an alternative promoter. The prodomain sequences also are believed to be involved in coordinate modulation of animal physiology in reproductive cycles and fertility.

Amino acid sequence variants are any one of 1) hormonally-active, 2) cross reactive with antibodies raised against mature inhibin or prodomain $\alpha$ or $\beta$ chain sequences, or 3) cross-reactive with inhibin/activin cell surface receptors, but are characterized by a primary amino acid sequence that departs from the sequence of natural inhibins or prodomain sequences. These derivatives ordinarily are preprepared by introducing insertions, deletions or substitutions of nucleotides into the DNA encoding the target DNA to be modified in order to encode the variant, and thereafter expressing the DNA in recombinant cell culture. Polypeptides having up to about 100–150 residues also are conveniently prepared by in vitro synthesis. Such variants are characterized by the predetermined nature of the variation, a feature that sets them apart from naturally occurring allelic or interspecies variation. The variants may exhibit the same qualitative biological activity as the naturally-occurring analogue or may act antagonistically towards such analogues.

While the site for introducing a sequence variation is predetermined, it is unnecessary that the mutation per se be predetermined. For example, in order to optimize the performance of mutation at a given site, random mutagenesis may be conducted at the target codon or region and the expressed inhibin mutants screened for the optimal combination of desired activity. Techniques for making substitution mutations at predetermined sites in DNA having a known sequence is well known, for example M13 primer mutagenesis.

Mutagenesis is conducted by making amino acid insertions, usually on the order of about from 1 to 10 amino acid residues, or deletions of about from 1 to 30 residues. Deletions or insertions preferably are made in adjacent pairs, i.e. a deletion of 2 residues or insertion of 2 residues. Substitutions, deletions, insertions or any subcombination may be combined to arrive at a final construct. Insertions include amino- or carboxyl-terminal fusions, e.g. a hydrophobic extension added to the carboxy terminus. Preferably, however, only substitution mutagenesis is conducted. Obviously, the mutations in the encoding DNA must not place the sequence out of reading frame and preferably will not create complementary regions that could produce secondary mRNA structure.

Not all mutations in the DNA which encode the polypeptides herein will be expressed in the final secreted product. For example, a major class of DNA substitution mutations are those in which a different secretory leader or signal has been substituted for the native porcine or human $\alpha$ or $\beta$ chain secretory leader, either by deletions within the leader sequence or by substitutions, wherein most or all of the native leader is exchanged for a leader more likely to be recognized by the intended host. For example, in constructing a procaryotic expression vector the porcine or human $\alpha$ or $\beta$ chain secretory leader is deleted in favor of the bacterial alkaline phosphatase or heat stable enterotoxin II leaders, and for yeast the leader is substituted in favor of the yeast invertase, alpha factor or acid phosphatase leaders. However, the porcine and human secretory leaders are recognized by many heterologous higher eukaryotic cells. When the secretory leader is "recognized" by the host, the host signal peptides is capable of cleaving a fusion of the leader polypeptide fused at its C-terminus to the mature inhibin or prodomain such that mature inhibin or prodomain polypeptide is secreted.

Another major class of DNA mutants that are not expressed in final form as amino acid sequence variations are nucleotide substitutions made in the DNA to enhance expression, primarily to avoid 5' stem and loop structures in the transcribed mRNA (see de Boer et al., EP 74,444A) or to provide codons that are more readily transcribed by the selected host, e.g. the well-known preference codons for *E. coli* or yeast expression. These substitutions may or may not encode substituted amino acid residues, but preferably do not.

Insertional and deletional amino acid sequence variants are proteins in which one or more amino acid residues are introduced into or removed from a predetermined site in the target inhibin, activin, prodomain or proform of inhibin or activin. Most commonly, insertional variants are fusions of heterologous proteins or polypeptides to the amino or carboxyl terminus of the $\alpha$ or $\beta$ chains, the prodomains or other inhibin derivatives. Immunogenic derivatives are made by fueling an immunogenic polypeptide to the target sequence, e.g. a prodomain polypeptide, by synthesis in vitro or by recombinant cell culture transformed with DNA encoding the fusion. Such immunogenic polypeptides preferably are bacterial polypeptides such as trpLE, beta-galactosidase and the like, together with their immunogenic fragments. Other insertions entail inserting heterologous eukaryotic (e.g. the herpes virus gD signal) or microbial secretion signal or protease processing sequences upstream from the $NH_2$-terminus of the protein to be secreted. Deletions of cysteine or other labile residues also may be desirable, for example in increasing the oxidative stability of the $\alpha$ or $\beta$ chain. Deletional derivatives will produce $\alpha$ or $\beta$ chain fragments. Such fragments, when biologically or immunologically active, are within the scope herein. For instance, a fragment comprising $\beta_B$ or $\beta_A$ residues about from 11 to 45 (numbered from mature $Gly_1$) is to be included within the scope herein.

Immunogenic conjugates of prodomain polypeptides, inhibin and activin are readily synthesized in recombinant cell culture as fusions with immunogenic polypeptides, e.g. beta-lactamase or viral antigens such as the herpes gD protein, or by preparation of the polypeptides in unfused form (by recombinant or in vitro synthetic methods) followed by covalent cross-linking to an immunogenic polypeptide such as keyhold limpet hemocyanin or STI using a divalent cross-linking agent. The immunogenic polypeptides are formulated with a vaccine adjuvant, e.g. alum or Freunds. Methods for preparing proteins in adjuvants and for cross-linking are well-know per se and would be employed by one skilled in the art, as are methods for vaccinating animals. The immunogenic conjugates are useful in preparing antibodies to the prodomain region for use in monitoring inhibin manufacture or for in vivo vaccination with the objective of raising antibodies capable of modulating animal physiology in reproductive cycles and fertility. Typically, the prodomain or its immunogen is administered in varied doses to fertile laboratory animals or swine and the reproductive cycles and fertility of the animals monitored, together with assays of serum levels of anti-immunogen or prodomain by routine competitive or sandwich immunoassay.

Substitution derivatives are produced by mutating the DNA in a target codon, so that thereafter a different amino acid is encoded by the codon, with no concomitant change in the number of residues present in the molecule expressed from the mutated DNA. Substitutions or deletions are useful for example in increasing the stability of the proteins herein by eliminating proteolysis sites, wherein residues are substituted within or adjacent to the sites or are deleted from the sites, or by introducing additional disulfide bonds through the substitution of cysteine for other residues. Substitutions are useful for facilitating the synthesis or recovery of mature or prodomain α or β chains. For example, methionine residues within the mature inhibin sequences are substituted or deleted, prepro sequences deleted, methionine is inserted at the −1 site immediately $NH_2$ terminal to the mature $NH_2$ terminal residue and another sequence inserted N-terminal to the exogenous methionine. The inhibin derivative in this case is expressed as a fusion having an intermediate methionyl residue, which in turn is cleaved at this residue by cyanogen bromide in accordance with known practice. The mature inhibin derivative released from the fusion is recovered.

Exemplary porcine inhibin derivatives are [$Asn_{266}$→Gln] Inhα (to remove the putative glycosylation site), [$Cys_{325}$ or $Cys_{324}$→Δ]Inhα, [$Cys_{361}$ or $Cys_{363}$→Δ]Inhα, [$Lys_{321}$ or $Lys_{322}$→Δ]Inhβ$_A$ or [$Lys_{322}$→His or Ser]Inhβ$_A$ (to inactivate a potential proteolysis site), [$Lys_{315}$→Arg; $Val_{316}$→Thr] Inhβ$_A$ (to create a β$_A$/β$_B$ hybrid), [$Cys_{388}$ or $Cys_{390}$→Δ]Inhβ$_A$, [$Lys_{411}$→Gln]Inhβ$_A$, [$Arg_{315}$→Lys, $Val_{316}$→Thr] Inhβ$_B$ (to create a β$_B$/β$_A$ hybrid), [$Cys_{319}$ or $Cys_{320}$→Δ] Inhβ$_B$ [$Pro_{381}$ $Gly_{382}$→Pro Phe Gly]Inhβ$_B$, and [$Arg_{395}$→Gln]Inhβ$_B$, wherein Inh is an abbreviation for inhibin and the residue numbers for Inhβ$_B$ are those used for the corresponding Inhβ$_A$ residue (see FIG. 2B).

The hβ$_A$ amino acid positions which are principal candidates for mutational substitution or deletion (or adjacent to which residues may be inserted) include residues 293–297, 364–376 and 387–398 (FIG. 8). Preferably, the proline, cysteine and glycine residues within these sequences are not modified. Candidates having greater potency than inhibin or activin, or which serve as inhibin or activin antagonists, are identified by a screening assay wherein the candidate is diluted into solutions containing constant amounts of inhibin or activin and the compositions are assayed in the rat pituitary cell assay. Candidates which neither antagonize or agonize inhibin or activin are screened for utility in immunoassays for inhibin or activin by measuring competitive immunodisplacement of labelled inhibin or activin of the native hormones from polyclonal antibody directed against the native hormones. Exemplary contemplated sequence variants of hβ$_A$ include $Phe_{302}$→Ile or Leu; $Gln_{297}$→Asp or Lys; $Trp_{307}$→Tyr or Phe; $Trp_{310}$→Tyr or Phe; $Ile_{311}$→Phe or Val; $Tyr_{317}$→Trp or Thr; $His_{318}$→Lys; $Ala_{319}$→Ser; $Asn_{320}$→Gln, Tyr or His; $Tyr_{321}$→Thr or Asp, $Phe_{340}$→Tyr (a TGF-β/β$_A$ intrachain hybrid); $His_{353}$→Asp; $His_{353}$→Lys (a β$_A$/β$_B$ hybrid); $Phe_{356}$→Tyr; $Val_{364}$→Phe; $Val_{364}$→Leu; $Tyr_{375}$→Thr; $Tyr_{376}$→Trp; $Asn_{389}$→Gln, His or Lys; $Ile_{391}$→Leu or Thr; $Met_{390}$→Leu or Ser; $Val_{392}$→Phe, Glu, Thr or Ile. Comparable modifications are made in the human β$_B$ chain. For example, hβ$_A$ contains a phenylalanyl residue at position 302, and hβ$_B$ also contains a phenylalanyl residue at a homologous position (264, FIG. 9) when aligned in the same fashion as is shown for porcine β$_B$ in FIG. 4A. Thus, since the $Phe_{302}$ residue of β$_A$ is described above as substituted by isoleucinyl or leucinyl, the $Phe_{264}$ of β$_B$ is substituted with the same residues.

A factor in establishing the identity of a polypeptide as inhibin, activin or an inhibin variant is the ability of antisera which are capable of substantially neutralizing the hormonal activity of mature inhibin or activin to also substantially neutralize the hormonal activity of the polypeptide in question. However it will be recognized that immunological identity and hormonal activity are not necessarily coextensive. For example, a neutralizing antibody for inhibin may not bind a candidate protein because the neutralizing antibody happens to not be directed to specifically bind a site on inhibin that is critical to its activity. Instead, the antibody may bind an innocuous region and exert it neutralizing effect by steric hindrance. Therefore a candidate protein mutated in this innocuous region might no longer bind the neutralizing antibody, but it would nonetheless be inhibin in terms of substantial homology and biological activity.

It is important to observe that characteristics such as molecular weight, isoelectric point and the like for a native or wild type mature inhibin or activin obtained from follicular fluid or other tissue sources are descriptive only for the native form. Variants contemplated by the foregoing definition will include other polypeptides which will not exhibit all of the characteristics of native analogue. For example, inhibin derivatives like the insertion mutants, deletion mutants, or fusion proteins described above will bring inhibin outside of the molecular weight established for the corresponding native inhibin because fusion proteins with mature inhibin or proinhibin itself as well as insertion mutants will have a greater molecular weight than native, mature inhibin. On the other hand, deletion mutants of native, mature inhibin will have a lower molecular weight. Finally, post-translational processing of preproinhibin chains in heterologous cell lines may not be accomplished with the fidelity exercised by the homologous host cell, thereby resulting in some variation in the amino termini of the α and/or β chains. This variation may be encountered as residual prosequence remaining with the mature protein, or the loss of several mature residues that are cleaved off with the prosequence. The same is true with processing of the preprotein in heterologous recombinant cells.

Covalent modifications of inhibin, activin or prodomains are included within the scope hereof and include covalent or aggregative conjugates with other chemical moieties. Covalent derivatives are prepared by linkage of functionalities to groups which are found in the inhibin amino acid side chains or at the N- or C-termini, by means known in the art. For example, there derivatives will include: aliphatic esters or amides of the carboxyl terminus or residues containing carboxyl side chains, e.g., aspartyl residues; O-acyl derivatives of hydroxy group-containing residues such as seryl or alanyl; and N-acyl derivatives of the amino terminal amino acid or amino-group containing residues, e.g. lysine or arginine. The acyl group is selected from the group of alkyl moieties (including C3 to C10 normal alkyl), thereby forming alkanoyl species, and carbocyclic or heterocyclic compounds, thereby forming aroyl species. The reactive groups preferably are difunctional compounds known per se for use in cross-linking proteins to insoluble matrices through reactive side groups, e.g. m-maleimidobenzoyl-N-hydroxy succinimide ester. Preferred derivatization sites are at histidine residues.

Covalent or aggregative derivatives of mature inhibin, activin or prodomian sequences are useful as reagents in immunoassay or for affinity purification procedures. For example, inhibin or prodomain is insolubilized by covalent bonding to cyanogen bromide-activated Sepharose by means know per se or adsorbed to polyolefin surfaces (with or without glutaraldehyde cross-linking) for use in the assay or purification of anti-inhibin or anti-prodomain antibodies or cell surface receptors. Inhibin or a prodomain sequence also is labelled with a detectable group, e.g., radioiodinated by the chloramine T procedure, covalently bound to rare earth chelates or conjugated to another fluorescent moiety for use in diagnostic assays, especially for diagnosis of inhibin or prodomain levels in biological samples by competitive-type immunoassays.

DNA which encodes the complete $\alpha$ and $\beta$ chains of inhibin/activin is obtained by chemical synthesis, by screening reverse transcripts of mRNA from ovary, or by screening genomic libraries from any cell. It may be more efficient to simply synthesize portions of the DNA desired since screening is required to identify DNA in cDNA or genomic libraries that encode the $\alpha$ and $\beta$ chains. Synthesis also is advantageous because unique restriction sites can be introduced at the time of preparing the DNA, thereby facilitating the use of the gene in vectors containing restriction sites otherwise not present in the native sequence, and steps can be taken to enhance translational efficiency as discussed above, without the need to further modify the DNA as by mutagenesis or the like. cDNA encoding the $\alpha$ or $\beta$ chains is free of untranslated intervening sequences (introns) as well as free of flanking DNA encoding other proteins homologous to their source.

DNA encoding the $\alpha$ and $\beta$ chains is obtained from other sources that porcine or human by (a) obtaining a cDNA library from the ovary of the target animal, (b) conducting Southern analysis with labelled DNA encoding porcine or human $\alpha$ and $\beta$ chains or fragments thereof (generally, greater than 100 bp) in order to detect clones in the cDNA library that contain homologous sequences, (c) analyzing the clones by restriction enzyme analysis and nucleic acid sequencing so as to identify full-length clones and, if full length clones are not present in the library, recovering appropriate fragments from the various clones and ligating them at restriction sites common to the clones to assemble a clone encoding the full-length molecule. As shown infra, any sequences missing from the library can be obtained by the 3' extension on ovarian mRNA of synthetic oligodeoxynucleotides complementary to cDNA identified by screening the library, or homologous sequences are supplied from known animal cDNAs. This is particularly useful in constructing pre or prepro inhibin sequences to facilitate processing of preproinhibin to mature inhibin from the desired species.

Porcine and human ovarian cDNA libraries initially were probed for DNA encoding inhibin sequences using labelled oligonucleotides whose sequence was based on the partial amino acid sequence determined from analysis of purified porcine inhibin or, in the case of human cDNA, porcine cDNA probes. However, once having described cDNA encoding human and porcine inhibin and prodomains, one skilled in the art would realize that precisely hybridizing probes can be prepared from the described sequence in order to readily obtain the remainder of the desired human or porcine gene.

Nucleotide sequence analyses of identified porcine and human cDNA clones revealed the structures of the biosynthetic precursors of both forms of inhibin. Interestingly, the two inhibin chains are not derived from a single processed precursor. Instead, the two chains are translated from separate mRNAs and then assembled into the disulfide crosslinked two-chain molecule.

FIGS. 1B and 2B and 6, 8 and 9 depict the DNA encoding the polypeptide chains constituting porcine and human preproinhibin and preproactivin. Obviously, degenerate codons may be substituted for those disclosed in these figures where the same amino acid is encoded. The DNA of FIGS. 1B, 2B, 6, 8 and 9 is mutated in order to encode the amino acid variants of the $\alpha$ and $\beta$ chains described above. In particular, the prepro sequences are deleted and a start codon is inserted immediately 5' to the mature chain in question so that the chain is expressed directly in recombinant culture. The DNA also is labelled, e.g. with radioactive phosphorous, and used to screen ovarian cDNA libraries from other species to identify $\alpha$ or $\beta$ chain encoding DNA from such other species as is generally described above.

Covalent labelling of this DNA is accomplished with a detectable substance such as a fluorescent group, a radioactive atom or a chemiluminescent group by methods known per se. The labelled DNA is then used in conventional hybridization assays. Such assays are employed in identifying vectors and transformants as described in the examples infra, or for in vitro diagnosis such as detection of mRNA in tissues.

Lengthy sequences desirably are synthesized in host cells transformed with vectors containing DNA encoding them, e.g. inhibin or prodomain sequence. Vectors are used to amplify the DNA which encodes the chains, either in order to prepare quantities of DNA for further processing (cloning vectors) or for expression of the chains (expression vectors). An expression vector is a replicable DNA construct in which a DNA sequence encoding an $\alpha$ or $\beta$ chain is operably linked to suitable control sequences capable of effecting their expression in a suitable host. Cloning vectors need not contain expression control sequences. Such control sequences include a transcriptional promoter, an optional operator sequence to control transcription, a sequence encoding suitable mRNA ribosomal binding sites (for prokaryotic expression), and sequences which control termination of transcription and translation. The vector should include a selection gene to facilitate the stable expression of the desired polypeptide and/or to identify transformants. However, the selection gene for maintaining $\alpha$ and/or $\beta$ chain expression can be supplied by a separate vector in cotransformation systems using eukaryotic host cells.

Vectors comprise plasmids, viruses (including phage), and integratable DNA fragments i.e., fragments that are integratable into the host genome by recombination. The vectors described herein for use in eukaryotic cell expression of inhibin $\alpha$ and/or $\beta$ chains contain plasmid sequences for cloning in microbes, where the plasmid replicates autonomously from the host genome, but the DNA is believed to integrate into the eukaryotic host cell genome upon transformation. Similarly, bacillus vectors that genomically integrate by homologous recombination in a bacillus also are useful. However, all other forms of vectors which serve an equivalent function and which are, or become, known in the art are suitable for use herein.

Suitable vectors generally will contain replicon (origins of replication, for use in non-integrative vectors) and control sequences which are derived from species compatible with the intended expression host. Transformed host cells are cells which have been transformed or transfected with vectors containing inhibin α and/or β chain encoding DNA. Transformed host cells contain cloned DNA and, when transformed with an expression vector, also express the α and/or β chains. The expressed polypeptides will be deposited intracellularly or secreted into either the periplasmic space or the culture supernatant, depending upon the host cell selected and the presence of suitable processing signals in the expressed protein, e.g. homologous or heterologous signal sequences.

DNA regions are operably linked when they are functionally related to each other. For example, DNA for a presequence or secretory leader is operably linked to DNA for a polypeptide if it is expressed as a preprotein which participates in the secretion of the polypeptide; a promoter is operably linked to a coding sequence if it controls the transcription of the sequence; or a ribosome binding site is operably linked to a coding sequence if it is positioned so as to permit translation. Generally, operably linked means that the DNA sequences being linked are contiguous and, in the case of secretory leaders, contiguous and in reading phase.

Suitable host cells are prokaryotes, yeast or higher eukaryotic cells. Prokaryotes include gram negative or gram positive organisms, for example E. coli or Bacilli. Higher eukaryotic host cells include established cell lines of mammalian origin as described below. A preferred host cell is E. coli 294 (ATCC 31,446) although other prokaryotes such as E. coli B, E. coli X1776 (ATCC 31,537), E. coli W3110 (ATCC 27,325), pseudomonas species, or Serratia marcesans are suitable.

Expression vectors for host cells ordinarily include an origin of replication (where extrachromosomal amplification is desired, as in cloning, the origin will be a bacterial origin), a promoter located upstream from the inhibin coding sequences, together with a ribosome binding site (the ribosome binding or Shine-Dalgarno sequence is only needed for prokaryotic expression), RNA splice site (if the inhibin DNA contains genomic DNA containing one or more introns), a polyadenylation site, and a transcriptional termination sequence. As noted, the skilled artisan will appreciate that certain of these sequences are not required for expression in certain hosts. An expression vector for use with microbes need only contain an origin of replication recognized by the intended host, a promoter which will function in the host and a phenotypic selection gene, for example a gene encoding proteins conferring antibiotic resistance or supplying an auxotrophic requirement. Inhibin DNA is typically cloned in E. coli using pBR322, a plasmid derived from an E. coli species (Bolivar, et al., 1977, "Gene" 2: 95). pBR322 contains genes for ampicillin and tetracycline resistance and thus provides easy means for identifying transformed cells.

Expression vectors, unlike cloning vectors, must contain a promoter which is recognized by the host organism. This is generally a promoter homologous to the intended host. Promoters most commonly used in recombinant DNA constructions include the β-lactamase (penicillinase) and lactose promoter systems (Chang et al., 1978, "Nature", 275: 615; and Goeddel et al., 1979, "Nature" 281: 544), a tryptophan (trp) promoter system (Goeddel et al., 1980, "Nucleic Acids Res." 8: 4057 and EPO Appl. Publ. No. 36,776) and the tac promoter [H. De Boer et al., 1983, "Proc. Nat'l. Acad. Sci. U.S.A." 80: 21–25]. While these are the most commonly used, other known microbial promoters are suitable. Details concerning their nucleotide sequences have been published, enabling a skilled worker operably to ligate them to DNA encoding inhibin in plasmid vectors (Siebenlist et al., 1980, "Cell" 20:269) and the DNA encoding inhibin or its derivative. Promoters for use in prokaryotic expression systems also will contain a Shine-Dalgarno (S.D.) sequence operably linked to the DNA encoding the inhibin, i.e., the S.D. sequence is positioned so as to facilitate translation. Generally, this means that the promoter and S.D. sequences located upstream from the second codon of a bacterial structural gene are substituted for the sequences of prepro inhibin located 5' to the mature α and/or β chains.

In addition to prokaryotes, eukaryotic microbes such as yeast cultures are transformed with inhibin-encoding vectors. Saccharomyces cerevisiae, or common baker's yeast, is the most commonly used among lower eukaryotic host microorganisms. However, a number of other strains are commonly available and useful herein. Yeast vectors generally will contain an origin of replication from the 2 micron yeast plasmid or an autonomously replicating sequence (ARS), a promoter, DNA encoding the α and/or β chain, sequences for polyadenylation and transcription termination, and a selection gene. A suitable plasmid for expression in yeast is YRp7, (Stinchcomb et al., 1979, "Nature", 282: 39; Kingsman et al., 1979, "Gene", 7: 141; Tachemper et al., 1980, "Gene", 10:157). This plasmid already contains the trpl gene which provides a selection marker for a mutant strain of yeast lacking the ability to grow in tryptophan, for example ATCC No. 44076 or PEP4-1 (Jones, 1977, "Genetics", 85: 12). The presence of the trpl lesion in the yeast host cell genomes then provides an effective environment for detecting transformation by growth in the absence of tryptophan.

Suitable promoting sequences in yeast vectors include the promoters for metallothionein, 3-phosphoglycerate kinase (Hitzeman et al., 1980, "J. Biol. Chem.", 255: 2073) or other glycolytic enzymes (Hess et al., 1968, "J. Adv. Enzyme Reg.", 7: 149; and Holland et al., 1978, "Biochemistry", 17: 4900), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., EP 73,657A.

Other yeast promoters, which have the additional advantage of transcription controlled by growth conditions, are the promoter regions for alcohol dehydrogenase 2, isocytochrome C, acid phosphatase, degradative enzymes associated with nitrogen metabolism, and the aforementioned metallothionein and glyceraldehyde-3- phosphate dehydrogenase, as well as enzymes responsible for maltose and galactose utilization. In constructing suitable expression plasmids, the termination sequences associated with these genes are also ligated into the expression vector 3' of the inhibin or derivative coding sequences to provide termination and polyadenylation of the mRNA.

Cultures of cells derived form multicellular organisms are the preferred host cells herein because it is believed that expression of hormonally active inhibin or activin will only occur in such cells, with microbial expression resulting at most only in immunological cross-reactivity. In principle, any higher eukaryotic cell culture is workable, whether from vertebrate or invertebrate culture. Propagation of vertebrate cells in culture per se has become a routine procedure in recent years [*Tissue Culture,* Academic Press, Kruse and Patterson, editors (1973)].

Suitable host cells for expressing α or β chains in higher eukaryotes include: monkey kidney DVI line transformed by SV40 (COS-7, ATCC CRL 1651); baby hamster kidney cells (BHK, ATCC CRL 10); Chinese hamster ovary-cells-DHFR (described by Urlaub and Chasin, PNAS (U.S.A.) 77: 4216, [1980]); mouse sertoli cells (TM4, Mather, J. P., Biol. Reprod. 23: 243–251 [1980]); monkey kidney cells (CVI ATCC CCL 70); African green monkey kidney cells (VERO- 76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (WI38, ATCC CCL 75); human liver cells (Hep G2, HB 8065); mouse mammary tumor (MMT 060652, ATCC CCL 51); rat hepatoma cells (HTC, M1, 54, Baumann, M., et al., J. Cell. Biol. 85: 1–8 [1980]) and TRI cells (Mather, J. P. et al., Annals N.Y. Acad. Sci. 383: 44–68 [1982]).

The transcriptional and translation control sequences in vertebrate cell expression vectors preferably are provided from viral sources. For example, commonly used promoters are derived from polyoma, Adenovirus 2, and most preferably Simian Virus 40 (SV40). The early and late promoters of SV40 are particularly useful because both are obtained easily from the virus as a fragment which also contains the SV40 viral origin of replication (Fiers et al., 1978, "Nature", 273: 113). Smaller or larger SV40 fragments may also be used, provided the approximately 250 bp sequence extending from the Hind III site toward the Bgl I site located in the viral origin of replication is included. Further, it is also possible to utilize the genomic promoters, control and/or signal sequences normally associated with the α or β-chains, provided such control sequences are compatible with and recognized by the host cell.

An origin of replication may be provided either by construction of the vector to include an exogenous origin, such as may be obtained from SV40 or other viral (e.g. Polyoma, Adenovirus, VSV, or BFV) source, or may be provided by the host cell chromosomal replication mechanism. If the vector is integrated into the host cell chromosome, the latter is often sufficient.

Rather than using vectors which contain viral origins of replication, mammalian cells are cotransformed with DNA encoding a selectable marker and DNA encoding the α and/or β chains. An example of a suitable selectable marker is dihydrofolate reductase (DHFR) or thymidine kinase. Such markers are proteins, generally enzymes that enable the identification of transformant cells, i.e., cells which had been competent to take up exogenous DNA. Generally, identification is by survival of transformants in culture medium that is toxic to untransformed cells or from which the cells cannot obtain a critical nutrient without having taken up the marker protein.

In selecting a preferred host mammalian cell for transfection by vectors which comprise DNA sequences encoding both inhibin and DHFR, it is appropriate to select the host according to the type of DHFR protein employed. If wild type DHFR protein is employed, it is preferable to select a host cell which is deficient in DHFR thus permitting the use of the DHFR coding sequence as a marker for successful transfection in selection medium which lacks hypoxanthine, glycine, and thymidine (hgt⁻). An appropriate host cell in this case is the Chinese hamster ovary (CHO) cell line deficient in DHFR activity, prepared and propagated as described by Urlaub and Chasin, 1980, "Proc. Nat'l. Acad. Sci." (U.S.A.) 77: 4216.

On the other hand, if DNA encoding DHFR protein with low binding affinity for methotrexate (MTX) is used as the controlling sequence, it is not necessary to use DHFR resistant cells. Because the mutant DHFR is resistant to MTX, MTX containing media can be used as a means of selection provided that the host cells are themselves MTX sensitive. Most eukaryotic cells which are capable of absorbing MTX appear to be methotrexate sensitive. One such useful cell line is a CHO line, CHO-KI (ATCC No. CCL 61). Preferably, transformants are first selected for neomycin resistance (the transfection is conducted together with DNA encoding the neomycin resistance gene), followed by MTX amplification of the α and/or β chain expression as the case may be. See Kim et al., "Cell" 42: 129–138 (1985) and EP 160,457A.

Other methods suitable for adaptation to the synthesis of α and/or β chains in recombinant vertebrate cell culture as described in M-J. Gething et al., "Nature" 293: 620–625 (1981); N. Mantei et al., "Nature" 281: 40–46; and A. Levinson et al., EP 117,060A and 117,058A.

The inhibin α chain is expressed in recombinant cell culture with or without either of the β-chain molecules. Similarly, host cells are transformed with DNA encoding either or both of the mature β-chains. Based on analogy to TGF-β, the mature β-chains are capable of forming homodimers or $\beta_A/\beta_B$ heterodimers upon expression in recombinant culture. These structures are not inhibin and will be referred to herein as β-chain dimers or activin. These are useful in the preparation of active inhibin, serving as sources of the β-chain, or are used as gel electrophoresis standards to detect the diversion into β-chain dimers of β-chains synthesized in α and β chain cotransformants. As will be seen in Example 4, this is not a hypothetical problem. Of course, the dimers also are useful in modulating reproduction as noted above.

β-chain hetero- or homodimers are separated by in vitro unfolding of the individual chains followed by oxidative disulfide bond formation with the α-chain in accord with processes generally known per se. Preferably, however, in preparing mature inhibin the recombinant host is transformed with DNA encoding both the α and either of the β-chains. The intact hormonally active molecule is then assembled by the host cell in vivo, and it is thus unnecessary to combine the two chains by in vitro processing. The DNA encoding the α and β-chains is preferably located on the same vector, and under the control of the same promoter, but this is not essential.

Certain β-chain amino acid sequence variants identified in the screening procedure will not bind to pituitary cell surface receptors nor as a consequence will they exhibit hormonal activity. Such variants, when expressed as homodimers in recombinant cell culture, are useful in immunoassays for activin when they bear immunological epitopes cross-reactive with the native β-chain. In addition, such variants are coexpressed with DNA encoding hormonally active β-chain to yield a hybrid bearing native and variant β-chain. In this case the variant serves to stabilize the structure of the native β-chain. This form of β-chain heterodimer is useful, like the homodimer, in immunoassays for activin. It also may function as an activin antagonist.

The activin/inhibin β-chains also are coexpressed with TFG-β in order to produce β-chain/TFG-β hybrids. Vectors and methods for the expression of TFG-β are known. For example, see Derynck et al., Human Transforming Growth Factor-β Complementary DNA Sequence and Expression in Normal and Transformed Cells "Nature" 316: 701–705 (1985). Cotransformation of mammalian host cells by vectors bearing the TGF-β gene as described by Derynck et al. together with the $\beta_A$ or $\beta_B$ chains of activin/inhibin will result in secretion of a proportion of β-chain/TGF-β hybrid dimers. This hybrid is useful in preparing TGF-β/β-chain immunogene or in immunoassays.

Inhibin, activin or prodomain sequences are recovered from transformed cells in accord with per se known procedures. When a polypeptide is expressed in recombinant bacteria as a refractile body, the desired polypeptide is recovered and refolded by conventional methods. Alternatively, the culture supernatants from transformed cells that secrete activin or inhibin, preferably mammalian cells, are simply separated from the cells by centrifugation. Then the inhibin generally is purified by successive purification procedures that include heparin-Sepharose affinity chromatography, gel filtration and at least one and preferably several RP-HPLC (reverse phase high pressure liquid chromatography) steps using different conditions in the stationary phase and/or mobile phase. Prodomain sequences produced by in vitro synthesis will be purified by conventional methods.

The prodomain polypeptides that are preferred for use herein are recovered from the culture media of recombinant cells transformed to synthesize the α and/or β chains as appropriate for the desired prodomain. Specifically, they are recovered by separating the culture medium polypeptides on native electrophoresis gel, excising bands having the predicted molecular weight and thereafter purifying the eluted polypeptides further, for example by FPLC or HPLC, followed by amino acid sequence determination for the substantially homogeneous separated polypeptides. Purified prodomain polypeptides then are used to raise antibodies, e.g., in rabbits, which when used in immunoaffinity purification will simplify the recovery of the prodomains.

In the preferred procedure for isolating porcine hormonally active inhibin, clarified transformant culture supernatant or cell lysate is first purified by heparin-Sepharose affinity chromatography, next by gel filtration on Sephacryl S-200 gel and then with four successive RP-HPLCs using different mobile phase gradients and/or derivatized silica supports. Preferably, stationary phases having relatively low hydrophobicity are used, with C3-C8 columns being preferred and C3-C5 and phenyl columns being particularly preferred. Solute specificity of the mobile phase is preferably adjusted by varying the concentration of an organic component, particularly acetonitrile. Although a single RP-HPLC fractionation significantly increases the purity relative to the gel-filtrated material, two or more, and preferably four, RP-HPLC purifications are generally performed subsequent to successive treatment by heparin-Sepharose chromatography and gel filtration. This method has been found to be adaptable to the purification of human inhibin from recombinant cell culture as well.

The first step of the purification is heparin-Sepharose affinity chromatography, in which the protein is adsorbed to the Sepharose-bound heparin moieties under application conditions, and the adsorbed inhibin material is recovered by 1M NaCl elution. This step greatly expedites the purification procedure for crude extracts because it allows a relatively large volume of a crude extract to be processed fairly rapidly while recovering an amount of protein exhibiting total inhibin activity equal to at least 90% of that of the crude extract.

For the detection of inhibin activity in the various column fractions, aliquots ranging from 0.01% to 0.1% by volume are removed, and after adding 100 μg human serum albumin in 100 μl water, the solvents were evaporated in a Speed-Vac concentrator (Savant, Hicksville, N.Y.). The residue was redissolved in 3 ml 1% fetal bovine serum in HDMEM, filtered through a Millex-GS 0.22 μm filter (Millipore Corp., Bedford, Mass.) and assayed in duplicate. To speed up the bioassays during the purification process, only basal inhibition of FSH secretion exerted by the inhibin activity is determined and plotted in the region where the inhibin proteins were expected to migrate in the chromatograms.

To perform the heparin-Sepharose affinity chromatography, cell debris is spun down in a Beckman J2-21 centrifuge (Beckman Instruments, Inc., Pal Alto, Calif.) using a JA-20 rotor at 10,000 rpm for 30 minutes. One half of the supernatant is diluted to 10 times its volume by the addition of 0.01M Tris-HCl containing 0.1M NaCl, pH 7, in an Erlenmeyer flask and pumped simultaneously via silastic tubes (0.76 mm ID) into heparin-Sepharose (Pharmacia Fine Chemicals, Piscataway, N.J.) columns (3.5×9 cm) by two Rabbit 4-channel peristaltic pumps (Rainin Instrument Co., Inc., Emeryville, Calif.) at 40 ml/hr per column. After all the fluid has been pumped through the heparin-Sepharose, the eight columns are washed simultaneously with 0.01M Tris-HCl, pH 7, containing 0.1M NaCl in the same manner. The adsorbed proteins with inhibin activity are removed by washing the eight columns simultaneously with 0.01M Tris-HCl containing 1M NaCl, pH 7, as above, and the wash is collected into fractions. The inhibin activity is monitored by the in vitro bioassay described above. The columns are regenerated by further washing with 2M NaCl in 0.01M Tris-HCl, pH 7, and re-equilibrated with 0.1M Tris-HCl containing 0.1M NaCl for purification of remaining extract.

Next, the material is fractionated by gel filtration to separate proteins generally according to their molecular weights. The fractions having inhibin activity extracted by the heparin-Sepharose columns are pooled and dialyzed overnight to remove NaCl in a 28.6 mm cylinder diameter Spectrapor No. 3 membrane tubing with $M_r$ cutoff at 3,500 (Spectrum Medical Industries, Inc., Los Angeles, Calif.) against 30% acetic acid. The retailed fluid is centrifuged, as above, to remove a white precipitate, and the supernatant is divided into equal portions for applying to 5×100 cm Sephacryl S-200 superfine columns (Pharmacia Fine Chemicals, Piscataway, N.J.). Each column is eluted with 30% acetic acid at 20 ml for 22 min., and the column fractions are monitored by UV absorption at 280 nm and by bioassay.

The bioassay-positive protein from the S-200 columns is pooled and lyophilized. The lyophilized material is dissolved in 0.2N acetic acid (1 ml/ml) and filtered through a Millex-HA 0.45 μm filter (Millipore Corp., Bedford, Mass). The filtrate is applied directly onto a 1×25 cm Vydac 5-μm particle-size C4 column (The Separations Group Hesperia, Calif.) and developed with a gradient of TEAP buffer. In the TEAP system, buffer A consists of 0.25N triethylammonium phosphate pH 3, and buffer B is 80% acetonitrile in buffer A. After all the filtrate had been loaded, the column is washed with the aqueous buffer A until the UV absorption reached baseline. The fractions exhibiting inhibin activity are separated in a Beckman 332 gradient liquid chromatography system (Beckman Instruments, Inc., Berkeley, Calif.) equipped with a Spectroflow 757 UV detector (Kratos Analytical Instruments, Ramsey, N.J.), a Soltec 220 recorder (Soltec Corp., Sun Valley, Calif.) and a Redirac 2112 fraction collector (LKB Instruments, Inc., Gathersburg, Md.). Zones of inhibin activity are detected by bioassay.

Inhibin protein containing the $β_B$ chain is further purified free of inhibin containing the $β_A$ species, if desired, by two more RP-HPLC steps. The first step uses a 1×25 cm Vydac 5-μm-particle-size C4 column and a trifluoroacetic acid (TFA) buffer system and the second step employs a 1×25 cm Vydac 5-μm-particle-size Phenyl column and the TEAP buffer system. In the TFA system, buffer A contains 1 ml trifluoroacetic acid in 999 ml water and buffer B is 1 ml trifluoroacetic acid in 199 ml water and 800 ml acetonitrile. The two inhibin species elute separately. Inhibin accumulated from a few batches was concentrated by RP-HPLC using a 0.46×25 cm Aquapore RF-300 10 μm-particle-size column (Brownlee Labs., Santa Clara, Calif.) and the TFA buffer system. Ordinarily, however, this purification step will not be used with cell-culture supernatants from transformants with DNA encoding only the $β_A$ or $β_B$ chains.

Inhibin, activin, prodomain sequences or their variants are administered in the form of pharmaceutically acceptable nontoxic salts, such as acid addition salts or metal complexes, e.g., with zinc, iron or the like (which are considered as salts for purposes of this application). Illustrative of such acid addition salts are hydrochloride, hydrobromide, sulphate, phosphate, maleate, acetate, citrate, benzoate, succinate, malate, ascorbate, tartrate and the like. Intravenous administration in isotonic saline, phosphate buffer solutions or the like is suitable.

The polypeptide herein should be administered under the guidance of a physician, and pharmaceutical compositions will usually contain an effective amount of the peptide in conjunction with a conventional, pharmaceutically-acceptable carrier. The dosage will vary depending upon the specific purpose for which the protein is being administered, and dosage levels in the range of about 0.1 to about 1 milligram per Kg. of body weight may be used when inhibin is administered on a regular basis as a male contraceptive.

Inhibin, activin, prodomain sequences or their variants desirably are administered from an implantable or skin-adhesive sustained-release article. Examples of suitable systems include copolymers of L-glutamic acid and gamma ethyl-L-glutamate (U. Sidman et al., 1983, "Biopolymers" 22(1): 547–556), poly (2-hydroxyethyl-methacrylate) (R. Langer et al., 1981, "J. Biomed. Mater. Res." 15: 167–277 and R. Langer, 1982, "Chem. Tech." 12: 98–105) ethylene vinyl acetate (R. Langer et al., Id.), or poly-D-(–)- 3-hydroxybutyric acid (EP 133,988A). Such articles are implanted subcutaneously or are placed into contact with the skin or mucous membrane.

In order to simplify the Examples certain frequently occurring methods will be referenced by shorthand phrases.

Plasmids are designated by a low case p preceded and/or followed by capital letters and/or numbers. The starting plasmids herein are commercially available, are publicly available on an unrestricted basis, or can be constructed from publicly available plasmids or DNA in accord with published procedures. In addition, other equivalent plasmids are known in the art and will be apparent to the ordinary artisan.

"Digestion" of DNA refers to catalytic cleavage of the DNA with an enzyme that acts only at certain locations in the DNA. Such enzymes are called restriction enzymes, and the sites for which each is specific is called a restriction site. "Partial" digestion refers to incomplete digestion by a restriction enzyme, i.e., conditions are chosen that result in cleavage of some but not all of the sites for a given restriction endonuclease in a DNA substrate. The various restriction enzymes used herein are commercially available and their reaction conditions, cofactors and other requirements as established by the enzyme suppliers were used. Restriction enzymes commonly are designated by abbreviations composed of a capital letter followed by other letters and the, generally, a number representing the microorganism from which each restriction enzyme originally was obtained. In general, about 1 μg of plasmid or DNA fragment is used with about 1 unit of enzyme in about 20 μl of buffer solution. Appropriate buffers and substrate amounts for particular restriction enzymes are specified by the manufacturer. Incubation times of about 1 hour at 37° C. are ordinarily used, but may vary in accordance with the supplier's instructions. After incubation, protein is removed by extraction with phenol and chloroform, and the digested nucleic acid is recovered from the aqueous fraction by precipitation with ethanol. Digestion with a restriction enzyme infrequently is followed with bacterial alkaline phosphatase hydrolysis of the terminal 5' phosphates to prevent the two restriction cleaved ends of a DNA fragment from "circularizing" or forming a closed loop that would impede insertion of another DNA fragment at the restriction site. Unless otherwise state, digestion of plasmids is not followed by 5' terminal dephosphorylation. Procedures and reagents for dephosphorylation are conventional (T. Maniatis et al., 1982, *Molecular Cloning* pp. 133–134).

"Recovery" or "isolation" of a given fragment of DNA from a restriction digest means separation of the digest on polyacrylamide gel electrophoresis, identification of the fragment of interest by comparison of its mobility versus that of marker DNA fragments of known molecular weight, removal of the gel section containing the desired fragment, and separation of the gel from DNA. This procedure is known generally. For example, see R. Lawn et al., 1981, "Nucleic Acids Res." 9: 6103–6114, and D. Goeddel et al., 1980, "Nucleic Acids Res." 8: 4057.

"Southern Analysis" is a method by which the presence of DNA sequences in a digest or DNA-containing composition is confirmed by hybridization to a know, labelled oligonucleotide or DNA fragment. For the purposes herein, unless otherwise provided, Southern analysis shall mean separation of digests on 1 percent agarose, denaturation and transfer to nitrocellulose by the method of E. Southern, 1975, "J. Mol. Biol." 98: 503–517, and hybridization as described by T. Maniatis et al., 1978, "Cell" 15: 687–701.

"Transformation" means introducing DNA into an organism so that the DNA is replicable, either as an extrachromosomal element of chromosomal integrant. Unless otherwise provided, the method used herein for transformation of *E. coli* is the $CaCl_2$ method of Mandel et al., 1970, "J. Mol. Biol." 53: 154.

"Ligation" refers to the process of forming phosphodiester bonds between two double stranded nucleic acid fragments (T. Maniatis et al., Id., p. 146). Unless otherwise provided, ligation may be accomplished using known buffers and conditions with 10 units of T4 DNA ligase ("ligase") per 0.5 μg of approximately equimolar amounts of the DNA fragments to be ligated.

"Preparation" of DNA from transformants means isolating plasmid DNA from microbial culture. Unless otherwise provided, the alkaline/SDS method of Maniatis et al., Id. p. 90., may be used.

"Oligonucleotides" are short length single or double stranded polydeoxynucleotides which are chemically synthesized by known methods and then purified on polyacrylamide gels.

All citations are expressly incorporated by reference.

EXAMPLE 1

Isolation Of Cloned Inhibin α-Subunit cDNAs

The strategy for identification of clones containing coding sequences for the porcine inhibin subunits was based on the "long-probe" approach, successful in some previous instances (Anderson et al., 1983, "Proc. Nat. Acad. Sci. U.S.A." 80:6836–6842 and Ullrich et al., 1984, "Nature" 309:418–425). Briefly, a high-complexity cDNA library constructed in λgt10 and derived from porcine ovarian mRNA by oligo-dT-primed cDNA synthesis was screened with a single 64-base-line synthetic oligodeoxynucleotide directed against the N-terminal amino acid sequence of the α-chain of porcine inhibin. It was found that the library is to be prepared from fresh ovarian tissue because the inhibin chain mRNA was apparently quite labile. Approximately 1 in 2,000 plaques hybridized with this probe, and sequence analysis of several hybridizing cloned cDNAs confirmed correct probe identification. This analysis revealed that none of the characterized cDNAs contained sufficient sequence information to predict the complete structure of the αchain precursor protein. Rather than analyzing more clones from the same cDNA library, a second library was constructed by 3' extension on ovarian mRNA of a synthetic oligodeoxynucleotide complementary to a sequenced region encoding α precursor residues 60–64 (FIG. 1A). This library was screened with a suitable restriction fragment from a previously analyzed cDNA and yielded several isolates which specified the remainder of the DNA sequences encoding the N-terminal region of the α precursor. Completeness of the coding sequence was judged from the presence of a long reading frame which specifies the porcine α-chain peptide sequence and starts with a methionine codon preceded by an in-frame stop codon and followed by a hydrophobic sequence bearing the hallmarks of a signal peptide. The full sequences for the precursor protein and its cDNA are shown in FIG. 1B. The complete protein including signal peptide has an Mr of ¯40K consisting of 364 amino acids, of which the C-terminal 134 ($M_r$ ¯14.5K) constitute the porcine inhibin α-chain. There are several Arg-Arg sequences in the proregion of the precursor, one of them directly preceding the α subunit. We believe that this latter pair of basic residues is the processing site for the proteolytic release of the α peptide. The deduced precursor sequence predicts two N-linked glycosylation sites, one within the α chain proper.

In addition to the coding region, the cDNA sequence contains a 3'-untranslated sequence of 167 nucleotides, including the canonical AATAAA polyadenylation signal, and a 5'-untranslated region, the proper length of which is presently unknown.

The detailed method was as follows:

Polyadenylated mRNA was prepared from freshly frozen porcine ovaries (Kaplan et al., "J. Biochem." 183: 181–184). An oligo-dT-primed cDNA library of ¯6×10⁶ clones in λgt10 (Huynh et al., 1984, *DNA Cloning Techniques*, Ed. D. Clover) was prepared from 5 µg polyA+ mRNA as described by Wood et al., "Nature" 312: 330–337 (1984), except that the EcoRI adaptors used had the sequence

| | |
|---|---|
| 5'-AATTCACTCGAGACGC-3' | (SEQ ID NO. 15) |
| 3'-GTGAGCTCTGCG-5'P. | (SEQ ID NO. 16) |

Approximately 1×10⁶ unamplified cDNA clones were screened with 5 α-subunit oligonucleotide 5'-ACCGC-CCCTTTGCCTTGGCCTTGGTCCCCTGCT-GCTCTGAGACTGCTGCAGAGACCTCCTGAGG- 3' (SEQ ID NO. 17), based on the amino acid sequence underlined in FIG. 1B. Hybridization was carried out with the phosphorylated ³²P-labelled probe in 5×SSC, 40% formamide at 37° C. Filters were washed at 50° C. with 1×SSC, 0.1% SDS. Approximately 500 hybridization positive clones were obtained, twelve of which were purified and examined for insert size. The EcoR1 inserts of five of these (λPIN-α2, −α5A, −α5, −α9, −α10) were subcloned into M13 derivatives (Messing et al., 1981 "Nucl. Acids Res." 9:309–321) and sequenced by the dideoxy chain termination method of Sanger et al., "Proc. Nat. Acad. Sci. U.S.A." 74:5463–5467 (1977). A specifically primed library was prepared by priming 5 µg of polyA⁺ mRNA with the oligonucleotide 5'-CCCCACAGCATGTCTT-3' (SEQ ID NO. 18) (complementary to nucleotides 248–263) and subsequent cloning into λgt10. Approximately 2×10⁵ clones of the 1×10⁶ clones obtained were screened with the 5' 100 bp EcoRI-BamHI fragment prepared from λPIN-α2. Twelve of the 170 hybridization positive clones obtained were purified and two (λPIN-S12s, −S4s) were sequenced by the dideoxy method. The complete nucleotide sequences of the α-subunit cDNAs were obtained by subcloning various restriction fragments from the different λ isolates into the M13 phage derivatives. Compressions were resolved by the use of deoxyinosine mixes in combination with the *E. coli* single stranded binding protein (Pharmacia).

Isolation of Cloned Inhibin β Subunit cDNAS

Figure 2A:
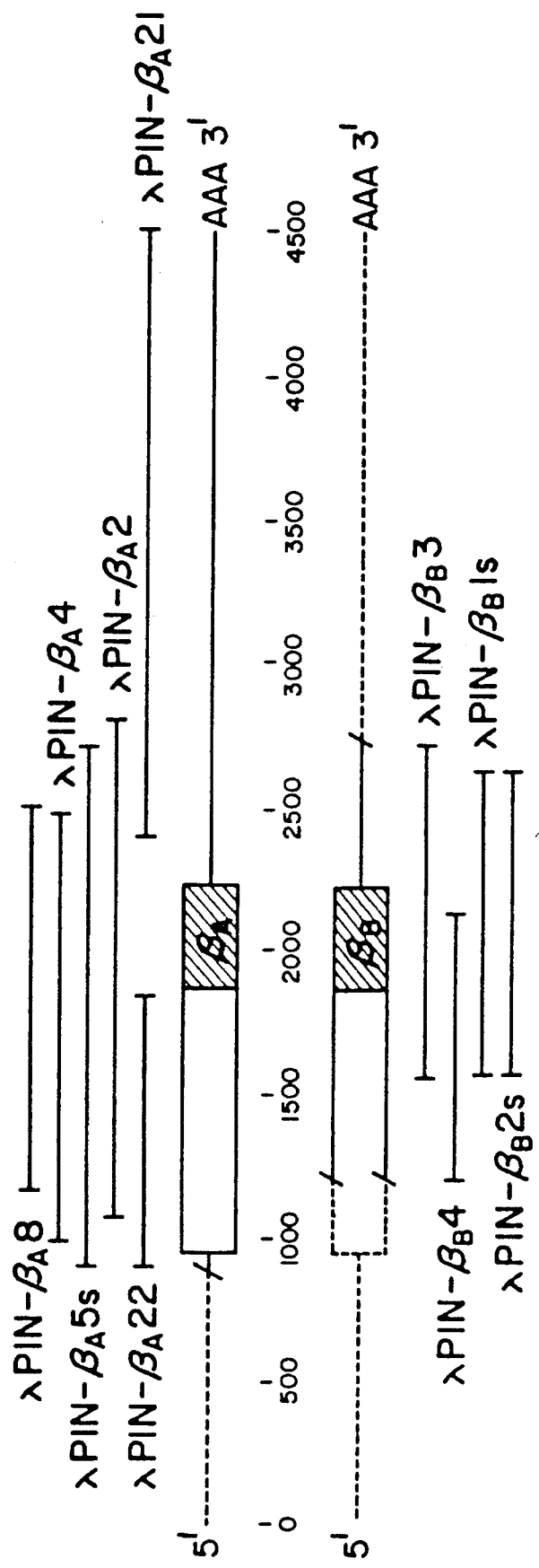
FIG. 2A is a schematic representation of the porcine $β_A$ and $β_B$ subunit mRNAs with coding sequences boxed. The $β_A$ and $β_B$ subunits (dashed) are encoded towards the 3' end of the coding sequences. The 3' and 5' untranslated regions are shown as a line. The length of the 5' and 3' untranslated region of the βB subunit mRNA is inferred from the size of the mRNA (FIG. 3) and its obvious similarity to the $β_A$ mRNA. Tentative regions of the cDNAs are shown as dashes in the diagram. The relative positions of the overlapping oligo-dT primed cDNA clones and the randomly primed clones (λPIN$β_A$5s, λPIN$β_B$1s, and λPIN$β_B$2s) are indicated. The scale is in nucleotides from the 5' end of the 4.5 kb mRNA.

The cDNA sequences encoding the precursors of the inhibin β subunits were obtained from the same cDNA libraries used for the α subunit. Overlapping cDNA clones were isolated by screening first with single long synthetic oligodeoxynucleotide probes based on the two N-terminal β subunit sequences and subsequently with suitable restriction fragments derived from characterized cDNA clones which served as probes for "walking" in both 5' and 3' directions (FIG. 2A).

In more detail, approximately 2×10⁵ oligo-dT primed ovarian cDNA clones were screened with the 5' end labelled $β_A$ oligonucleotide, 5'-AAGAAGCAGTTCTTTGTGTCCT-TCAAGGACATTGGCTGGAATGACTGGATCATTGC-3' (SEQ ID NO. 19) based on the amino acid sequence of residues 321–339. Five hybridization positives were obtained, of which three proved to contain $β_A$ coding sequences (λPIN-βA2, −$β_A$4, −$β_A$8). A 5' end 154 bp EcoRI-HindIII (nucleotides 158–297) fragment and a 3' end 213 bp EcoRI-Pst fragment (nucleotides 1679–1892) derived from λPINβ$_A$2 were used to screen 2×10⁶ oligo-dT primed cDNA clones and 2×10⁵ clones from the α-chain specifically primed library. Out of the sixteen clones analyzed in detail two were found to have longer 5' ends (λPIN-β$_A$5s, −β$_A$22) and one clone λPIN-β$_A$21 contained the entire 3'-untranslated region. Porcine inhibin β$_B$ subunit cDNA clones were isolated by screening 2×10⁵ clones from the specifically primed library with the β$_B$ oligonucleotide 5'-GGCCTG-GAGTGTGATGGGAGAACCAACCTGTCCT-GCCGCCAGGAATTTTTCATCGATTTCAGGCT- 3'

(SEQ ID NO. 20), which was based on the NH$_2$-terminal sequence described in FIG. 1A. Positive clones were further screened with the oligonucleotide inosine probe 5'-AAITC-TATIAAIAA$_C^T$TG$_C^T$-3' (SEQ ID NOS. 21, 22, 23, and 24, respectively) ("I" in this sequence stands for inosine), which covers all the possibilities in the non-coding strand for the amino acid sequence QQFFIDF (SEQ ID NO. 25). Two clones (λPINβ$_B$-1s, -2s) were isolated and sequenced and found to code for the β$_B$ subunit. A 230 bp EcoRI-Sma (nucleotides 21–251)fragment was isolated from λPINβ$_B$-I and used as a hybridization probe to screen 2×10$^6$ oligo-dT primed cDNA clones. Two positives were obtained (λPINβ$_B$-3,4). The nucleotide sequence of these overlapping clones was used to construct the sequence shown. All sequences were obtained by subcloning specific fragments into M13 phage vectors (Messing et al., op cit.). The EcoRI restriction sites referred to above are all contained within the cDNA adaptor fragment, and do not refer to sequences present in the cDNA.

We noted that only very few clones from the oligo-dT-primed library (4 out of 2×10$^5$) hybridized with the synthetic probe for the β-subunit of inhibin A. Although most of these proved correct by DNA sequence analysis, none contained a full 3'-untranslated region, as judged by the absence of a polyA homopolymer at their 3' ends. Absence of polyA tails suggested the existence of a very long 3'-untranslated sequence in this mRNA species and/or structural region(s) which prove difficult to copy by the polymerases used for library construction. Unexpectedly, a higher abundance (~10-fold) of inhibin β$_A$ subunit coding sequences was found in the cDNA library made by specific priming on α-subunit mRNA. This library was screened with the synthetic probe for the β-chain of inhibin A on the subsequently refuted theory that the α precursor mRNA might also encode the β subunit. The high abundance of inhibin β$_A$ cDNA in this library was later traced to fortuitous complementarity of the specific α chain primer to a region in the 3'-untranslated portion of the corresponding mRNA.

Only four cloned cDNAs encoding the β subunit of inhibin B were found in our libraries. The sequence information obtained from these clones failed to reveal the complete structure of the corresponding precursor protein and its cDNA. The sequences of cDNAs and deduced protein structures for the precursors of the β subunits are compared in FIG. 2B. The nucleotide sequence of inhibin β$_A$ subunit cDNA is 3.6 kb in length and contains an open reading frame for a protein of 425 amino acids (Mr ~46K), the C-terminal 116 residues of which represent the β subunit proper (Mr ~13K). This reading frame begins with a methionine codon followed by a sequence that codes for a characteristic signal peptide, the true length of which is believed to be 29 residues. The encoded β subunit is preceded by a string of 5 arginines at which it is presumably proteolytically cleaved from the precursor. Similar to the α subunit precursor, this β precursor contains several additional pairs of basic residues at which hitherto unknown biologically active peptide entities are believed to be released. It also contains one possible site for N-linked glycosylation in the proregion (Asn, residue (165).

The deduced protein sequence for the β subunit of inhibin B shows high homology with the β$_A$ subunit sequence. 71 amino acid residues are identical and most changes are conservative in nature. Sequence homology, although of a lesser degree, is also found in the proregion of both β subunit precursors. Interestingly, an extremely purine-rich sequence rarely seen in coding regions by present in the cDNA encoding the inhibin β$_A$ precursor and resulting in a curious amino acid sequence is not found in the cDNA which codes for the homologous β$_B$ precursor. This results in a gap of 22 amino acid residues from the β$_B$ precursor of inhibin when protein sequences are aligned for maximal homology. Such alignment also brings about a perfect match in the cysteine positions of both precursors (see FIG. 2B).

Northern Analysis of α and β chain Precursor mRNAs

Ovarian total and polyadenylated RNAs were analyzed by the Northern procedure using the sequenced cDNAs as probes to assess size and relative abundance of the mRNAs which encode the peptide subunits α and β and β$_B$ of the heterodimeric inhibin molecule. Polyadenylated mRNA (2μg: lanes a, b, c, and f; 8 μg: lane d) and total RNA (10 μg: lanes e and g) were electrophoresed into a formaldehyde 1.2% agarose gel and blotted onto nitrocellulose filters. The following $^{32}$P-labelled cDNA fragments were used as hybridization probes under stringent conditions. Lane a: 240 bp EcoRI-SmaI (nucleotides 134–371) from a subunit cDNA; b: 154 pb EcoRI-HindIII (nucleotides 158–297) from βA subunit cDNA; c: 230 bp EcoRI-Sma (nucleotides 21–251) from β$_B$ subunit cDNA; d and e: EcoRI insert of λPIN-α2; f and g: EcoRI insert of λPIN-β$_A$5. Filters were washed for 2 hours with 3 changes of 0.1×SSC, 0.1% SDS at 60° C.

Analysis showed (FIG. 3) that α and β mRNAs are of different size and abundance, as indicated by results obtained from cDNA cloning. From their respective band intensities the α precursor mRNA is estimated to be at least of 10-fold higher abundance than the mRNA for the β$_A$ precursor, and approximately 20-fold higher than the mRNA for the β$_B$ precursor.

Figures 2, 2B, 3:
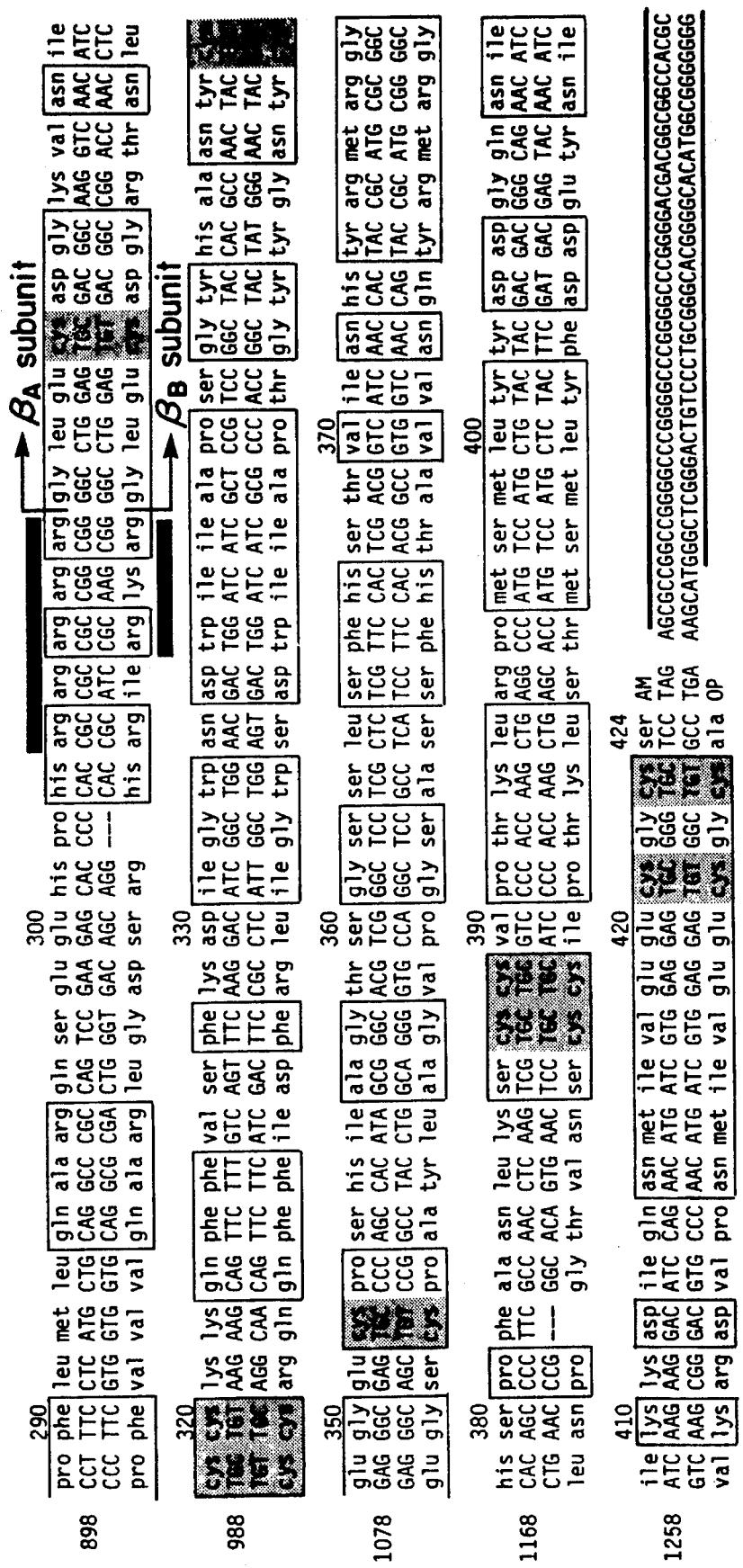
FIG. 2B is the nucleotide sequence and deduced amino acid sequence of the porcine inhibin β-subunit precursors (SEQ ID NOS. 32 and 31, respectively, for the $β_A$ nucleotide and amino acid sequences, and SEQ ID NOS. 34 and 33, respectively, for the $β_B$ nucleotide and amino acid sequences). The $β_B$ sequence is aligned with the $β_A$ sequence for maximum homology. The $NH_2$-termini of the β-subunit precursors are indicated by bracket and arrows. Cysteine residues are shaded, possible processing sites are indicated by open bars, and a potential glycosylation site is shown by the cross-hatched box. A very GC-rich region present 3' to the termination codon intron sequences is underlined and overlined in both sequences. Amino acid sequences used to design oligonucleotide probes are underlined, as is the AATAAA polyadenylation signal. There was one nucleotide difference between λPIN-$β_A$8 and other clones covering this area. A G-to-A change causes a change of amino acid 278 from a glycine to a serine. The proteolytic processing site Arg Arg Arg Arg Arg (SEQ ID NO. 4) (black bar) immediately precedes the $NH_2$ terminus of the mature $β_A$ subunit, with the prosequences located upstream. The amino acids for the $β_A$ subunit only are numbered.
FIG. 3 is a Northern blot analysis of porcine ovarian mRNA with α, $β_A$ and $β_B$ subunit cDNA hybridization probes. Lanes a, b, c, d, and f are polyA$^+$ mRNA and e and g are total RNA. The position of the 28S and 18S ribosomal RNAs are shown. Lanes, a, d, and e were hybridized with an α-subunit cDNA probe; lanes d, e and g with a $β_A$ subunit specific probe, and lane c with a $β_B$ subunit specific probe. The α-subunit mRNA is approximately 1.5 kb, the $β_A$ subunit mRNAs are approximately 4.5 kb. The hybridizations shown in lanes a, b, and c were performed with probes of approximately equal length and specific activity in order to judge relative mRNA levels.
Figure 3:
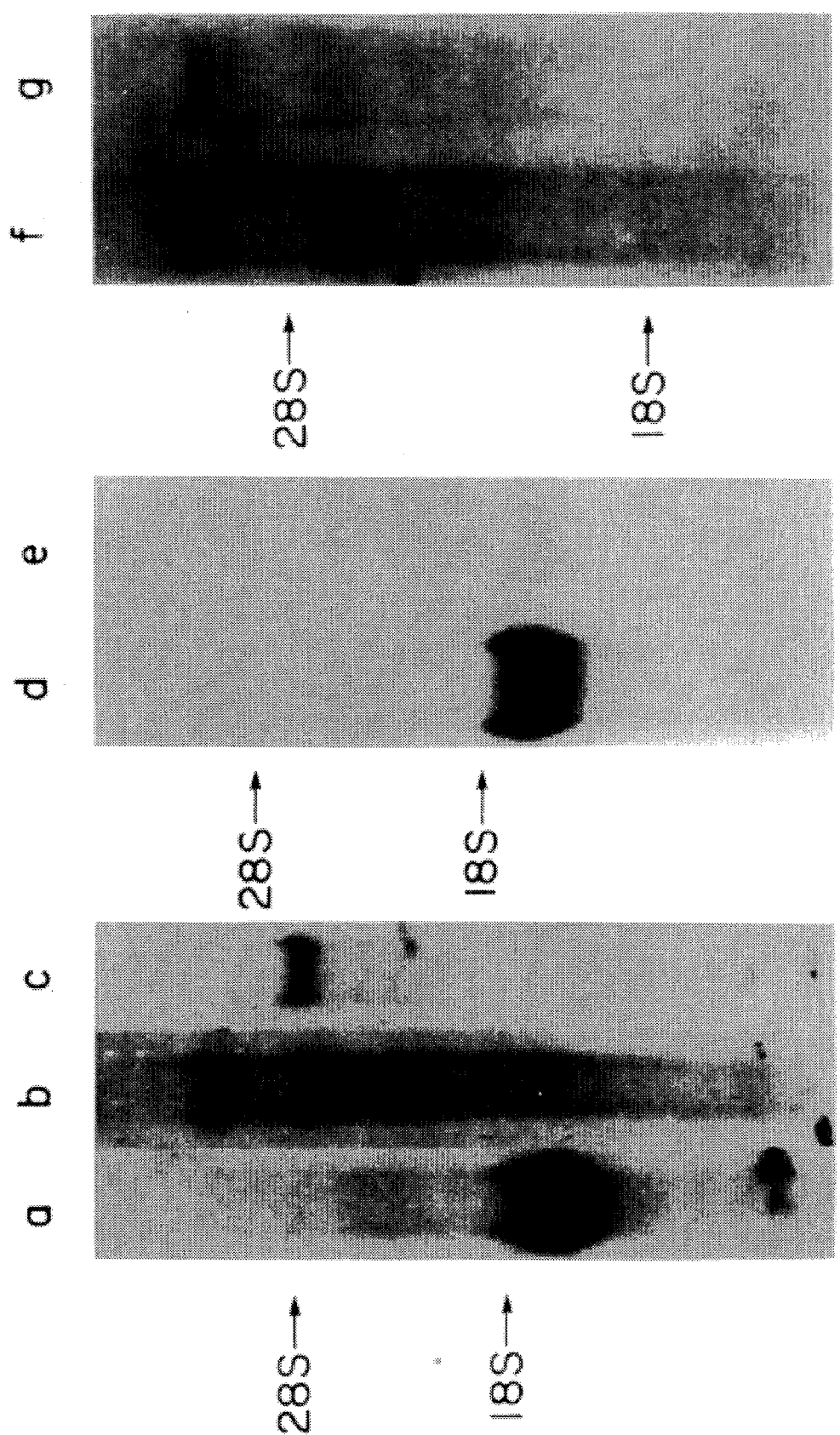

Using ribosomal RNAs as size standards, the α precursor mRNA, which is a single species, is ~1500 nucleotides in length, a size in good agreement with the cloned cDNA sequence (FIG. 1B). β$_A$ precursor mRNA sequences are represented by two main species of ~4.5 and ~7.2 kb in length. The relatively higher intensity of both species in polyadenylated than total RNA suggests that the 4.5 kb species does not represent 28S RNA which hybridized to the cDNA probe. Thus, the β precursor cDNA sequences shown in FIG. 2B are thought to represent the 4.5 kb mRNA, suggesting that the 5' untranslated region for the β$_A$ mRNA is approximately 900 nucleotides long. The β$_B$ precursor is encoded on one mRNA, of approximately 4.5 kb in size, which is present at roughly half the level of the two β$_A$ mRNAs. Since the two β mRNAs are closely related, one can predict that both mRNAs have a similar structure and thus the β$_B$ mRNA presumably possesses a long 5' and 3' untranslated region equivalent to that shown for the β$_A$ mRNA. Choice of a different polyadenylation signal might explain the existence of the 7.2 kb species.

Homology To Transforming Growth Factor-β

The mature α and β inhibin subunits contain seven and nine cysteine residues respective. Upon alignment of the cysteine residues, it is apparent that the two subunits share a similar cysteine distribution and some sequence homology exists around these residues (FIG. 4), suggesting that both types of subunits derive from one ancestral gene. Surprisingly, significant homology was found between the β chain and the primary structure of human TGF-β recently determined. As outlined in FIG. 4, both peptides are of nearly equal length (inhibin β$_A$ subunit, 116; β$_B$ subunit 115; TGFS, 116 residues) and show a strikingly similar distribution of their nine cysteine residues. Using this cysteine "skeleton" for alignment, the $\beta_A$ and TGF-$\beta$ sequences have an additional 31 residues in identical positions and show conservative changes in nine homologous places. Similar high homologies are seen upon comparison of the $\beta_B$ and $\beta$-TGF. Some gaps were introduced for better alignment (FIG. 4). The overall homology reaches 35%, but approaches 60% in certain sections (cf. porcine inhibin $\beta_A$ chain residues 11–45 and TGF residues 15–49), a very high degree of homology considering the difference in species. Interestingly, this homology extends beyond the termination codon for protein synthesis in the respective cDNAs. Thus, the cDNAs for TGF-$\beta$ and both inhibin $\beta$ subunits contain a highly G and C rich sequence in this region, and they also possess unusually long 5' and 3' untranslated regions.

One can discount the suggestion that the $\beta$ subunit of inhibin is the porcine equivalent of human TGF-$\beta$, since there is almost absolute homology between human and murine $\beta$-TGFs. These findings strongly indicate that both inhibin subunits and TGF-$\beta$ have a common ancestor and belong to one gene family. All three peptides are derived from similarly-sized precursors ($M_r$ ~40K) where they occupy the C-terminal 110 or so residues and are released by proteolytic cleavage at pairs of arginines. They form homo- or heterodimers, and subunits in the biologically active complex are linked by disulfide bridges. However, there is little sequence homology between TGF-$\beta$ and the $\beta$ subunits in the pro parts of their precursors, although the regions comprising the odd residues which precede the $\beta$ subunit and TGF peptides display limited but significant sequence relatedness.

EXAMPLE 2

Recombinant Synthesis of Porcine Inhibin

Figure 5A:
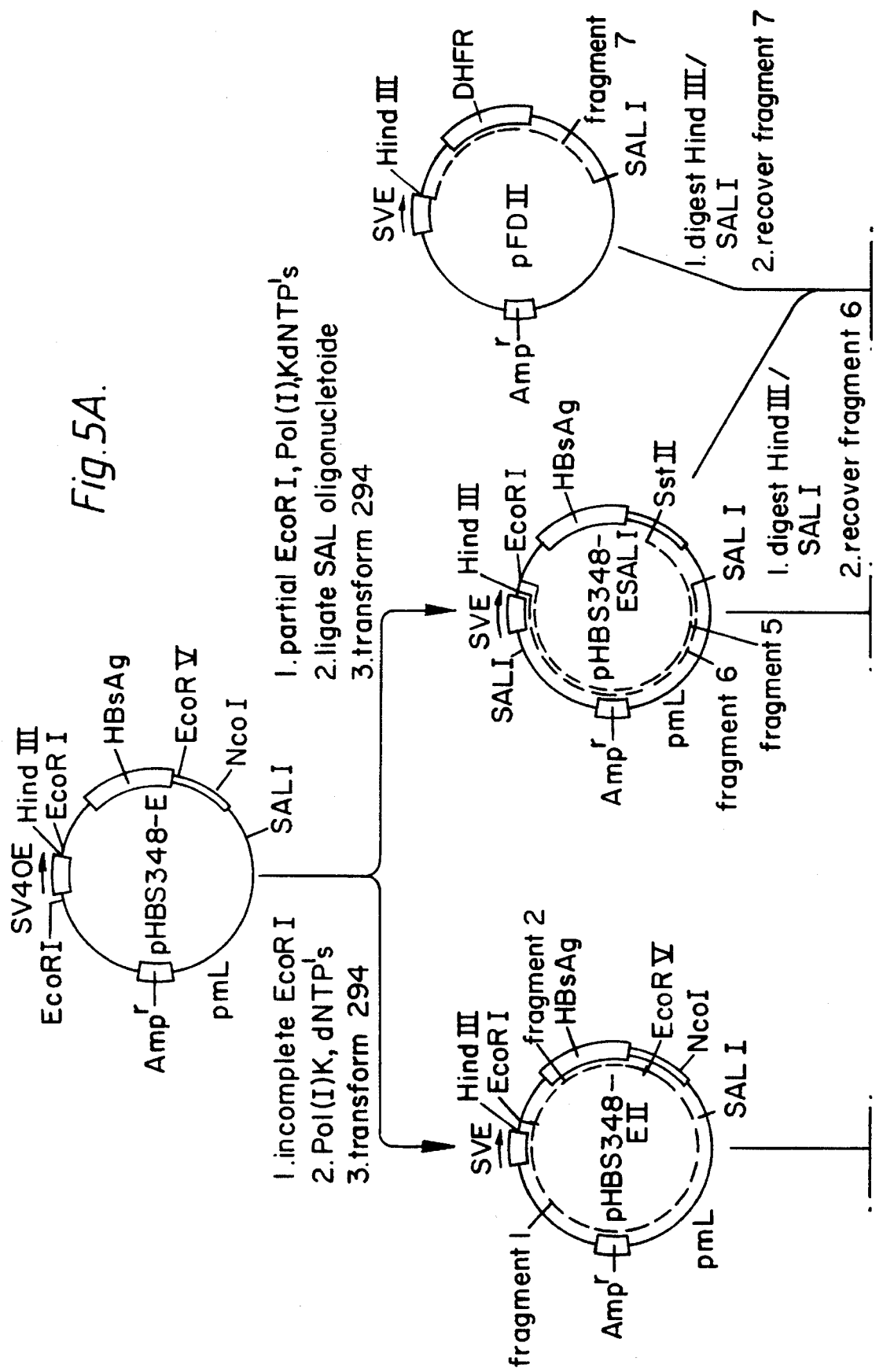
FIG. 5 depicts the construction of a representative recombinant expression plasmid for porcine inhibin.
Figure 5B:
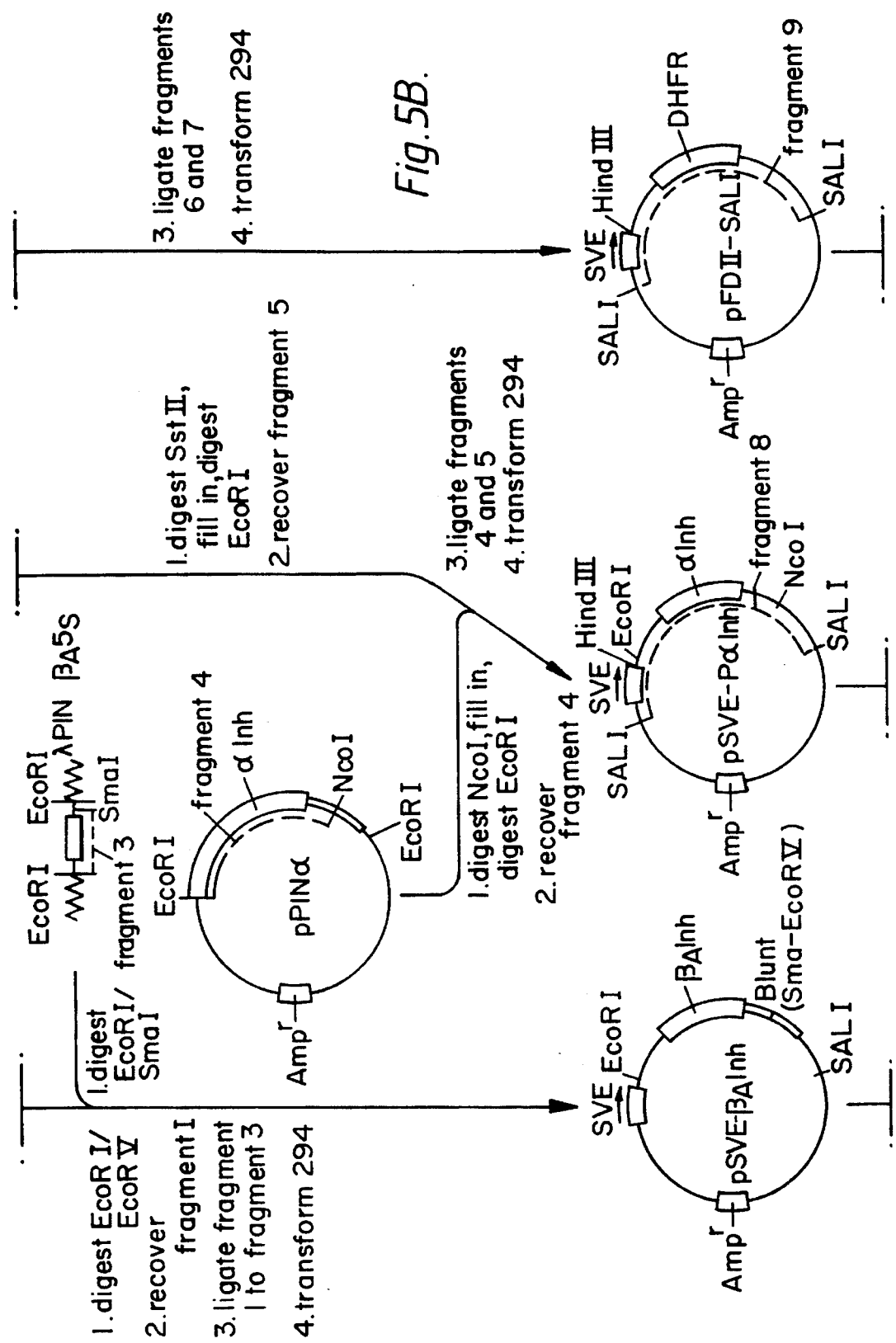
Figure 5C:
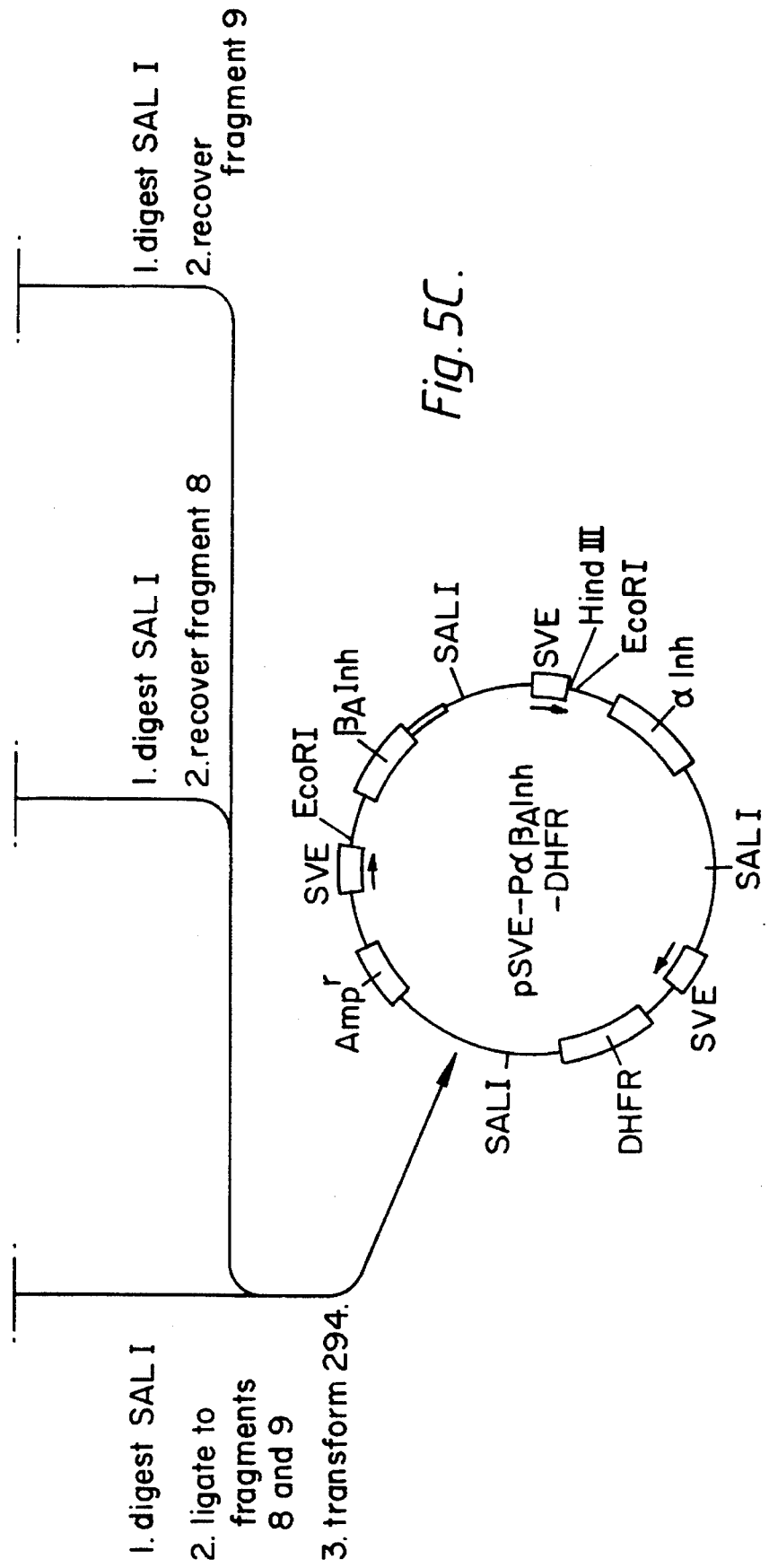

The plasmid used for recombinant synthesis of porcine inhibin was pSVE-P$\alpha\beta_A$Inh-DHFR. The procedure to construct this plasmid is shown in FIG. 5. This plasmid was constructed as follows:

pHBS348-E (EP 0073656A) was partially digested with EcoRI, blunted with E. coli DNA polymerase I (Klenow fragment) and the four dNTPs, ligated and the ligation mixture was transformed into E. coli in 294 mm (ATCC 31446). The transformed culture was plated on ampicillin media plates and resistant colonies were selected. Plasmids are screened for the loss of the EcoRI site preceding the SV40 early promoter. A plasmid having the site deleted is referred to as pHBS348-EII.

pHBS348-EII was digested with EcoRI and EcoRI to produce two fragments, fragment I containing the SV40 early promoter, pmL-Amp$^r$ sequences and the HbsAg 3' untranslated region and fragment 2 containing the HBsAg (hepatitis B antigen) coding sequence.

$\lambda$PIN$\beta_A$5$_S$ containing the coding region for the porcine inhibin $\beta_A$ subunit was digested with EcoRI and SmaI and the 1335 bp fragment (fragment 3) containing the $\beta_A$ coding region recovered by polyacrylamide gel electrophoresis. Fragment I, recovered by agarose gel electrophoresis, was ligated to fragment 3 and the ligation mixture transformed into E. coli strain 294 (ATCC 31446). The transformed culture was plated on ampicillin media plates and resistant colonies were selected. Plasmid DNA was prepared from transformants and checked by restriction analysis for the presence of the correct DNA fragments. This plasmid is referred to as pSVE-p$\beta_A$Inh.

pHBS348-E (EP 0073656A) was partially digested with EcoRI, blunted with E. coli DNA polymerase I (Klenow fragment) and the four dNTPs, and ligated to the synthetic oligonucleotide 5' GGTCGACC-3' containing the SalI recognition site. The transformed culture was plated on ampicillin media plates and resistant colonies were selected. Plasmids were screened for the presence of the extra SalI restriction site. Plasmid DNA is prepared from this construction (pHBS348-ESalI).

$\lambda$PIN$\alpha$-12s and $\lambda$PIN$\alpha$-2 were digested with EcoRI and BamHI. A 104 bpEcoRI-BamHI fragment from $\lambda$PIN$\alpha$-12s containing the 5' coding region and a 1246 bp EcoRI-BamHI fragment from $\lambda$PIN$\alpha$-2 containing the middle and 3' coding region were recovered and ligated together. The ligation mixture was digested with EcoRI, the enzyme heat denatured, and the mixture ligated to EcoRI-digested pUC9 (BRL). Recombinants were selected and confirmed by restriction analysis. DNA was prepared from the correct plasmid (pPIN$\alpha$).

pPIN$\alpha$, containing the complete coding region for porcine $\alpha$-inhibin was digested with NcoI and EcoRI, filled in by Pol(I)K in the presence of 4dNTP's, and the 1280 bp fragment (fragment 4) was recovered by gel electrophoresis. pHBS348-ESalI was digested with SstII and HindIII, filled in by Pol(I)K in the presence of 4dNTP's, and fragment 5 containing the PML-Amp$^r$ region, SV40 early promoter and HBsAg 3' untranslated region was recovered by gel electrophoresis. Fragments 4 and 5 were ligated together and the ligation mixture was used to transform E. coli 294 (ATCC 31446). Recombinants were selected by growing on Ampicillin media plates. The desired recombinant is called pSVE-P$\alpha$Inh.

pHBS348-ESalI was digested with SalI and HindIII and fragment 6 containing the pML-Amp$^r$, and SV40 early promoter was recovered by gel electrophoresis. pFD II (EP 117,060A) was digested with SalI and HindIII and fragment 7 was recovered which contains the normal mouse DHFR gene fused to the HBsAg 3' untranslated region. Fragments 6 and 7 were ligated, and the ligation mixture was transformed into E. coli strain 294 (ATCC 31446). The transformed culture was plated on ampicillin media plates and resistant colonies were selected. Plasmid DNA was prepared from transformants and checked by restriction analysis for the presence of the correct DNA fragments. This construction is referred to as pFDII-SalI.

pSVE-P$\alpha$Inh was digested with SalI and fragment 8 was recovered which contains the SV40 early promoter and the $\alpha$-inhibin coding region fused to the HBsAg 3'-untranslated region. pFDII-SalI was digested with SalI and fragment 9 containing the SV40 early promoter and the mouse DHFR coding region linked to the HBsAg 3'-untranslated region was recovered. pSVE-$\beta_A$Inh was linearized by SalI digestion and ligated to fragments 8 and 9 in a three part ligation. The ligation mixture was transformed into E. coli strain 294 (ATCC 31446). The transformed culture was plated on ampicillin media plates and resistant colonies were selected. Transformants were screened for the presence of fragments 8 and 9 in the correct orientation such that transcription from the three SV40 early promoters will proceed in the same direction. This final plasmid is designated pSVE-P$\alpha\beta_A$Inh-DHFR.

Plasmid pSVE-P$\alpha\beta_A$Inh-DHFR was transfected into DHFR deficient CHO cells (Urlaub and Chasin, 1980, PNAS 77,4216–4220). However, any DHFR$^-$ mammalian host cell is suitable for use with this plasmid. Alternatively, any mammalian host cell is useful when the host cell is cotransformed with a plasmid encoding neomycin resistance, and transformants identified by their ability to grow in neomycin-containing medium.

The transfected CHO cells were selected by culturing in 15 HGT⁻ medium. The cells were allowed to grow to confluency in 15 cm diameter plates. The cells thereafter were cultured in serum free medium for 48 hours prior to harvest. 50 ml of supernatant medium was lyophilized after the addition of 100 mg human serum albumin. The residue was redissolved in 3 ml 1% fetal bovine serum in HDMEM (GIBCO Laboratories, Santa Clara, Calif.), filtered through a Millex-GS 0.22 mM filter (Millipore Corp., Bedford, Mass.) and assayed in duplicate.

The inhibin hormonal activity in the transformant supernatants was determined by an in vitro bioassay using rat anterior pituitary monolayer culture, Vale, W. et al. *Endocrinology*, 91, 562–572 (1972). In brief, 21-day-old female rat anterior pituitaries were collected, enzymatically dispersed and plated in 10% fetal bovine serum in HDMEM (GIBCO Laboratories, Santa Clara, Calif.) into 24-well tissue culture plates (Falcon Plastic, Oxnard, Calif.) on day 1. On day 2, the medium was changed to 1% fetal bovine serum in HDMEM, and the transformant medium sample was added. Incubation was continued for another 48 hours. The monolayer medium was then harvested, and the LH and FSH contents were determined by radio-immunoassay (RIA) using materials provided by The Pituitary Hormone Program of NIADDKD. In this assay, the inhibin-containing CHO cell culture inhibits the basal release of FSH but not LH, as compared to control pituitary cells that received the incubation medium only. The amount of porcine inhibin detected in transformant supernatants was 20 ng/ml and exhibited a dose response curve parallel to that obtained with pure porcine ovarian inhibin.

Immunological cross-reactivity is assayed by a sandwich-type radioimmunoassay. Rabbit antisera are raised against purified porcine follicular inhibin by s.c. immunization of rabbits with the porcine inhibin in Freund's complete adjuvant. The presence of anti-inhibin in the antiserum is detected by incubation of the antiserum with purified porcine inhibin and assaying for the formation of an immune complex by conventional techniques, e.g. gel filtration. An aliquot of the antisera is coated onto goat-anti-rabbit IgG precoated polystyrene test tubes. The recombinant culture supernatant or extract is diluted into phosphate buffered saline and added to the coated tubes, incubated overnight and washed. Another aliquot of the rabbit antiserum is added to the test tubes, incubated and washed. Radioiodinated goat antirabbit IgG is added to the tubes, incubated and unbound goat antiserum removed by washing. The recombinantly produced inhibin cross-reacts with the rabbit antiserum, as evidenced by bound counts on the test tubes which exceed those of controls incubated with culture medium or extracts from untransformed host cells.

EXAMPLE 3

Construction of Human Inhibin Vector and Expression of Human Inhibin in Recombinant Cell Culture-I Expression of human inhibin $\alpha\beta_A$ is facilitated by the discovery that the mature porcine and human $\beta_A$ chains are identical. Thus, construction of a vector for the expression of human inhibin can proceed from plasmid pSVE-$\beta_A$-Inh from Example 1, which contains the porcine $\beta_A$-encoding cDNA.

A λgt 10 library of human ovarian cDNA made from 10 μg of ovarian mRNA was subjected to Southern analysis using radiophosphate labelled porcine cDNA encoding α, $\beta_A$ and $\beta_B$ chains. λNIHα-2 was identified as containing coding regions for the human α inhibin chain. The prevalence of hybridizing clones in the case of human α inhibin was considerably less than that found for porcine α inhibin, on the order of 1 in 100,000 human clones hybridized to the 685 bp SmaI fragment of the porcine cDNA for αInh. The β chain clones were also rare, with the $\beta_B$ clones being present at about 3 times the level of $\beta_A$ (1 and 3 out of about 1,000,000 clones, respectively). None of the β chain clones were full length. They were supplemented with a primed cDNA library and assembled generally as described above for the porcine cDNA. The λ inserts were recovered by EcoRl digestion.

Plasmid pHINα-2 is digested with NcoI and SmaI, and the 1049 bp 15 fragment (fragment 10) is recovered by gel electrophoresis. pPinα (Example 2) is digested with EcoRI and PvuII. The 98 bp fragment (fragment 11) is recovered by gel electrophoresis. Fragments 10 and 11 are ligated to adaptor I 5'-CTGCTCCTCTTGCTGTTGGCCCCACG-GAGTGGGCATGGCTGCCAGGGCCCG-GAGCTGGACC-3' (SEQ ID NO. 26), in combination with adaptor II which is the complement of adaptor I. The resulting 1208 bp fragment (fragment 12) is treated with Klenow fragment of Pol(I) and the 4 dNTP's and ligated to pHBS348-EsaII which has been restricted with HindIII and SacII and blunt-ended as described in Example 1. Alternatively, pPinα was digested with EcoRI and HpaII, with the fragment encoding upstream from the HpaII site (that is, the first 21 residues of the porcine sequence) being recovered. The adaptor used in this alternative approach was

5'-CGGAGCTCGACC-3'     (SEQ ID NO. 27)

3'-CTCGAGCTGG-5'.      (SEQ ID NO. 28)

A plasmid pSVE-HαInh having the correct orientation of fragment 12 is identified by sequence analysis of transformants. This construction (pSVE-HαInh) thus contains the first 24 residues of the porcine signal sequence with the remainder being prepro human inhibin. Plasmid pSVE-HαInh is digested with SalI. The fragment containing the SV40 promoter and human inhibin sequence is ligated to fragment 9 and SalI digested pSVE-$\beta_A$Inh (Example 2). This final plasmid designated pSVE-hα$\beta_A$Inh-DHFR1 is transfected into DHFR-deficient CHO cells and selected as described in Example 2. The culture supernatant contains hormonally active human inhibin.

EXAMPLE 4

Construction of Human Inhibin Vector and Expression of Human Inhibin in Recombinant Cell Culture-II This example is similar to Example 3 except that the pro sequence of human inhibin $\beta_B$ was employed in the place of the porcine $\beta_B$ prepro domain.

The lambda gt10 library of Example 3 yielded λHINα2, as described in example 3, together with λHIN$\beta_A$-5 and -14. the latter two phage were employed to construct the full length $\beta_A$ coding cDNA by ligating the 311 bp EcoRI-HindIII fragment (fragment 13) of λHIN$\beta_A$-5 to the 1101 bp HindIII-HpaI fragment (fragment 14) of λHIN$\beta_A$-14 and ligating this mixture in an EcoRl-SmaI digested mp18 vector (Biolabs). Clones were selected and screened for the appropriate sized insert. An mp18 vector containing the correct insert was treated with DNA polymerase(I) and the four dNTPs in order to render it double stranded, and thereafter digested with XbaI (which cleaves in the mp18 polylinker sequence), blunted with DNA polymerase I and the four dNTPs, and digested with EcoRl. A 1320 bp fragment (fragment 15) was ligated to the EcoRl-EcoRV fragment 1 from Example 2. This ligation mixture was used to transform E. coli 294 cells. Clones were screened by Southern Hybridization and confirmed by restriction analysis. The clone containing the hInh$\beta_A$ coding sequence was designated pSVE-hum$\beta_A$Inh. A plasmid containing the human $\beta_A$ coding sequences and the human $\alpha$-inhibin sequences together with the DHFR gene is constructed from plasmids pSVE-hum$\beta_A$Inh, pSVE-H$\alpha$Inh and pFDIISalI as outlined above. Specifically, the Sal fragments from pSVE-H$\alpha$Inh and pFDIISalI which contain the human alpha inhibin and the DHFR genes were ligated with SalI digested pSVE-hum$\beta_A$Inh and a clone containing all three genes was identified. This plasmid, designated pSVE-hum$\alpha\beta_A$Inh-DHFR2, was transfected into DHFR$^-$ CHO cells and selected by culture in ght$^-$ medium. 24 clones were picked, grown to confluency in ght$^-$ medium under conditions conventional for CHO cells for two days, allowed to rest for 2 more days and thereafter the culture media were assayed for inhibin and activin activity using the rat pituitary cell assay described above. 4 clones were found to secrete significant levels of human $\alpha\beta_A$ inhibin (h$\alpha\beta_A$-8, 12, 14, and 18). The levels in the culture medium for each clone were, respectively, 125, 125, 200 and 250 ng/ml. Another clone (h$\alpha\beta_A$-11) produced activin as the $\beta_{A\beta A}$ homodimer, but no detectable inhibin, as determined by biological activity and the lack of $\alpha$ chain immunoreactivity in the culture medium for this clone. Clone h$\alpha\beta_A$-16 secreted only $\alpha$ chain and was devoid of activin or inhibin activity.

EXAMPLE 5

Recombinant Expression of Human Activin

As reported by Vale et al. (Id.) and Ling et al. (Id.), homodimers and heterodimers of the $\beta$ chains A and/or B have the opposite effect of inhibin on the pituitary, inducing rather than inhibiting FSH secretion. These proteins, collectively termed activin, are made in $\alpha$ and $\beta$ chain cotransformants as described in Example 4. However, somewhat less screening for an appropriate transformant is needed if the initial transfection is conducted with a vector or vectors that do not contain the $\alpha$ chain gene. A suitable vector is readily constructed from the above-described vectors by excising the $\alpha$ chain gene. Plasmid pSVE-hum$\beta_A$Inh from Example 4 is digested with SalI and ligated to fragment 9 (Example 2) containing the DHFR gene. The ligation mixture was used to transfect E. coli 294 cells and colonies selected on the basis of failure to hybridize to the $\alpha$ chain sequence but which did hybridize to the $\beta$ chain DNA. A clone pSVE-hum$\beta_A$Inh-DHFR was identified from which the $\alpha$ chain DNA had been deleted. This clone is transfected into DHFR$^-$ CHO cells as described above. Transformants are identified that secrete activin into the culture medium. Similarly, an expression vector containing a $\beta_B$ coding sequence (reconstituted by ligating DNA encoding the first 34 amino acids of human $\beta_A$ to the remaining coding sequence of the human $\beta_B$ chain) is readily constructed and cotransfected with pSVE-hum$\beta_A$Inh-DHFR to produce the heterodimer. The reconstructed human $\beta_B$ gene also is used in the foregoing plasmids in order to produce $\alpha\beta_B$-inhibin which, in the in vitro bioassay, has essentially equivalent biological potency to the $\alpha\beta_A$ form of inhibin.

Although the invention has been described with regard to its preferred embodiments, which constitute the best mode presently known to the inventors, it should be understood that various changes and modifications as would be obvious to one having the ordinary skill in the art may be made without departing from the scope of the invention which is set forth in the claims appended hereto.

We claim:

1. Non-chromosomal DNA encoding an inhibin α chain polypeptide selected from the group consisting of the porcine inhibin α chain having the sequence shown as residues 231–364 of SEQ ID NO: 29, a variant inhibin α chain having a sequence identical to residues 231–364 of SEQ ID NO: 29 except for the replacement of Asn$^{266}$ by Gln, the human inhibin α chain having the sequence shown as residues 218–351 of SEQ ID NO: 39, a variant inhibin α chain having a sequence identical to residues 218–351 of SEQ ID NO: 39 except for the replacement of Asn$^{237}$ by Gln, and a mature mammalian inhibin α chain polypeptide,
wherein DNA encoding said mammalian polypeptide has the sequence of DNA which is specifically identified on a Southern blot of an ovarian cDNA library using any 64-nucleotide probe within residues 762–1166 of SEQ ID NO: 30 or within residues 654–1058 of SEQ ID NO: 40,
and wherein said mammalian inhibin α chain polypeptide is capable, not by itself but when combined with a mature mammalian inhibin β chain polypeptide, of inhibiting the basal release of follicle stimulating hormone, but not of luteinizing hormone, from anterior pituitary cells.

2. The DNA of claim 1 that is free of intervening untranslated sequences.

3. The DNA of claim 1 wherein the polypeptide has an amino acid sequence shown as residues 231–364 of SEQ ID NO: 29 or shown as residues 218–351 of SEQ ID NO: 39.

4. The DNA of claim 1 that is labeled with a detectable moiety.

5. A replicable vector comprising DNA encoding an inhibin α chain polypeptide selected from the group consisting of the porcine inhibin α chain having the sequence shown as residues 231–364 of SEQ ID NO: 29, a variant inhibin α chain having a sequence identical to residues 231–364 of SEQ ID NO: 29 except for the replacement of Asn$^{266}$ by Gln, the human inhibin α chain having the sequence shown as residues 218–351 of SEQ ID NO: 39, a variant inhibin α chain having a sequence identical to residues 218–351 of SEQ ID NO: 39 except for the replacement of Asn$^{237}$ by Gln, and a mature mammalian inhibin α chain polypeptide,
wherein DNA encoding said mammalian polypeptide has the sequence of DNA which is specifically identified on a Southern blot of an ovarian cDNA library using any 65-nucleotide probe within residues 762–1166 of SEQ ID NO: 30 or within residues 654–1058 of SEQ ID NO: 40,
and wherein said mammalian inhibin α chain polypeptide is capable, not by itself but when combined with a mature mammalian inhibin β chain polypeptide, of inhibiting the basal release of follicle stimulating hormone, but not of luteinizing hormone, from anterior pituitary cells.

6. The vector of claim 5 wherein the polypeptide has an amino acid sequence shown as residues 231–364 of SEQ ID NO: 29 or shown as residues 218–351 of SEQ ID NO: 39.

7. The vector of claim 6 comprising a viral promoter operably linked to the DNA encoding the polypeptide.

8. A host cell transformed with a replicable vector comprising DNA encoding an inhibin α chain polypeptide selected from the group consisting of the porcine inhibin α chain having the sequence shown as residues 231–364 of SEQ ID NO: 29, a variant inhibin α chain having a sequence identical to residues 231–364 of SEQ ID NO: 29 except for the replacement of Asn$^{266}$ by Gln, the human inhibin α chain having the sequence shown as residues 218–351 of SEQ ID NO: 39, a variant inhibin α chain having a sequence identical to residues 218–351 of SEQ ID NO: 39 except for the replacement of Asn$^{237}$ by Gln, and a mature mammalian inhibin α chain polypeptide,
wherein DNA encoding said mammalian polypeptide has the sequence of DNA which is specifically identified on a Southern blot of an ovarian cDNA library using any 64-nucleotide probe within residues 762–1166 of SEQ ID NO: 30 or within residues 654–1058 of SEQ ID NO: 40, and wherein said mammalian inhibin α chain polypeptide is capable, not by itself but when combined with a mature mammalian inhibin β chain polypeptide, of inhibiting the basal release of follicle stimulating hormone, but not of luteinizing hormone, from anterior pituitary cells.

9. The cell of claim 8 that is a eukaryotic cell.

10. The cell of claim 8 wherein the polypeptide has an amino acid sequence shown as residues 231–364 of SEQ ID NO: 29 or shown as residues 218–351 of SEQ ID NO: 39.

11. A method for expressing a mature inhibin α chain polypeptide, comprising the steps of (a) constructing a vector that comprises a nucleic acid selected from the group consisting of DNA encoding the porcine inhibin α chain having the sequence shown as residues 231–364 of SEQ ID NO: 29, DNA encoding a variant inhibin α chain having a sequence identical to residues 231–364 of SEQ ID NO: 29 except for the replacement of Asn$^{266}$ by Gln, DNA encoding the human inhibin α chain having the sequence shown as residues 218–351 of SEQ ID NO: 39, DNA encoding a variant inhibin α chain having a sequence identical to residues 218–351 of SEQ ID NO: 39 except for the replacement of Asn$^{237}$ by Gln, and DNA encoding a mature mammalian inhibin α chain polypeptide,
wherein DNA encoding said mammalian polypeptide has the sequence of DNA which is specifically identified on a Southern blot of an ovarian cDNA library using any 64-nucleotide probe within residues 762–1166 of SEQ ID NO: 30 or within residues 654–1058 of SEQ ID NO: 40, and wherein said mammalian inhibin α chain polypeptide is capable, not by itself but when combined with a mature mammalian inhibin β chain polypeptide, of inhibiting the basal release of follicle stimulating hormone, but not of luteinizing hormone, from anterior pituitary cells;

(b) transforming a host cell with the vector; and (c) culturing the transformed cell under conditions appropriate for the expression of said polypeptide.

12. The method of claim 11 wherein the nucleic acid is operably linked to a promoter recognized by the host cell and comprising further the step of recovering the polypeptide from the culture medium.

13. The method of claim 12 wherein the promoter is a viral promoter.

14. The method of claim 13 wherein the promoter is an SV40 promoter.

15. The method of claim 11 wherein the cell is of mammalian origin.

16. The method of claim 11 wherein the cell is a prokaryote.

17. The method of claim 16 wherein the polypeptide has an amino acid sequence shown as residues 231–364 of SEQ ID NO: 29 or shown as residues 218–351 of SEQ ID NO: 39.

* * * * *

UNITED STATES PATENT AND TRADEMARK OFFICE
CERTIFICATE OF CORRECTION

PATENT NO. : 5,525,488
DATED : June 11, 1996
INVENTOR(S) : Anthony J. Mason; Peter H. Seeburg It is certified that error appears in the above-indentified patent and that said Letters Patent is hereby corrected as shown below:

In column 72, claim 5, line 43, replace "65-nucleotide" with -- 64-nucleotide --

Signed and Sealed this

Third Day of September, 1996

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 44

( 2 ) INFORMATION FOR SEQ ID NO:1:

( i ) SEQUENCE CHARACTERISTICS:
        ( A ) LENGTH: 26 amino acids
        ( B ) TYPE: amino acid
        ( D ) TOPOLOGY: linear ( x i ) SEQUENCE DESCRIPTION: SEQ ID NO:1:

```
Ser  Thr  Ala  Pro  Leu  Pro  Trp  Pro  Trp  Ser  Pro  Ala  Ala  Leu  Arg
 1                  5                        10                       15

Leu  Leu  Gln  Arg  Pro  Pro  Glu  Glu  Pro  Ala  Val
                    20                       25   26
```

( 2 ) INFORMATION FOR SEQ ID NO:2:

(i) SEQUENCE CHARACTERISTICS:
  (A) LENGTH: 31 amino acids
  (B) TYPE: amino acid
  (D) TOPOLOGY: linear (xi) SEQUENCE DESCRIPTION: SEQ ID NO:2:

```
Gly Leu Glu Xaa Asp Gly Lys Val Asn Ile Xaa Xaa Lys Lys Gln
 1               5                  10                  15

Phe Phe Val Ser Phe Lys Asp Ile Gly Trp Asn Asp Trp Ile Ile
                20                  25                  30

Ala
31
```

(2) INFORMATION FOR SEQ ID NO:3:

(i) SEQUENCE CHARACTERISTICS:
    (A) LENGTH: 22 amino acids
    (B) TYPE: amino acid
    (D) TOPOLOGY: linear (xi) SEQUENCE DESCRIPTION: SEQ ID NO:3:

```
Gly Leu Glu Xaa Asp Gly Arg Thr Asn Leu Xaa Xaa Arg Gln Gln
 1               5                  10                  15

Phe Phe Ile Asp Phe Arg Leu
                20      22
```

(2) INFORMATION FOR SEQ ID NO:4:

(i) SEQUENCE CHARACTERISTICS:
    (A) LENGTH: 5 amino acids
    (B) TYPE: amino acid
    (D) TOPOLOGY: linear (xi) SEQUENCE DESCRIPTION: SEQ ID NO:4:

```
Arg Arg Arg Arg Arg
 1               5
```

(2) INFORMATION FOR SEQ ID NO:5:

(i) SEQUENCE CHARACTERISTICS:
    (A) LENGTH: 31 amino acids
    (B) TYPE: amino acid
    (D) TOPOLOGY: linear (xi) SEQUENCE DESCRIPTION: SEQ ID NO:5:

```
Gly His Ser Ala Ala Pro Asp Cys Pro Ser Cys Ala Leu Ala Thr
 1               5                  10                  15

Leu Pro Lys Asp Val Pro Asn Ser Gln Pro Glu Met Val Glu Ala
                20                  25                  30

Val
31
```

(2) INFORMATION FOR SEQ ID NO:6:

(i) SEQUENCE CHARACTERISTICS:
    (A) LENGTH: 27 amino acids
    (B) TYPE: amino acid
    (D) TOPOLOGY: linear (xi) SEQUENCE DESCRIPTION: SEQ ID NO:6:

```
His Ile Leu Asn Met Leu His Leu Lys Lys Arg Pro Asp Val Thr
 1               5                  10                  15

Gln Pro Val Pro Lys Ala Ala Leu Leu Asn Ala Ile
                20                  25      27
```

( 2 ) INFORMATION FOR SEQ ID NO:7:

( i ) SEQUENCE CHARACTERISTICS:
        ( A ) LENGTH: 19 amino acids
        ( B ) TYPE: amino acid
        ( D ) TOPOLOGY: linear ( x i ) SEQUENCE DESCRIPTION: SEQ ID NO:7:

```
Leu His Val Gly Lys Val Gly Glu Asn Gly Tyr Val Glu Leu Glu
 1               5                  10                   15

Asp Asp Ile Gly
            19
```

( 2 ) INFORMATION FOR SEQ ID NO:8:

( i ) SEQUENCE CHARACTERISTICS:
        ( A ) LENGTH: 68 amino acids
        ( B ) TYPE: amino acid
        ( D ) TOPOLOGY: linear ( x i ) SEQUENCE DESCRIPTION: SEQ ID NO:8:

```
Ala Glu Met Asn Glu Leu Met Glu Gln Thr Ser Glu Ile Ile Thr
 1               5                  10                   15

Phe Ala Glu Ala Gly Arg Ala Arg Lys Thr Leu Arg Phe Glu Ile
                20                  25                   30

Ser Lys Glu Gly Ser Asp Leu Ser Val Val Glu Arg Ala Glu Ile
                35                  40                   45

Trp Leu Phe Lys Val Pro Lys Ala Asn Arg Thr Arg Thr Lys Val
                50                  55                   60

Ser Ile Arg Leu Phe Gln Gln Gln
                65          68
```

( 2 ) INFORMATION FOR SEQ ID NO:9:

( i ) SEQUENCE CHARACTERISTICS:
        ( A ) LENGTH: 32 amino acids
        ( B ) TYPE: amino acid
        ( D ) TOPOLOGY: linear ( x i ) SEQUENCE DESCRIPTION: SEQ ID NO:9:

```
Pro Gln Gly Ser Ala Asp Ala Gly Glu Glu Ala Glu Asp Val Gly
 1               5                  10                   15

Phe Pro Glu Glu Lys Ser Glu Val Leu Ile Ser Glu Lys Val Val
                20                  25                   30

Asp Ala
    32
```

( 2 ) INFORMATION FOR SEQ ID NO:10:

( i ) SEQUENCE CHARACTERISTICS:
        ( A ) LENGTH: 43 amino acids
        ( B ) TYPE: amino acid
        ( D ) TOPOLOGY: linear ( x i ) SEQUENCE DESCRIPTION: SEQ ID NO:10:

```
Ser Thr Trp His Ile Phe Pro Val Ser Ser Ile Gln Arg Leu
 1               5                  10                   15

Leu Asp Gln Gly Lys Ser Ala Leu Asp Ile Arg Thr Ala Cys Glu
                20                  25                   30

Gln Cys His Glu Thr Gly Ala Ser Leu Val Leu Leu Gly
                35                  40          43
```

( 2 ) INFORMATION FOR SEQ ID NO:11:

( i ) SEQUENCE CHARACTERISTICS:
        ( A ) LENGTH: 60 amino acids
        ( B ) TYPE: amino acid
        ( D ) TOPOLOGY: linear ( x i ) SEQUENCE DESCRIPTION: SEQ ID NO:11:

```
Gly His Ser Ala Ala Pro Asp Cys Pro Ser Cys Ala Leu Ala Thr
 1               5                  10                  15

Leu Pro Lys Asp Val Pro Asn Ser Gln Pro Glu Met Val Glu Ala
                20                  25                  30

Val Lys Lys His Ile Leu Asn Met Leu His Leu Lys Lys Arg Pro
                35                  40                  45

Asp Val Thr Gln Pro Val Pro Lys Ala Ala Leu Leu Asn Ala Ile
                50                  55                  60
```

( 2 ) INFORMATION FOR SEQ ID NO:12:

( i ) SEQUENCE CHARACTERISTICS:
        ( A ) LENGTH: 18 amino acids
        ( B ) TYPE: amino acid
        ( D ) TOPOLOGY: linear ( x i ) SEQUENCE DESCRIPTION: SEQ ID NO:12:

```
Arg Ala Ala His Ile Leu Leu His Ala Val Arg Val Ser Gly Trp
 1               5                  10                  15

Leu Asn Leu
           18
```

( 2 ) INFORMATION FOR SEQ ID NO:13:

( i ) SEQUENCE CHARACTERISTICS:
        ( A ) LENGTH: 35 amino acids
        ( B ) TYPE: amino acid
        ( D ) TOPOLOGY: linear ( x i ) SEQUENCE DESCRIPTION: SEQ ID NO:13:

```
Gly Pro Glu Leu Asp Arg Glu Leu Val Leu Ala Lys Val Arg Ala
 1               5                  10                  15

Leu Phe Leu Asp Ala Leu Gly Pro Pro Ala Val Thr Gly Glu Gly
                20                  25                  30

Gly Asp Pro Gly Val
                35
```

( 2 ) INFORMATION FOR SEQ ID NO:14:

( i ) SEQUENCE CHARACTERISTICS:
        ( A ) LENGTH: 159 amino acids
        ( B ) TYPE: amino acid
        ( D ) TOPOLOGY: linear ( x i ) SEQUENCE DESCRIPTION: SEQ ID NO:14:

```
Gly Ser Glu Pro Glu Glu Asp Val Ser Gln Ala Ile Leu Phe
 1               5                  10                  15

Pro Ala Thr Gly Ala Arg Cys Gly Ala Glu Pro Ala Ala Gly Glu
                20                  25                  30

Leu Ala Arg Glu Ala Glu Glu Gly Leu Phe Thr Tyr Val Gly Arg
                35                  40                  45

Pro Ser Gln His Thr His Ser Arg Gln Val Thr Ser Ala Gln Leu
                50                  55                  60

Trp Phe His Thr Gly Leu Asp Arg Gln Gly Met Ala Ala Ala Asn
```

|     |     |     |     |     | 65  |     |     |     |     | 70  |     |     |     |     | 75  |
|-----|-----|-----|-----|-----|-----|-----|-----|-----|-----|-----|-----|-----|-----|-----|-----|

Ser Ser Gly Pro Leu Leu Asp Leu Leu Ala Leu Ser Ser Arg Gly
                80                      85                      90

Pro Val Ala Val Pro Met Ser Leu Gly Gln Ala Pro Pro Arg Trp
                95                      100                     105

Ala Val Leu His Leu Ala Ala Ser Ala Leu Pro Leu Leu Thr His
                110                     115                     120

Pro Val Leu Val Leu Leu Leu Arg Cys Pro Leu Cys Ser Cys Ser
                125                     130                     135

Ala Arg Pro Glu Ala Thr Pro Phe Leu Val Ala His Thr Arg Ala
                140                     145                     150

Arg Pro Pro Ser Gly Gly Glu Arg Ala
                155             159

(2) INFORMATION FOR SEQ ID NO:15:

(i) SEQUENCE CHARACTERISTICS:
        (A) LENGTH: 16 bases
        (B) TYPE: nucleic acid
        (C) STRANDEDNESS: single
        (D) TOPOLOGY: linear (xi) SEQUENCE DESCRIPTION: SEQ ID NO:15:

AATTCACTCG AGACGC                                                                16

(2) INFORMATION FOR SEQ ID NO:16:

(i) SEQUENCE CHARACTERISTICS:
        (A) LENGTH: 12 bases
        (B) TYPE: nucleic acid
        (C) STRANDEDNESS: single
        (D) TOPOLOGY: linear (xi) SEQUENCE DESCRIPTION: SEQ ID NO:16:

GTGAGCTCTG CG                                                                    12

(2) INFORMATION FOR SEQ ID NO:17:

(i) SEQUENCE CHARACTERISTICS:
        (A) LENGTH: 64 bases
        (B) TYPE: nucleic acid
        (C) STRANDEDNESS: single
        (D) TOPOLOGY: linear (xi) SEQUENCE DESCRIPTION: SEQ ID NO:17:

ACCGCCCCTT TGCCTTGGCC TTGGTCCCCT GCTGCTCTGA GACTGCTGCA           50

GAGACCTCCT GAGG                                                                  64

(2) INFORMATION FOR SEQ ID NO:18:

(i) SEQUENCE CHARACTERISTICS:
        (A) LENGTH: 16 bases
        (B) TYPE: nucleic acid
        (C) STRANDEDNESS: single
        (D) TOPOLOGY: linear (xi) SEQUENCE DESCRIPTION: SEQ ID NO:18:

CCCCACAGCA TGTCTT                                                                16

(2) INFORMATION FOR SEQ ID NO:19:

(i) SEQUENCE CHARACTERISTICS:
        (A) LENGTH: 56 bases
        (B) TYPE: nucleic acid ( C ) STRANDEDNESS: single
( D ) TOPOLOGY: linear ( x i ) SEQUENCE DESCRIPTION: SEQ ID NO:19:

AAGAAGCAGT TCTTTGTGTC CTTCAAGGAC ATTGGCTGGA ATGACTGGAT 50

CATTGC 56

( 2 ) INFORMATION FOR SEQ ID NO:20:

( i ) SEQUENCE CHARACTERISTICS:
        ( A ) LENGTH: 65 bases
        ( B ) TYPE: nucleic acid
        ( C ) STRANDEDNESS: single
        ( D ) TOPOLOGY: linear ( x i ) SEQUENCE DESCRIPTION: SEQ ID NO:20:

GGCCTGGAGT GTGATGGGAG AACCAACCTG TCCTGCCGCC AGGAATTTTT 50

CATCGATTTC AGGCT 65

( 2 ) INFORMATION FOR SEQ ID NO:21:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( x i ) SEQUENCE DESCRIPTION: SEQ ID NO:21:

AANTCTATNA ANAATTGT 18

( 2 ) INFORMATION FOR SEQ ID NO:22:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( x i ) SEQUENCE DESCRIPTION: SEQ ID NO:22:

AANTCTATNA ANAATTGC 18

( 2 ) INFORMATION FOR SEQ ID NO:23:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( x i ) SEQUENCE DESCRIPTION: SEQ ID NO:23:

AANTCTATNA ANAACTGT 18

( 2 ) INFORMATION FOR SEQ ID NO:24:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( x i ) SEQUENCE DESCRIPTION: SEQ ID NO:24:

AANTCTATNA ANAACTGC 18

( 2 ) INFORMATION FOR SEQ ID NO:25:

( i ) SEQUENCE CHARACTERISTICS:

(A) LENGTH: 7 amino acids
(B) TYPE: amino acid
(D) TOPOLOGY: linear (xi) SEQUENCE DESCRIPTION: SEQ ID NO:25:

| Gln | Gln | Phe | Phe | Ile | Asp | Phe |
|---|---|---|---|---|---|---|
| 1 | | | | 5 | | 7 |

(2) INFORMATION FOR SEQ ID NO:26:

(i) SEQUENCE CHARACTERISTICS:
        (A) LENGTH: 61 bases
        (B) TYPE: nucleic acid
        (C) STRANDEDNESS: single
        (D) TOPOLOGY: linear (xi) SEQUENCE DESCRIPTION: SEQ ID NO:26:

CTGCTCCTCT TGCTGTTGGC CCCACGGAGT GGGCATGGCT GCCAGGGCCC  50

GGAGCTGGAC C  61

(2) INFORMATION FOR SEQ ID NO:27:

(i) SEQUENCE CHARACTERISTICS:
        (A) LENGTH: 12 bases
        (B) TYPE: nucleic acid
        (C) STRANDEDNESS: single
        (D) TOPOLOGY: linear (xi) SEQUENCE DESCRIPTION: SEQ ID NO:27:

CGGAGCTCGA CC  12

(2) INFORMATION FOR SEQ ID NO:28:

(i) SEQUENCE CHARACTERISTICS:
        (A) LENGTH: 10 bases
        (B) TYPE: nucleic acid
        (C) STRANDEDNESS: single
        (D) TOPOLOGY: linear (xi) SEQUENCE DESCRIPTION: SEQ ID NO:28:

CTCGAGCTGG  10

(2) INFORMATION FOR SEQ ID NO:29:

(i) SEQUENCE CHARACTERISTICS:
        (A) LENGTH: 364 amino acids
        (B) TYPE: amino acid
        (D) TOPOLOGY: linear (xi) SEQUENCE DESCRIPTION: SEQ ID NO:29:

| Met | Trp | Pro | Gln | Leu | Leu | Leu | Leu | Leu | Leu | Ala | Pro | Arg | Ser | Gly |
|---|---|---|---|---|---|---|---|---|---|---|---|---|---|---|
| 1 | | | | 5 | | | | | 10 | | | | | 15 |
| His | Gly | Cys | Gln | Gly | Pro | Glu | Leu | Asp | Arg | Glu | Leu | Val | Leu | Ala |
| | | | | 20 | | | | | 25 | | | | | 30 |
| Lys | Val | Arg | Ala | Leu | Phe | Leu | Asp | Ala | Leu | Gly | Pro | Pro | Ala | Val |
| | | | | 35 | | | | | 40 | | | | | 45 |
| Thr | Gly | Glu | Gly | Gly | Asp | Pro | Gly | Val | Arg | Arg | Leu | Pro | Arg | Arg |
| | | | | 50 | | | | | 55 | | | | | 60 |
| His | Ala | Val | Gly | Gly | Phe | Met | Arg | Arg | Gly | Ser | Glu | Pro | Glu | Glu |
| | | | | 65 | | | | | 70 | | | | | 75 |
| Glu | Asp | Val | Ser | Gln | Ala | Ile | Leu | Phe | Pro | Ala | Thr | Gly | Ala | Arg |
| | | | | 80 | | | | | 85 | | | | | 90 |
| Cys | Gly | Asp | Glu | Pro | Ala | Ala | Gly | Glu | Leu | Ala | Arg | Glu | Ala | Glu |
| | | | | 95 | | | | | 100 | | | | | 105 |

| | | | | | | | | | | | | | | |
|---|---|---|---|---|---|---|---|---|---|---|---|---|---|---|
| Glu | Gly | Leu | Phe | Thr<br>110 | Tyr | Val | Phe | Arg | Pro<br>115 | Ser | Gln | His | Thr | His<br>120 |
| Ser | Arg | Gln | Val | Thr<br>125 | Ser | Ala | Gln | Leu | Trp<br>130 | Phe | His | Thr | Gly | Leu<br>135 |
| Asp | Arg | Gln | Gly | Met<br>140 | Ala | Ala | Ala | Asn | Ser<br>145 | Ser | Gly | Pro | Leu | Leu<br>150 |
| Asp | Leu | Leu | Ala | Leu<br>155 | Ser | Ser | Arg | Gly | Pro<br>160 | Val | Ala | Val | Pro | Met<br>165 |
| Ser | Leu | Gly | Gln | Ala<br>170 | Pro | Pro | Arg | Trp | Ala<br>175 | Val | Leu | His | Leu | Ala<br>180 |
| Ala | Ser | Ala | Leu | Pro<br>185 | Leu | Leu | Thr | His | Pro<br>190 | Val | Leu | Val | Leu | Leu<br>195 |
| Leu | Arg | Cys | Pro | Leu<br>200 | Cys | Ser | Cys | Ser | Ala<br>205 | Arg | Pro | Glu | Ala | Thr<br>210 |
| Pro | Phe | Leu | Val | Ala<br>215 | His | Thr | Arg | Ala | Arg<br>220 | Pro | Pro | Ser | Gly | Gly<br>225 |
| Glu | Arg | Ala | Arg | Arg<br>230 | Ser | Thr | Ala | Pro | Leu<br>235 | Pro | Trp | Pro | Trp | Ser<br>240 |
| Pro | Ala | Ala | Leu | Arg<br>245 | Leu | Leu | Gln | Arg | Pro<br>250 | Pro | Glu | Glu | Pro | Ala<br>255 |
| Val | His | Ala | Asp | Cys<br>260 | His | Arg | Ala | Ser | Leu<br>265 | Asn | Ile | Ser | Phe | Gln<br>270 |
| Glu | Leu | Gly | Trp | Asp<br>275 | Arg | Trp | Ile | Val | His<br>280 | Pro | Pro | Ser | Phe | Ile<br>285 |
| Phe | His | Tyr | Cys | His<br>290 | Gly | Gly | Cys | Gly | Leu<br>295 | Pro | Thr | Leu | Pro | Asn<br>300 |
| Leu | Pro | Leu | Ser | Val<br>305 | Pro | Gly | Ala | Pro | Pro<br>310 | Thr | Pro | Val | Gln | Pro<br>315 |
| Leu | Leu | Leu | Val | Pro<br>320 | Gly | Ala | Gln | Pro | Cys<br>325 | Cys | Ala | Ala | Leu | Pro<br>330 |
| Gly | Thr | Met | Arg | Ser<br>335 | Leu | Arg | Val | Arg | Thr<br>340 | Thr | Ser | Asp | Gly | Gly<br>345 |
| Tyr | Ser | Phe | Lys | Tyr<br>350 | Glu | Thr | Val | Pro | Asn<br>355 | Leu | Leu | Thr | Gln | His<br>360 |
| Cys | Ala | Cys | Ile<br>364 | | | | | | | | | | | |

( 2 ) INFORMATION FOR SEQ ID NO:30:

( i ) SEQUENCE CHARACTERISTICS:
        ( A ) LENGTH: 1343 bases
        ( B ) TYPE: nucleic acid
        ( C ) STRANDEDNESS: single
        ( D ) TOPOLOGY: linear ( x i ) SEQUENCE DESCRIPTION: SEQ ID NO:30:

```
TGTGGGGCAG  ACCCTGACAG  AAGGGGCACA  GGGCTGGGTG  TGGGTTCACC   50
GTTGGCAGGG  CCAGGTGAGC  TATGTGGCCT  CAGCTGCTCC  TCTTGCTGTT  100
GGCCCCACGG  AGTGGGCATG  GCTGCCAGGG  CCCGGAGCTG  ACCGGGAGC   150
TTGTCCTGGC  CAAGGTGAGG  GCTCTGTTCC  TGGATGCCTT  GGGACCCCCG  200
GCAGTGACTG  GGGAAGGTGG  GGATCCTGGA  GTCAGGCGTC  TGCCCCGAAG  250
ACATGCTGTG  GGGGGCTTCA  TGCGCAGGGG  CTCTGAGCCC  GAGGAGGAGG  300
ATGTCTCCCA  GGCCATCCTT  TTCCCGGCTA  CAGGTGCCCG  CTGTGGGGAC  350
```

| | | | | |
|---|---|---|---|---|
| GAGCCAGCTG | CTGGAGAGCT | GGCCCGGGAG | GCTGAGGAGG | GCCTCTTCAC 400 |
| ATATGTATTC | CGGCCGTCCC | AGCACACACA | CAGCCGCCAG | GTGACTTCAG 450 |
| CTCAGCTGTG | GTTCCACACG | GGACTGGACA | GACAGGGGAT | GGCAGCCGCC 500 |
| AATAGCTCTG | GGCCCCTGCT | GGACCTGCTG | GCACTATCAT | CCAGGGGTCC 550 |
| TGTGGCTGTG | CCCATGTCAC | TGGGCCAGGC | GCCCCCTCGC | TGGGCTGTGC 600 |
| TGCACCTGGC | CGCCTCTGCC | CTCCCTTTGT | TGACCCACCC | AGTCCTGGTG 650 |
| CTGCTGCTGC | GCTGTCCTCT | CTGTTCCTGC | TCAGCCCGGC | CCGAGGCCAC 700 |
| CCCCTTCCTG | GTGGCCCACA | CTCGGGCCAG | GCCACCCAGC | GGAGGGGAGA 750 |
| GGGCCCGACG | CTCCACCGCC | CCTCTGCCCT | GGCCTTGGTC | CCCCGCCGCG 800 |
| CTGCGCCTGC | TGCAGAGGCC | CCCGGAGGAA | CCCGCTGTGC | ACGCCGACTG 850 |
| CCACAGAGCT | TCCCTCAACA | TCTCCTTCCA | GGAGCTGGGC | TGGGACCGGT 900 |
| GGATCGTGCA | CCCTCCCAGT | TTCATCTTCC | ACTACTGTCA | CGGGGGCTGC 950 |
| GGGCTGCCGA | CCCTGCCCAA | CCTGCCCCTG | TCTGTCCCTG | GGCCCCCCC 1000 |
| TACCCCTGTC | CAGCCCCTGT | TGTTGGTGCC | AGGGGCTCAG | CCCTGCTGCG 1050 |
| CTGCTCTCCC | GGGGACCATG | AGGTCCCTAC | GCGTTCGCAC | CACCTCGGAT 1100 |
| GGAGGTTACT | CTTTCAAGTA | CGAGACGGTG | CCCAACCTTC | TCACCCAGCA 1150 |
| CTGTGCCTGC | ATCTAAGGGT | GTCCCGCTGG | TGGCCGAGCT | CCCACAGGCA 1200 |
| CCAGCCTGGA | GGAAGGCAGA | GTTCCCACCT | CCCCTTTCCT | TCCGCCTCTC 1250 |
| CGCCTGGAGG | CTCCCCTCCC | TGTCCGCCCC | TGTCCCATGG | GTAATGTGAC 1300 |
| AATAAACAGC | ATAGTGCAGA | TGACTCGGTG | CGCAAAAAAA | AAA 1343 |

( 2 ) INFORMATION FOR SEQ ID NO:31:

( i ) SEQUENCE CHARACTERISTICS:
( A ) LENGTH: 424 amino acids
( B ) TYPE: amino acid
( D ) TOPOLOGY: linear ( x i ) SEQUENCE DESCRIPTION: SEQ ID NO:31:

| | | | | | | | | | | | | | | |
|---|---|---|---|---|---|---|---|---|---|---|---|---|---|---|
| Met 1 | Pro | Leu | Leu | Trp 5 | Leu | Arg | Gly | Phe | Leu 10 | Leu | Ala | Ser | Cys | Trp 15 |
| Ile | Ile | Val | Arg | Ser 20 | Ser | Pro | Thr | Pro | Gly 25 | Ser | Gly | Gly | His | Ser 30 |
| Ala | Ala | Pro | Asp | Cys 35 | Pro | Ser | Cys | Ala | Leu 40 | Ala | Thr | Leu | Pro | Lys 45 |
| Asp | Val | Pro | Asn | Ser 50 | Gln | Pro | Glu | Met | Val 55 | Glu | Ala | Val | Lys | Lys 60 |
| His | Ile | Leu | Asn | Met 65 | Leu | His | Leu | Lys | Lys 70 | Arg | Pro | Asp | Val | Thr 75 |
| Gln | Pro | Val | Pro | Lys 80 | Ala | Ala | Leu | Leu | Asn 85 | Ala | Ile | Arg | Lys | Leu 90 |
| His | Val | Gly | Lys | Val 95 | Gly | Glu | Asn | Gly | Tyr 100 | Val | Glu | Leu | Glu | Asp 105 |
| Asp | Ile | Gly | Arg | Arg 110 | Ala | Glu | Met | Asn | Glu 115 | Leu | Met | Glu | Gln | Thr 120 |
| Ser | Glu | Ile | Ile | Thr 125 | Phe | Ala | Glu | Ala | Gly 130 | Thr | Ala | Arg | Lys | Thr 135 |
| Leu | Arg | Phe | Glu | Ile 140 | Ser | Lys | Glu | Gly | Ser 145 | Asp | Leu | Ser | Val | Val 150 |

| | | | | | | | | | | | | | | |
|---|---|---|---|---|---|---|---|---|---|---|---|---|---|---|
| Glu | Arg | Ala | Glu | Ile 155 | Trp | Leu | Phe | Leu | Lys 160 | Val | Pro | Lys | Ala | Asn 165 |
| Arg | Thr | Arg | Thr | Lys 170 | Val | Ser | Ile | Arg | Leu 175 | Phe | Gln | Gln | Gln | Arg 180 |
| Arg | Pro | Gln | Gly | Ser 185 | Ala | Asp | Ala | Gly | Glu 190 | Glu | Ala | Glu | Asp | Val 195 |
| Gly | Phe | Pro | Glu | Glu 200 | Lys | Ser | Glu | Val | Leu 205 | Ile | Ser | Glu | Lys | Val 210 |
| Val | Asp | Ala | Arg | Lys 215 | Ser | Thr | Trp | His | Ile 220 | Phe | Pro | Val | Ser | Ser 225 |
| Ser | Ile | Gln | Arg | Leu 230 | Leu | Asp | Gln | Gly | Lys 235 | Ser | Ala | Leu | Asp | Ile 240 |
| Arg | Thr | Ala | Cys | Glu 245 | Gln | Cys | His | Glu | Thr 250 | Gly | Ala | Ser | Leu | Val 255 |
| Leu | Leu | Gly | Lys | Lys 260 | Lys | Lys | Lys | Glu | Glu 265 | Glu | Ala | Glu | Gly | Arg 270 |
| Lys | Arg | Asp | Gly | Glu 275 | Gly | Ala | Gly | Val | Asp 280 | Glu | Glu | Lys | Glu | Gln 285 |
| Ser | His | Arg | Pro | Phe 290 | Leu | Met | Leu | Gln | Ala 295 | Arg | Gln | Ser | Glu | Glu 300 |
| His | Pro | His | Arg | Arg 305 | Arg | Arg | Arg | Gly | Leu 310 | Glu | Cys | Asp | Gly | Lys 315 |
| Val | Asn | Ile | Cys | Cys 320 | Lys | Lys | Gln | Phe | Phe 325 | Val | Ser | Phe | Lys | Asp 330 |
| Ile | Gly | Trp | Asn | Asp 335 | Trp | Ile | Ile | Ala | Pro 340 | Ser | Gly | Tyr | His | Ala 345 |
| Asn | Tyr | Cys | Glu | Gly 350 | Glu | Cys | Pro | Ser | His 355 | Ile | Ala | Gly | Thr | Ser 360 |
| Gly | Ser | Ser | Leu | Ser 365 | Phe | His | Ser | Thr | Val 370 | Ile | Asn | His | Tyr | Arg 375 |
| Met | Arg | Gly | His | Ser 380 | Pro | Phe | Ala | Asn | Leu 385 | Lys | Ser | Cys | Cys | Val 390 |
| Pro | Thr | Lys | Leu | Arg 395 | Pro | Met | Ser | Met | Leu 400 | Tyr | Tyr | Asp | Asp | Gly 405 |
| Gln | Asn | Ile | Ile | Lys 410 | Lys | Asp | Ile | Gln | Asn 415 | Met | Ile | Val | Glu | Glu 420 |
| Cys | Gly | Cys | Ser 424 | | | | | | | | | | | |

( 2 ) INFORMATION FOR SEQ ID NO:32:

( i ) SEQUENCE CHARACTERISTICS:
        ( A ) LENGTH: 3588 bases
        ( B ) TYPE: nucleic acid
        ( C ) STRANDEDNESS: single
        ( D ) TOPOLOGY: linear ( x i ) SEQUENCE DESCRIPTION: SEQ ID NO:32:

```
AAAAGGGCCG  TCACCACAAC  TTTGGCTGCC  AGGATGCCCT  TGCTTTGGCT   50
GAGAGGATTT  TTGTTGGCGA  GTTGCTGGAT  TATAGTGAGG  AGTTCCCCCA  100
CCCCAGGATC  CGGGGGGCAC  AGCGCAGCCC  CGGACTGCCC  GTCCTGTGCG  150
CTGGCCACCC  TCCCAAAGGA  TGTACCCAAC  TCTCAGCCGG  AGATGGTGGA  200
AGCCGTCAAG  AAGCACATTT  TAAACATGCT  GCACTTGAAG  AAGAGACCCG  250
ATGTCACCCA  GCCGGTACCC  AAGGCGGCGC  TTCTGAACGC  GATCAGAAAG  300
```

| | | | | | |
|---|---|---|---|---|---|
| CTTCATGTGG | GCAAAGTGGG | GGAGAACGGG | TACGTGGAGC | TGGAGGACGA | 350 |
| CATCGGGAGG | AGGGCGGAAA | TGAATGAACT | CATGGAGCAG | ACCTCGGAGA | 400 |
| TCATCACCTT | CGCGGAAGCA | GGCACCGCCA | GGAAGACGCT | GCGCTTTGAG | 450 |
| ATCTCCAAAG | AGGGCAGTGA | CCTGTCCGTG | GTGGAGCGCG | CCGAAATCTG | 500 |
| GCTCTTCCTG | AAAGTCCCCA | AGGCCAACCG | GACCAGGACC | AAAGTCTCCA | 550 |
| TCCGTCTCTT | TCAACAGCAG | AGGCGCCCGC | AAGGCAGCGC | GGACGCAGGG | 600 |
| GAGGAGGCGG | AGGACGTGGG | CTTCCCGGAG | GAGAAGAGCG | AAGTGCTGAT | 650 |
| TTCGGAGAAG | GTGGTGGATG | CCCGGAAGAG | CACCTGGCAC | ATCTTCCCCG | 700 |
| TCTCCAGCAG | CATCCAGCGC | TTGCTGGACC | AGGGCAAGAG | CGCCCTGGAC | 750 |
| ATCCGGACTG | CCTGCGAGCA | GTGCCACGAG | ACCGGCGCCA | GCTGGTGCT | 800 |
| GCTGGGCAAG | AAGAAGAAGA | AGGAGGAGGA | GGCGGAGGGG | AGGAAGAGGG | 850 |
| ACGGAGAGGG | GGCGGGCGTG | GACGAGGAGA | AGGAGCAGTC | GCACAGACCT | 900 |
| TTCCTCATGC | TGCAGGCCCG | CCAGTCCGAA | GAGCACCCCC | ACCGCCGCCG | 950 |
| CCGGCGGGGC | CTGGAGTGCG | ACGGCAAGGT | CAACATCTGC | TGTAAGAAGC | 1000 |
| AGTTCTTTGT | CAGTTTCAAG | GACATCGGCT | GGAACGACTG | GATCATCGCT | 1050 |
| CCGTCCGGCT | ACCACGCCAA | CTACTGCGAG | GGCGAGTGCC | CCAGCCACAT | 1100 |
| AGCGGGCACG | TCGGGCTCCT | CGCTCTCGTT | CCACTCGACG | GTCATCAACC | 1150 |
| ACTACCGCAT | GCGCGGCCAC | AGCCCCTTCG | CCAACCTCAA | GTCGTGCTGC | 1200 |
| GTCCCCACCA | AGCTGAGGCC | CATGTCCATG | CTGTACTACG | ACGACGGGCA | 1250 |
| GAACATCATC | AAGAAGGACA | TCCAGAACAT | GATCGTGGAG | GAGTGCGGGT | 1300 |
| GCTCCTAGAG | CGCCGGCCGG | GGCCCGGGGC | CCGGGGCCCG | GGACGACGG | 1350 |
| CGGCCACGCG | AAGACACGTT | TACGGCCTCT | GACCTAGGCG | ACCGCAAACA | 1400 |
| TGGAAATGAA | CAAAATAAC | CATAAACTAA | AAACAAAACC | TGAAACAGAT | 1450 |
| GAAGGAAGAC | GTGGAAAAAT | TCCGTAGCCA | GGGCTCGGCG | ATGACACCGT | 1500 |
| GAAGGAGACG | GGACTCGGGG | GGGAGGGAGA | GGCAGAACGT | GGGGGGCGGG | 1550 |
| GCGGGGGGGG | ACGACCCTTC | CTTTCTTCCT | CCAGCATCGG | AGTGGGGACA | 1600 |
| GCAGTTGCTC | CAACGGGAAT | ATTGTCCTCT | CCTTTTCAGT | TCCCTGTCAG | 1650 |
| TGTGAGCCTC | GAAGTCAGCT | TGTCTGGTCT | GCAGCCATGT | GGGCTGGCAC | 1700 |
| AACCCAAATA | GCGTCTAGAA | AGCCATGAGT | TTGAAAGGGC | CAGTTATAGG | 1750 |
| CACTTTCCCA | CCCAGTAACC | CAGGTCGTAA | GGTATGTCTG | TGTGACCCTC | 1800 |
| TCTCTGTGTA | TATCAGCCCA | TGCACACACC | TACAAAGACA | CACACACACA | 1850 |
| CACACACACA | CACACACACA | CACACACACA | CACACACACA | CACACACAAC | 1900 |
| TTCCTCTGAC | TTTTCTGAGA | CAAAGAGGTG | GGTATAAACT | GACTCCAGGA | 1950 |
| AAACTCGAGT | GGGAAAACGT | GCCCTTTGGG | TTGGGACAAT | TTAGATGGTG | 2000 |
| GAGCAAAGCA | AAAAGGAGGC | AACGGCAAGT | ATGTTCGTGA | TGGGCCTGTG | 2050 |
| CCCCTGAGGG | AGGGGTGAGG | AAGTCCCTAA | GGGTGACCTT | AGCCAGACAG | 2100 |
| TGACTCTAGA | AGAAGGGGCT | CGACAGGGTC | ATGTAAAGAG | AGGAGCTAAT | 2150 |
| TCAGTCAGAA | AACCCCTGGC | ACTCAAGAGA | ACCACCGTGG | GAGTTCCCGT | 2200 |
| CGTGGCGCAG | TGGTTAACGA | ATCCGACTAG | GAACCATGAG | GTTGAGGGTT | 2250 |
| CGATCCCTGC | CCTTACTCAG | TGGGTTAACG | ATCCGGCGTT | GCCGTGAGCT | 2300 |

```
GTGGTGCAGG  TTGCAGACGC  GGCTCGGATC  CTGCGTTGCT  GTGGCTCTGG  2350

CGTAGGCGGT  GGCTACAGCT  CCGATTCAAC  CCCTAGCCTG  GAACCTCCA   2400

TATGCCGCGG  CCCAAGAAAT  AGCAAAAAAA  AAAAAAAAGA  GAACCACCGT  2450

GGAGGCCCGT  AGCCAGAGCC  GGTCCCTTTT  AACCCAAGTA  GGGAAGGGGA  2500

ATGAGACTAA  GAAGTGAATT  TCTTGACAGT  CGCAGGCCAG  AAAGAGGCAG  2550

AGGGACGTCA  GTGCCTCTTC  CTGGGAGGCG  GCCCCTCCG   TAGGCTGCAC  2600

AGGAGTTCGC  TGAGGGGCCG  GCGAGGAAAG  GTGTGGGACA  GAGGTGGAGG  2650

CATGTATTCC  ACCTTTCGCT  TTAGCAGTAT  CTGAAGTCAC  GGCGAGACTA  2700

AGGGCTTCCA  TTCAGTCCCG  TGTATTGCAA  GAATCCATGA  ATTATCTGAA  2750

TCATTTCGCC  ACTTAATCAA  CCCTACAGTT  GTTCACGTG   TATCTTGTTT  2800

GCTGGTTAAA  CCCTACACTA  TTTGAGAACC  AAAGCTGTGC  TATTGCTCTA  2850

GCACCAGTCT  CAGGGCCACG  GGTCCCTCTT  CCAGAGTCTC  CTACCTTCAG  2900

TACCTCTTGC  CAGGAACACA  TTCCTCTCCT  GCCCAGTCAC  TCTCCAAGGA  2950

GATTCTGTCC  CCTAAATATC  TCTGGAAGCC  ATCTTTTCTC  CAAGCTGTCA  3000

TCACCGCTTG  TCCAGACTGC  TGCTTCCTCG  CCAGGTCTCC  CATCTCCCTT  3050

CCTGTCCTCC  ACACACAGCC  GCGTGAGCTC  TGAAAAACAA  ACCTAAACAC  3100

CTGACTTTCC  TCATTCAGAT  TCTTCAGTGG  CTTCCCGTTG  CTTTTGGAAT  3150

AAAGTCCTAA  ATTCAAAGAG  CTTGCATAAG  TCAGCCTGTA  CCATGCATCG  3200

ACCCCCTTGG  TTCCCTAAGT  TCCAGTCACA  TTGGCTGGCT  TTCCGTCTTC  3250

CTGCCGCAAA  GCCAGCACAC  GGACTGTTCT  CTCCGCTTGT  AACACTCCCA  3300

TTTTCCACCT  TTTAATCCTA  AATGTTTCTT  CCTCGGGGAG  ACCTTTTCTG  3350

ATTTTGTGAT  GTAGGTCAAG  ACTTTTAGTT  AAATCTTCTC  TTAGCACCAT  3400

GCCTGTTTCA  TAGCACTTAT  TACAATCATA  ATGTTTACAG  TAGAGACGTA  3450

ATTGGCTGGC  AGGCTGCTAG  ATTGTAAGCT  CATGAGGGCA  GAAATCACGT  3500

CCATCTTGTT  CACTGCTGTA  TTCCCAGTGT  CGGGCACACA  GTTGTTGCTC  3550

AATAAATTTG  ACTTAATGAA  CTCAAAAAAA  AAAAAAA                 3588
```

( 2 ) INFORMATION FOR SEQ ID NO:33:

( i ) SEQUENCE CHARACTERISTICS:
        ( A ) LENGTH: 349 amino acids
        ( B ) TYPE: amino acid
        ( D ) TOPOLOGY: linear ( x i ) SEQUENCE DESCRIPTION: SEQ ID NO:33:

```
Arg  Ala  Ala  Gly  Ala  Glu  Glu  Glu  Leu  Gly  Arg  Leu  Asp  Gly  Asp
 1                 5                        10                       15

Phe  Leu  Glu  Ala  Val  Lys  Arg  His  Ile  Leu  Asn  Arg  Leu  Gln  Met
                    20                       25                       30

Arg  Gly  Arg  Pro  Asn  Ile  Thr  His  Ala  Val  Pro  Lys  Ala  Ala  Met
                    35                       40                       45

Val  Thr  Ala  Leu  Arg  Lys  Leu  His  Ala  Gly  Lys  Val  Arg  Glu  Asp
                    50                       55                       60

Gly  Arg  Val  Glu  Ile  Pro  His  Leu  Asp  Gly  His  Ala  Ser  Pro  Gly
                    65                       70                       75

Ala  Asp  Gly  Gln  Glu  Arg  Val  Ser  Glu  Ile  Ile  Ser  Phe  Ala  Glu
                    80                       85                       90
```

```
Thr  Asp  Gly  Leu  Ala  Ser  Ser  Arg  Val  Arg  Leu  Tyr  Phe  Phe  Ile
                    95                       100                      105

Ser  Asn  Glu  Gly  Asn  Gln  Asn  Leu  Phe  Val  Val  Gln  Ala  Ser  Leu
                    110                      115                      120

Trp  Leu  Tyr  Leu  Lys  Leu  Leu  Pro  Tyr  Val  Leu  Glu  Lys  Gly  Ser
                    125                      130                      135

Arg  Arg  Lys  Val  Arg  Val  Lys  Val  Tyr  Phe  Gln  Glu  Pro  Gly  His
                    140                      145                      150

Gly  Asp  Arg  Trp  Asp  Val  Val  Glu  Lys  Arg  Val  Asp  Leu  Lys  Arg
                    155                      160                      165

Ser  Gly  Trp  His  Thr  Leu  Pro  Leu  Thr  Glu  Ala  Ile  Gln  Ala  Leu
                    170                      175                      180

Phe  Glu  Arg  Gly  Glu  Arg  Arg  Leu  Asn  Leu  Asp  Val  Gln  Cys  Asp
                    185                      190                      195

Gly  Cys  Gln  Glu  Leu  Ala  Val  Val  Pro  Val  Phe  Val  Asp  Pro  Gly
                    200                      205                      210

Glu  Glu  Ser  His  Arg  Pro  Phe  Val  Val  Val  Gln  Ala  Arg  Leu  Gly
                    215                      220                      225

Asp  Ser  Arg  His  Arg  Ile  Arg  Lys  Arg  Gly  Leu  Glu  Cys  Asp  Gly
                    230                      235                      240

Arg  Thr  Asn  Leu  Cys  Cys  Arg  Gln  Gln  Phe  Phe  Ile  Asp  Phe  Arg
                    245                      250                      255

Leu  Ile  Gly  Trp  Ser  Asp  Trp  Ile  Ile  Ala  Pro  Thr  Gly  Tyr  Tyr
                    260                      265                      270

Gly  Asn  Tyr  Cys  Glu  Gly  Ser  Cys  Pro  Ala  Tyr  Leu  Ala  Gly  Val
                    275                      280                      285

Pro  Gly  Ser  Ala  Ser  Ser  Phe  His  Thr  Ala  Val  Val  Asn  Gln  Tyr
                    290                      295                      300

Arg  Met  Arg  Gly  Leu  Asn  Pro  Gly  Thr  Val  Asn  Ser  Cys  Cys  Ile
                    305                      310                      315

Pro  Thr  Lys  Leu  Ser  Thr  Met  Ser  Met  Leu  Tyr  Phe  Asp  Asp  Glu
                    320                      325                      330

Tyr  Asn  Ile  Val  Lys  Arg  Asp  Val  Pro  Asn  Met  Ile  Val  Glu  Glu
                    335                      340                      345

Cys  Gly  Cys  Ala
                349
```

( 2 ) INFORMATION FOR SEQ ID NO:34:

( i ) SEQUENCE CHARACTERISTICS:
            ( A ) LENGTH: 1524 bases
            ( B ) TYPE: nucleic acid
            ( C ) STRANDEDNESS: single
            ( D ) TOPOLOGY: linear ( x i ) SEQUENCE DESCRIPTION: SEQ ID NO:34:

```
CGGGCGGCGG  GGGCGGAGGA  GGAGCTGGGC  CGGCTGGACG  GCGACTTCCT   50

GGAGGCGGTG  AAGCGCCACA  TCTTGAACCG  CCTGCAGATG  CGGGGCCGAC  100

CCAACATCAC  CCATGCCGTG  CCCAAGGCCG  CCATGGTCAC  GGCCCTGCGC  150

AAACTACATG  CGGGCAAGGT  GCGCGAGGAC  GGCCGGGTGG  AGATCCCGCA  200

CCTGGACGGC  CACGCCAGCC  CTGGCGCCGA  CGGCCAAGAG  CGGGTCTCCG  250

AGATCATCAG  CTTCGCAGAG  ACAGATGGCC  TCGCCTCCTC  CCGGGTCCGC  300

CTGTACTTCT  TCATCTCCAA  CGAGGGTAAC  CAGAACCTGT  TCGTGGTACA  350

GGCCAGTCTG  TGGCTCTACC  TGAAGCTGCT  GCCTTACGTT  CTGGAGAAGG  400
```

```
GCAGCCGGCG CAAGGTTCGG GTCAAGGTGT ACTTCCAGGA GCCGGGCCAC  450
GGCGACCGCT GGGACGTGGT GGAGAAGCGT GTGGACCTGA AGCGCAGCGG  500
CTGGCACACC CTCCCGCTCA CCGAGGCCAT CCAGGCCCTG TTTGAGCGGG  550
GCGAGCGGCG CCTCAACCTG GACGTGCAGT GCGACGGCTG CCAGGAGCTG  600
GCCGTGGTGC CCGTGTTTGT GGACCCGGGC GAGGAGTCAC ACCGGCCCTT  650
CGTGGTGGTG CAGGCGCGAC TGGGTGACAG CAGGCACCGC ATCCGCAAGC  700
GGGGCCTGGA GTGTGACGGC CGGACCAACC TCTGTTGCAG GCAACAGTTC  750
TTCATCGACT TCCGCCTCAT GGCTGGAGT  GACTGGATCA TCGCGCCCAC  800
CGGCTACTAT GGGAACTACT GTGAGGGCAG CTGTCCGGCC TACCTGGCAG  850
GGGTGCCAGG CTCCGCCTCA TCCTTCCACA CGGCCGTGGT CAACCAGTAC  900
CGCATGCGGG GCCTGAACCC GGGCACAGTG AACTCCTGCT GCATCCCCAC  950
CAAGCTGAGC ACCATGTCCA TGCTCTACTT CGATGACGAG TACAACATCG 1000
TCAAGCGGGA CGTGCCCAAC ATGATCGTGG AGGAGTGTGG CTGTGCCTGA 1050
AAGCATGGGC TCGGGACTGT CCCTGCGGGC ACGGGGCACA TGGCGGGGGG 1100
GTGTGGTCTT GCCGCTGGGT GGCCCGGCAG GTGCCAGGGT GGGAGGCCTG 1150
AGATACTTTC CTACTTCTTT ATTGAGCAAT CAGTCGAAAC CAGAGGGCGG 1200
ACCCTCCGTG GACACGAAAG ACTTGAAAAT GCACACGTAG ATGCCCGCAG 1250
CAGACGCCTC CTGCCACCCA CACAGCAGCC TCCGGGATAC CAGCAAATGG 1300
ATGCAGTGAC AAATGGCAGC TTAGCTACAA ACGCCTGTCA GTCGGAGAGA 1350
AAGGGTGAGC AGCCACCATT CCCACCAGCT GGCCCGGCCA CTCTGAATCG 1400
CTCCTTTCGA GCACACAGAA AAGCACAAAG ACAGAGACAC CGAGAGAGAG 1450
AGAGAGAGAG AGAGACAGAC AGACAGACAG AGAGAGAGAG CGAGAGAGAG 1500
AGCGAGAGAG AGAGAGAGAG AGAG                            1524
```

( 2 ) INFORMATION FOR SEQ ID NO:35:

( i ) SEQUENCE CHARACTERISTICS:
( A ) LENGTH: 116 amino acids
( B ) TYPE: amino acid
( D ) TOPOLOGY: linear ( x i ) SEQUENCE DESCRIPTION: SEQ ID NO:35:

```
Gly Leu Glu Cys Asp Gly Lys Val Asn Ile Cys Cys Lys Lys Gln
 1               5                  10                  15

Phe Phe Val Ser Phe Lys Asp Ile Gly Trp Asn Asp Trp Ile Ile
                20                  25                  30

Ala Pro Ser Gly Tyr His Ala Asn Tyr Cys Glu Gly Glu Cys Pro
                35                  40                  45

Ser His Ile Ala Gly Thr Ser Gly Ser Ser Leu Ser Phe His Ser
                50                  55                  60

Thr Val Ile Asn His Tyr Arg Met Arg Gly His Ser Pro Phe Ala
                65                  70                  75

Asn Leu Lys Ser Cys Cys Val Pro Thr Lys Leu Arg Pro Met Ser
                80                  85                  90

Met Leu Tyr Tyr Asp Asp Gly Gln Asn Ile Ile Lys Lys Asp Ile
                95                 100                 105

Gln Asn Met Ile Val Glu Glu Cys Gly Cys Ser
               110                 115 116
```

( 2 ) INFORMATION FOR SEQ ID NO:36:

( i ) SEQUENCE CHARACTERISTICS:
        ( A ) LENGTH: 112 amino acids
        ( B ) TYPE: amino acid
        ( D ) TOPOLOGY: linear ( x i ) SEQUENCE DESCRIPTION: SEQ ID NO:36:

```
Ala  Leu  Asp  Thr  Asn  Tyr  Cys  Phe  Ser  Ser  Thr  Glu  Lys  Asn  Cys
 1                 5                      10                         15

Cys  Val  Arg  Gln  Leu  Tyr  Ile  Asp  Phe  Arg  Lys  Asp  Leu  Gly  Trp
                20                      25                         30

Lys  Trp  Ile  His  Glu  Pro  Lys  Gly  Tyr  His  Ala  Asn  Phe  Cys  Leu
                35                      40                         45

Gly  Pro  Cys  Pro  Tyr  Ile  Trp  Ser  Leu  Asp  Thr  Gln  Tyr  Ser  Lys
                50                      55                         60

Val  Leu  Ala  Leu  Tyr  Asn  Gln  His  Asn  Pro  Gly  Ala  Ser  Ala  Ala
                65                      70                         75

Pro  Cys  Cys  Val  Pro  Gln  Ala  Leu  Glu  Pro  Leu  Pro  Ile  Val  Tyr
                80                      85                         90

Tyr  Val  Gly  Arg  Lys  Pro  Lys  Val  Glu  Gln  Leu  Ser  Asn  Met  Ile
                95                     100                        105

Val  Arg  Ser  Cys  Lys  Cys  Ser
               110            112
```

( 2 ) INFORMATION FOR SEQ ID NO:37:

( i ) SEQUENCE CHARACTERISTICS:
        ( A ) LENGTH: 115 amino acids
        ( B ) TYPE: amino acid
        ( D ) TOPOLOGY: linear ( x i ) SEQUENCE DESCRIPTION: SEQ ID NO:37:

```
Gly  Leu  Glu  Cys  Asp  Gly  Arg  Thr  Asn  Leu  Cys  Cys  Arg  Gln  Gln
 1                 5                      10                         15

Phe  Phe  Ile  Asp  Phe  Arg  Leu  Ile  Gly  Trp  Ser  Asp  Trp  Ile  Ile
                20                      25                         30

Ala  Pro  Thr  Gly  Tyr  Tyr  Gly  Asn  Tyr  Cys  Glu  Gly  Ser  Cys  Pro
                35                      40                         45

Ala  Tyr  Leu  Ala  Gly  Val  Pro  Gly  Ser  Ala  Ser  Ser  Phe  His  Thr
                50                      55                         60

Ala  Val  Val  Asn  Gln  Tyr  Arg  Met  Arg  Gly  Leu  Asn  Pro  Gly  Thr
                65                      70                         75

Val  Asn  Ser  Cys  Cys  Ile  Pro  Thr  Lys  Leu  Ser  Thr  Met  Ser  Met
                80                      85                         90

Leu  Tyr  Phe  Asp  Asp  Glu  Tyr  Asn  Ile  Val  Lys  Arg  Asp  Val  Pro
                95                     100                        105

Asn  Met  Ile  Val  Glu  Glu  Cys  Gly  Cys  Ala
               110                    115
```

( 2 ) INFORMATION FOR SEQ ID NO:38:

( i ) SEQUENCE CHARACTERISTICS:
        ( A ) LENGTH: 116 amino acids
        ( B ) TYPE: amino acid
        ( D ) TOPOLOGY: linear ( x i ) SEQUENCE DESCRIPTION: SEQ ID NO:38:

```
Arg  Pro  Pro  Glu  Glu  Pro  Ala  Val  His  Ala  Asp  Cys  His  Arg  Ala
```

| | 1 | | | | 5 | | | | | 10 | | | | | 15 |
|---|---|---|---|---|---|---|---|---|---|---|---|---|---|---|---|
| Ser | Leu | Asn | Ile | Ser | Phe | Gln | Glu | Leu | Gly | Trp | Asp | Arg | Trp | Ile |
| | | | | 20 | | | | | 25 | | | | | 30 |
| Val | His | Pro | Pro | Ser | Phe | Ile | Phe | His | Tyr | Cys | His | Gly | Gly | Cys |
| | | | | 35 | | | | | 40 | | | | | 45 |
| Gly | Leu | Pro | Thr | Leu | Pro | Asn | Leu | Pro | Leu | Ser | Val | Pro | Gly | Ala |
| | | | | 50 | | | | | 55 | | | | | 60 |
| Pro | Pro | Thr | Pro | Val | Gln | Pro | Leu | Leu | Val | Pro | Gly | Ala | Gln |
| | | | | 65 | | | | | 70 | | | | | 75 |
| Pro | Cys | Cys | Ala | Ala | Leu | Pro | Gly | Thr | Met | Arg | Ser | Leu | Arg | Val |
| | | | | 80 | | | | | 85 | | | | | 90 |
| Arg | Thr | Thr | Ser | Asp | Gly | Gly | Tyr | Ser | Phe | Lys | Tyr | Glu | Thr | Val |
| | | | | 95 | | | | | 100 | | | | | 105 |
| Pro | Asn | Leu | Leu | Thr | Gln | His | Cys | Ala | Cys | Ile | | | | |
| | | | | 110 | | | | | 115 | 116 | | | | |

( 2 ) INFORMATION FOR SEQ ID NO:39:

( i ) SEQUENCE CHARACTERISTICS:
        ( A ) LENGTH: 351 amino acids
        ( B ) TYPE: amino acid
        ( D ) TOPOLOGY: linear ( x i ) SEQUENCE DESCRIPTION: SEQ ID NO:39:

| Gly | Val | Ser | Ser | Gln | Gly | Leu | Glu | Leu | Ala | Arg | Glu | Leu | Val | Leu |
|---|---|---|---|---|---|---|---|---|---|---|---|---|---|---|
| 1 | | | | 5 | | | | | 10 | | | | | 15 |
| Ala | Lys | Val | Arg | Ala | Leu | Phe | Leu | Asp | Ala | Leu | Gly | Pro | Pro | Ala |
| | | | | 20 | | | | | 25 | | | | | 30 |
| Val | Thr | Arg | Glu | Gly | Gly | Asp | Pro | Gly | Val | Arg | Arg | Leu | Pro | Arg |
| | | | | 35 | | | | | 40 | | | | | 45 |
| Arg | His | Ala | Leu | Gly | Gly | Phe | Thr | His | Arg | Gly | Ser | Glu | Pro | Glu |
| | | | | 50 | | | | | 55 | | | | | 60 |
| Glu | Glu | Glu | Asp | Val | Ser | Gln | Ala | Ile | Leu | Phe | Pro | Ala | Thr | Asp |
| | | | | 65 | | | | | 70 | | | | | 75 |
| Ala | Ser | Cys | Glu | Asp | Lys | Ser | Ala | Ala | Arg | Gly | Leu | Ala | Gln | Glu |
| | | | | 80 | | | | | 85 | | | | | 90 |
| Ala | Glu | Glu | Gly | Leu | Phe | Arg | Tyr | Met | Phe | Arg | Pro | Ser | Gln | His |
| | | | | 95 | | | | | 100 | | | | | 105 |
| Thr | Arg | Ser | Arg | Gln | Val | Thr | Ser | Ala | Gln | Leu | Trp | Phe | His | Thr |
| | | | | 110 | | | | | 115 | | | | | 120 |
| Gly | Leu | Asp | Arg | Gln | Gly | Thr | Ala | Ala | Ser | Asn | Ser | Ser | Glu | Pro |
| | | | | 125 | | | | | 130 | | | | | 135 |
| Leu | Leu | Gly | Leu | Leu | Ala | Leu | Ser | Pro | Gly | Gly | Pro | Val | Ala | Val |
| | | | | 140 | | | | | 145 | | | | | 150 |
| Pro | Met | Ser | Leu | Gly | His | Ala | Pro | Pro | His | Trp | Ala | Val | Leu | His |
| | | | | 155 | | | | | 160 | | | | | 165 |
| Leu | Ala | Thr | Ser | Ala | Leu | Ser | Leu | Leu | Thr | His | Pro | Val | Leu | Val |
| | | | | 170 | | | | | 175 | | | | | 180 |
| Leu | Leu | Leu | Arg | Cys | Pro | Leu | Cys | Thr | Cys | Ser | Ala | Arg | Pro | Glu |
| | | | | 185 | | | | | 190 | | | | | 195 |
| Ala | Thr | Pro | Phe | Leu | Val | Ala | His | Thr | Arg | Thr | Arg | Pro | Pro | Ser |
| | | | | 200 | | | | | 205 | | | | | 210 |
| Gly | Gly | Glu | Arg | Ala | Arg | Arg | Ser | Thr | Pro | Leu | Met | Ser | Trp | Pro |
| | | | | 215 | | | | | 220 | | | | | 225 |
| Trp | Ser | Pro | Ser | Ala | Leu | Arg | Leu | Leu | Gln | Arg | Pro | Pro | Glu | Glu |
| | | | | 230 | | | | | 235 | | | | | 240 |

| Pro | Ala | Ala | His | Ala<br>245 | Asn | Cys | His | Arg | Val<br>250 | Ala | Leu | Asn | Ile | Ser<br>255 |

| Phe | Gln | Glu | Leu | Gly<br>260 | Trp | Glu | Arg | Trp | Ile<br>265 | Val | Tyr | Pro | Pro | Ser<br>270 |

| Phe | Ile | Phe | His | Tyr<br>275 | Cys | His | Gly | Gly | Cys<br>280 | Gly | Leu | His | Ile | Pro<br>285 |

| Pro | Asn | Leu | Ser | Leu<br>290 | Pro | Val | Pro | Gly | Ala<br>295 | Pro | Pro | Thr | Pro | Ala<br>300 |

| Gln | Pro | Tyr | Ser | Leu<br>305 | Leu | Pro | Gly | Ala | Gln<br>310 | Pro | Cys | Cys | Ala | Ala<br>315 |

| Leu | Pro | Gly | Thr | Met<br>320 | Arg | Pro | Leu | His | Val<br>325 | Arg | Thr | Thr | Ser | Asp<br>330 |

| Gly | Gly | Tyr | Ser | Phe<br>335 | Lys | Tyr | Glu | Thr | Val<br>340 | Pro | Asn | Leu | Leu | Thr<br>345 |

| Gln | His | Cys | Ala | Cys<br>350 | Ile<br>351 |

( 2 ) INFORMATION FOR SEQ ID NO:40:

( i ) SEQUENCE CHARACTERISTICS:
        ( A ) LENGTH: 1237 bases
        ( B ) TYPE: nucleic acid
        ( C ) STRANDEDNESS: single
        ( D ) TOPOLOGY: linear ( x i ) SEQUENCE DESCRIPTION: SEQ ID NO:40:

```
GTGGGGTCAG CAGCCAGGGG CTGGAGCTGG CCCGGGAACT TGTTCTGGCC    50
AAGGTGAGGG CCCTGTTCTT GGATGCCTTG GGGCCCCCCG CGGTGACCAG   100
GGAAGGTGGG GACCCTGGAG TCAGGCGGCT GCCCCGAAGA CATGCCCTGG   150
GGGGCTTCAC ACACAGGGGC TCTGAGCCCG AGGAAGAGGA GGATGTCTCC   200
CAAGCCATCC TTTTCCCAGC CACAGATGCC AGCTGTGAGG ACAAGTCAGC   250
TGCCAGAGGG CTGGCCCAGG AGGCTGAGGA GGGCCTCTTC AGATACATGT   300
TCCGGCCATC CCAGCATACA CGCAGCCGCC AGGTGACTTC AGCCCAGCTG   350
TGGTTCCACA CCGGGCTGGA CAGGCAGGGC ACAGCAGCCT CCAATAGCTC   400
TGAGCCCCTG CTAGGCCTGC TGGCACTGTC ACCGGGAGGA CCCGTGGCTG   450
TGCCCATGTC TTTGGGCCAT GCTCCCCCTC ACTGGGCCGT GCTGCACCTG   500
GCCACCTCTG CTCTCTCTCT GCTGACCCAC CCCGTCCTGG TGCTGCTGCT   550
GCGCTGTCCC CTCTGTACCT GCTCAGCCCG GCCTGAGGCC ACGCCCTTCC   600
TGGTGGCCCA CACTCGGACC AGACCACCCA GTGGAGGGGA GAGAGCCCGA   650
CGCTCAACTC CCCTGATGTC CTGGCCTTGG TCTCCCTCTG CTCTGCGCCT   700
GCTGCAGAGG CCTCCGGAGG AACCGGCTGC CCATGCCAAC TGCCACAGAG   750
TAGCACTGAA CATCTCCTTC CAGGAGCTGG GCTGGGAACG GTGGATCGTG   800
TACCCTCCCA GTTTCATCTT CCACTACTGT CATGGTGGTT GTGGGCTGCA   850
CATCCCACCA AACCTGTCCC TTCCAGTCCC TGGGGCTCCC CCTACCCCAG   900
CCCAGCCCTA CTCCTTGCTG CCAGGGGCCC AGCCCTGCTG TGCTGCTCTC   950
CCAGGGACCA TGAGGCCCCT ACATGTCCGC ACCACCTCGG ATGGAGGTTA  1000
CTCTTTCAAG TATGAGACAG TGCCCAACCT TCTCACGCAG CACTGTGCTT  1050
GTATCTAAGG GTGGGGGGTC TTCCTTCTTA ATCCCATGGC TGGTGGCCAC  1100
```

-continued

```
GCCCCCACCA TCATCAGCTG GGAGGAAAGG CAGAGTTGGG AAATAGATGG    1150

CTCCCACTCC TCCTCCTTT  CACTTCTCTG CCTATGGGCT ACCCTCCCCA    1200

CCCCACTTCT ATCTCAATAA AGAACACAGT GCATATG                  1237
```

( 2 ) INFORMATION FOR SEQ ID NO:41:

( i ) SEQUENCE CHARACTERISTICS:
        ( A ) LENGTH: 426 amino acids
        ( B ) TYPE: amino acid
        ( D ) TOPOLOGY: linear ( x i ) SEQUENCE DESCRIPTION: SEQ ID NO:41:

```
Met Pro Leu Leu Trp Leu Arg Gly Phe Leu Leu Ala Ser Cys Trp
 1               5                  10                  15

Ile Ile Val Arg Ser Ser Pro Thr Pro Gly Ser Glu Gly His Ser
                20                  25                  30

Ala Ala Pro Asp Cys Pro Ser Cys Ala Leu Ala Ala Leu Pro Lys
                35                  40                  45

Asp Val Pro Asn Ser Gln Pro Glu Met Val Glu Ala Val Lys Lys
                50                  55                  60

His Ile Leu Asn Met Leu His Leu Lys Lys Arg Pro Asp Val Thr
                65                  70                  75

Gln Pro Val Pro Lys Ala Ala Leu Leu Asn Ala Ile Arg Lys Leu
                80                  85                  90

His Val Gly Lys Val Gly Glu Asn Gly Tyr Val Glu Ile Glu Asp
                95                  100                 105

Asp Ile Gly Arg Arg Ala Glu Met Asn Glu Leu Met Glu Gln Thr
                110                 115                 120

Ser Glu Ile Ile Thr Phe Ala Glu Ser Gly Thr Ala Arg Lys Thr
                125                 130                 135

Leu His Phe Glu Ile Ser Lys Glu Gly Ser Asp Leu Ser Val Val
                140                 145                 150

Glu Arg Ala Glu Val Trp Leu Phe Leu Lys Val Pro Lys Ala Asn
                155                 160                 165

Arg Thr Arg Thr Lys Val Thr Ile Arg Leu Phe Gln Gln Gln Lys
                170                 175                 180

His Pro Gln Gly Ser Leu Asp Thr Gly Glu Glu Ala Glu Glu Val
                185                 190                 195

Gly Leu Lys Gly Glu Arg Ser Glu Leu Leu Leu Ser Glu Lys Val
                200                 205                 210

Val Asp Ala Arg Lys Ser Thr Trp His Val Phe Pro Val Ser Ser
                215                 220                 225

Ser Ile Gln Arg Leu Leu Asp Gln Gly Lys Ser Ser Leu Asp Val
                230                 235                 240

Arg Ile Ala Cys Glu Gln Cys Gln Glu Ser Gly Ala Ser Leu Val
                245                 250                 255

Leu Leu Gly Lys Lys Lys Lys Lys Glu Glu Gly Glu Gly Lys
                260                 265                 270

Lys Lys Gly Gly Gly Glu Gly Gly Ala Gly Ala Asp Glu Glu Lys
                275                         280                 285

Glu Gln Ser His Arg Pro Phe Leu Met Leu Gln Ala Arg Gln Ser
                290                 295                 300

Glu Asp His Pro His Arg Arg Arg Arg Arg Gly Leu Glu Cys Asp
                305                 310                 315

Gly Lys Val Asn Ile Cys Cys Lys Lys Gln Phe Phe Val Ser Phe
```

|     |     |     |     |     | 320 |     |     |     |     | 325 |     |     |     |     | 330 |
| --- | --- | --- | --- | --- | --- | --- | --- | --- | --- | --- | --- | --- | --- | --- | --- |
| Lys | Asp | Ile | Gly | Trp | Asn | Asp | Trp | Ile | Ile | Ala | Pro | Ser | Gly | Tyr |
|     |     |     |     | 335 |     |     |     |     | 340 |     |     |     |     | 345 |
| His | Ala | Asn | Tyr | Cys | Glu | Gly | Glu | Cys | Pro | Ser | His | Ile | Ala | Gly |
|     |     |     |     | 350 |     |     |     |     | 355 |     |     |     |     | 360 |
| Thr | Ser | Gly | Ser | Ser | Leu | Ser | Phe | His | Ser | Thr | Val | Ile | Asn | His |
|     |     |     |     | 365 |     |     |     |     | 370 |     |     |     |     | 375 |
| Tyr | Arg | Met | Arg | Gly | His | Ser | Pro | Phe | Ala | Asn | Leu | Lys | Ser | Cys |
|     |     |     |     | 380 |     |     |     |     | 385 |     |     |     |     | 390 |
| Cys | Val | Pro | Thr | Lys | Leu | Arg | Pro | Met | Ser | Met | Leu | Tyr | Tyr | Asp |
|     |     |     |     | 395 |     |     |     |     | 400 |     |     |     |     | 405 |
| Asp | Gly | Gln | Asn | Ile | Ile | Lys | Lys | Asp | Ile | Gln | Asn | Met | Ile | Val |
|     |     |     |     | 410 |     |     |     |     | 415 |     |     |     |     | 420 |
| Glu | Glu | Cys | Gly | Cys | Ser |
|     |     |     |     | 425 | 426 |

( 2 ) INFORMATION FOR SEQ ID NO:42:

( i ) SEQUENCE CHARACTERISTICS:
        ( A ) LENGTH: 1633 bases
        ( B ) TYPE: nucleic acid
        ( C ) STRANDEDNESS: single
        ( D ) TOPOLOGY: linear ( x i ) SEQUENCE DESCRIPTION: SEQ ID NO:42:

```
TGCTCCCTGA CAGCCACAAA CCTACAGCAC TGACTGCATT CAGAGAGGAA   50
CCTGCAAACA AAACTTCACA GAAAACTTTT TGTTCTTGTT CCAGAGAATT  100
TGCTGAAGAG GAGAAGGAAA AAAAAAACAC CAAAAAAAAA AATAAAAAAA  150
TCCACACACA CAAAAAACCT GCGCGTGAGG GGGGAGGAAA AGCAGGGCCT  200
TTTAAAAAGG CAATCACAAC AACTTTTGCT GCCAGGATGC CCTTGCTTTG  250
GCTGAGAGGA TTTCTGTTGG CAAGTTGCTG GATTATAGTG AGGAGTTCCC  300
CCACCCCAGG ATCCGAGGGG CACAGCGCGG CCCCCGACTG TCCGTCCTGT  350
GCGCTGGCCG CCCTCCCAAA GGATGTACCC AACTCTCAGC CAGAGATGGT  400
GGAGGCCGTC AAGAAGCACA TTTTAAACAT GCTGCACTTG AAGAAGAGAC  450
CCGATGTCAC CCAGCCGGTA CCCAAGGCGG CGCTTCTGAA CGCGATCAGA  500
AAGCTTCATG TGGGCAAAGT CGGGGAGAAC GGGTATGTGG AGATAGAGGA  550
TGACATTGGA AGGAGGGCAG AAATGAATGA ACTTATGGAG CAGACCTCGG  600
AGATCATCAC GTTTGCCGAG TCAGGAACAG CCAGGAAGAC GCTGCACTTC  650
GAGATTTCCA AGGAAGGCAG TGACCTGTCA GTGGTGGAGC GTGCAGAAGT  700
CTGGCTCTTC CTAAAAGTCC CCAAGGCCAA CAGGACCAGG ACCAAAGTCA  750
CCATCCGCCT CTTCCAGCAG CAGAAGCACC CGCAGGGCAG CTTGGACACA  800
GGGGAAGAGG CCGAGGAAGT GGGCTTAAAG GGGGAGAGGA GTGAACTGTT  850
GCTCTCTGAA AAAGTAGTAG ACGCTCGGAA GAGCACCTGG CATGTCTTCC  900
CTGTCTCCAG CAGCATCCAG CGGTTGCTGG ACCAGGGCAA GAGCTCCCTG  950
GACGTTCGGA TTGCCTGTGA GCAGTGCCAG GAGAGTGGCG CCAGCTTGGT 1000
TCTCCTGGGC AAGAAGAAGA AGAAGAAGA GGAGGGGGAA GGGAAAAAGA 1050
AGGGCGGAGG TGAAGGTGGG GCAGGAGCAG ATGAGGAAAA GGAGCAGTCG 1100
CACAGACCTT TCCTCATGCT GCAGGCCCGG CAGTCTGAAG ACCACCCTCA 1150
```

```
TCGCCGGCGT CGGCGGGGCT TGGAGTGTGA TGGCAAGGTC AACATCTGCT    1200

GTAAGAAACA GTTCTTTGTC AGTTTCAAGG ACATCGGCTG GAATGACTGG    1250

ATCATTGCTC CCTCTGGCTA TCATGCCAAC TACTGCGAGG GTGAGTGCCC    1300

GAGCCATATA GCAGGCACGT CCGGGTCCTC ACTGTCCTTC CACTCAACAG    1350

TCATCAACCA CTACCGCATG CGGGGCCATA GCCCCTTTGC CAACCTCAAA    1400

TCGTGCTGTG TGCCCACCAA GCTGAGACCC ATGTCCATGT TGTACTATGA    1450

TGATGGTCAA AACATCATCA AAAGGACAT TCAGAACATG ATCGTGGAGG     1500

AGTGTGGGTG CTCATAGAGT TGCCCAGCCC AGGGGGAAAG GGAGCAAGAG    1550

TTGTCCAGAG AAGACAGTGG CAAAATGAAG AAATTTTTAA GGTTTCTGAG    1600

TTAACCAGAA AAATAGAAAT TAAAAACAAA ACA                      1633
```

( 2 ) INFORMATION FOR SEQ ID NO:43:

( i ) SEQUENCE CHARACTERISTICS:
        ( A ) LENGTH: 353 amino acids
        ( B ) TYPE: amino acid
        ( D ) TOPOLOGY: linear ( x i ) SEQUENCE DESCRIPTION: SEQ ID NO:43:

```
Cys Thr Ser Cys Gly Gly Phe Arg Arg Pro Glu Glu Leu Gly Arg
 1               5                  10                  15

Val Asp Gly Asp Phe Leu Glu Ala Val Lys Arg His Ile Leu Ser
                20                  25                  30

Arg Leu Gln Met Arg Gly Arg Pro Asn Ile Thr His Ala Val Pro
                35                  40                  45

Lys Ala Ala Met Val Thr Ala Leu Arg Lys Leu His Ala Gly Lys
                50                  55                  60

Val Arg Glu Asp Gly Arg Val Glu Ile Pro His Leu Asp Gly His
                65                  70                  75

Ala Ser Pro Gly Ala Asp Gly Gln Glu Arg Val Ser Glu Ile Ile
                80                  85                  90

Ser Phe Ala Glu Thr Asp Gly Leu Ala Ser Ser Arg Val Arg Leu
                95                  100                 105

Tyr Phe Phe Ile Ser Asn Glu Gly Asn Gln Asn Leu Phe Val Val
                110                 115                 120

Gln Ala Ser Leu Trp Leu Tyr Leu Lys Leu Leu Pro Tyr Val Leu
                125                 130                 135

Glu Lys Gly Ser Arg Arg Lys Val Arg Val Lys Val Tyr Phe Gln
                140                 145                 150

Glu Gln Gly His Gly Asp Arg Trp Asn Met Val Glu Lys Arg Val
                155                 160                 165

Asp Leu Lys Arg Ser Gly Trp His Thr Phe Pro Leu Thr Glu Ala
                170                 175                 180

Ile Gln Ala Leu Phe Glu Arg Gly Glu Arg Arg Leu Asn Leu Asp
                185                 190                 195

Val Gln Cys Asp Ser Cys Gln Glu Leu Ala Val Val Pro Val Phe
                200                 205                 210

Val Asp Pro Gly Glu Glu Ser His Arg Pro Phe Val Val Val Gln
                215                 220                 225

Ala Arg Leu Gly Asp Ser Arg His Arg Ile Arg Lys Arg Gly Leu
                230                 235                 240

Glu Cys Asp Gly Arg Thr Asn Leu Cys Cys Arg Gln Gln Phe Phe
                245                 250                 255
```

| | | | | | | | | | | | | | |
|---|---|---|---|---|---|---|---|---|---|---|---|---|---|
| Ile | Asp | Phe | Arg | Leu<br>260 | Ile | Gly | Trp | Asn | Asp<br>265 | Trp | Ile | Ile | Ala | Pro<br>270 |
| Thr | Gly | Tyr | Tyr | Gly<br>275 | Asn | Tyr | Cys | Glu | Gly<br>280 | Ser | Cys | Pro | Ala | Tyr<br>285 |
| Leu | Ala | Gly | Val | Pro<br>290 | Gly | Ser | Ala | Ser | Ser<br>295 | Phe | His | Thr | Ala | Val<br>300 |
| Val | Asn | Gln | Tyr | Arg<br>305 | Met | Arg | Gly | Leu | Asn<br>310 | Pro | Gly | Thr | Val | Asn<br>315 |
| Ser | Cys | Cys | Ile | Pro<br>320 | Thr | Lys | Leu | Ser | Thr<br>325 | Met | Ser | Met | Leu | Tyr<br>330 |
| Phe | Asp | Asp | Glu | Tyr<br>335 | Asn | Ile | Val | Lys | Arg<br>340 | Asp | Val | Pro | Asn | Met<br>345 |
| Ile | Val | Glu | Glu | Cys<br>350 | Gly | Cys | Ala<br>353 | | | | | | | |

( 2 ) INFORMATION FOR SEQ ID NO:44:

( i ) SEQUENCE CHARACTERISTICS:
        ( A ) LENGTH: 1966 bases
        ( B ) TYPE: nucleic acid
        ( C ) STRANDEDNESS: single
        ( D ) TOPOLOGY: linear ( x i ) SEQUENCE DESCRIPTION: SEQ ID NO:44:

```
CCTGTACGTC GTGCGGCGGC TTCCGGCGGC CAGAGGAGCT CGGCCGAGTG   50
GACGGCGACT TCCTGGAGGC GGTGAAGCGG CACATCTTGA GCCGCCTGCA  100
GATGCGGGGC CGGCCCAACA TCACGCACGC CGTGCCTAAG GCCGCCATGG  150
TCACGGCCCT GCGCAAGCTG CACGCGGGCA AGGTGCGCGA GGACGGCCGC  200
GTGGAGATCC CGCACCTCGA CGGCCACGCC AGCCCGGGCG CCGACGGCCA  250
GGAGCGCGTT TCCGAAATCA TCAGCTTCGC CGAGACAGAT GGCCTCGCCT  300
CCTCCCGGGT CCGCCTATAC TTCTTCATCT CCAACGAAGG CAACCAGAAC  350
CTGTTTGTGG TCCAGGCCAG CCTGTGGCTT TACCTGAAAC TCCTGCCCTA  400
CGTCCTGGAG AAGGGCAGCC GGCGGAAGGT GCGGGTCAAA GTGTACTTCC  450
AGGAGCAGGG CCACGGTGAC AGGTGGAACA TGGTGGAGAA GAGGGTGGAC  500
CTCAAGCGCA GCGGCTGGCA TACCTTCCCA CTCACGGAGG CCATCCAGGC  550
CTTGTTTGAG CGGGGCGAGC GGCGACTCAA CCTAGACGTG CAGTGTGACA  600
GCTGCCAGGA GCTGGCCGTG GTGCCGGTGT CGTGGACCC AGGCGAAGAG  650
TCGCACCGGC CCTTTGTGGT GGTGCAGGCT CGGCTGGGCG ACAGCAGGCA  700
CCGCATTCGC AAGCGAGGCC TGGAGTGCGA TGGCCGGACC AACCTCTGTT  750
GCAGGCAACA GTTCTTCATT GACTTCCGCC TCATCGGCTG GAACGACTGG  800
ATCATAGCAC CCACCGGCTA CTACGGGAAC TACTGTGAGG GCAGCTGCCC  850
AGCCTACCTG GCAGGGGTCC CCGGCTCTGC CTCCTCCTTC CACACGGCTG  900
TGGTGAACCA GTACCGCATG CGGGGTCTGA ACCCCGGCAC GGTGAACTCC  950
TGCTGCATTC CCACCAAGCT GAGCACCATG TCCATGCTGT ACTTCGATGA 1000
TGAGTACAAC ATCGTCAAGC GGGACGTGCC CAACATGATT GTGGAGGAGT 1050
GCGGCTGCGC CTGACAGTGC AAGGCAGGGG CACGGTGGTG GGGCACGGAG 1100
GGCAGTCCCG GGTGGGCTTC TTCCAGCCCC GCGGGAACG GGTACACGG 1150
TGGGCTGAGT ACAGTCATTC TGTTGGGCTG TGGAGATAGT GCCAGGGTGC 1200
```

```
GGCCTGAGAT ATTTTTCTAC AGCTTCATAG AGCAACCAGT CAAAACCAGA 1250

GCGAGAACCC TCAACTGACA TGAAATACTT TAAAATGCAC ACGTAGCCAC 1300

GCACAGCCAG ACGCATCCTG CCACCCACAC AGCAGCCTCC AGGATACCAG 1350

CAAATGGATG CGGTGACAAA TGGCAGCTTA GCTACAAATG CCTGTCAGTC 1400

GGAGAGAATG GGGTGAGCAG CCACCATTCC ACCAGCTGGC CCGGCCACGT 1450

CTCGAAGTTG CGCCTTCCCG AGCACACATA AAAGCACAAA GACAGAGACG 1500

CAGAGAGAGA GAGAGAGCCA CGGAGAGGAA AAGCAGATGC AGGGGTGGGG 1550

AGCGCAGCTC GGCGGAGGCT GCGTGTGCCC CGTGGCTTTT ACCAGGCCTG 1600

CTCTGCCTGG CTCGATGTCT GCTTCTTCCC AGCCTGGGAT CCTTCGTGCT 1650

TCAAGGCCTG GGGAGCCTGT CCTTCCATGC CCTTGTCGAG GGAAAGAGAC 1700

CCAGAAAGGA CACAACCCGT CAGAGACCTG GGAGCAGGGG CAATGACCGT 1750

TTGACTGTTT GTGGCTTGGG CCTCTGACAT GACTTATGTG TGTGTGTGTT 1800

TTTGGGGTGG GGAGGGAGGG AGAGAAGAGG GGGCTAAATT TGATGCTTTA 1850

ACTGATCTCC AACAGTTGAC AGGTCATCCT TGCCAGTTGT ATAACTGAAA 1900

AAGGACTTTT CTACCAGGTA TGACCTTTTA AGTGAAAATC TGAATTGTTC 1950

TAAATGAAAA GAAAAA                                     1966
```